(12) United States Patent
Stoessel et al.

(10) Patent No.: US 8,865,321 B2
(45) Date of Patent: Oct. 21, 2014

(54) ORGANIC ELECTROLUMINESCENT DEVICES

(75) Inventors: Philipp Stoessel, Frankfurt (DE); Holger Heil, Frankfurt (DE); Dominik Joosten, Frankfurt (DE); Christof Pflumm, Frankfurt (DE); Anja Gerhard, Egelsbach (DE); Esther Breuning, Ober-Ramstadt (DE); Amir Hossain Parham, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 644 days.

(21) Appl. No.: 13/001,731

(22) PCT Filed: Oct. 15, 2009

(86) PCT No.: PCT/EP2009/007406
§ 371 (c)(1),
(2), (4) Date: May 2, 2011

(87) PCT Pub. No.: WO2010/054730
PCT Pub. Date: May 20, 2010

(65) Prior Publication Data
US 2011/0201778 A1   Aug. 18, 2011

(30) Foreign Application Priority Data

Nov. 11, 2008 (DE) .................. 10 2008 056 688
May 7, 2009 (DE) .................. 10 2009 022 858

(51) Int. Cl.
| | | |
|---|---|---|
| H01L 51/54 | (2006.01) | |
| C08G 73/06 | (2006.01) | |
| C08G 79/04 | (2006.01) | |
| C07F 9/6584 | (2006.01) | |
| C09B 57/10 | (2006.01) | |
| H01L 51/50 | (2006.01) | |
| H01L 51/00 | (2006.01) | |
| C09B 57/00 | (2006.01) | |
| C07F 9/6571 | (2006.01) | |
| C07D 401/04 | (2006.01) | |
| C09K 11/06 | (2006.01) | |

(52) U.S. Cl.
CPC ......... *C09K 11/06* (2013.01); *C09K 2211/1007* (2013.01); *C09B 57/10* (2013.01); *H01L 51/5016* (2013.01); *C09K 2211/1011* (2013.01); *H01L 51/0071* (2013.01); *C09K 2211/1055* (2013.01); *Y02E 10/549* (2013.01); *C09B 57/00* (2013.01); *C07F 9/657181* (2013.01); *C07D 401/04* (2013.01); *C07F 9/65848* (2013.01); *H01L 51/0067* (2013.01); *C07F 9/65844* (2013.01); *Y10S 428/917* (2013.01)
USPC .......... 428/690; 428/917; 313/504; 313/506; 257/40; 528/399; 564/13; 564/22; 544/195; 544/243

(58) Field of Classification Search
CPC ............ C07D 401/04; C07F 9/657181; C07F 9/65844; C07F 9/65848; H01L 51/0071; H01L 51/0067; H01L 51/5016; C09B 57/00; C09B 57/10; C09K 2211/1007; C09K 2211/1011; C09K 2211/1055
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,621,131 A | 4/1997 | Kreuder et al. | |
| 6,103,459 A * | 8/2000 | Diel | .............................. 430/530 |
| 6,653,438 B1 | 11/2003 | Spreitzer et al. | |
| 7,820,822 B2 | 10/2010 | Fortte et al. | |
| 7,880,379 B2 | 2/2011 | Gerhard et al. | |
| 2005/0069729 A1 | 3/2005 | Ueda et al. | |
| 2005/0258742 A1 | 11/2005 | Tsai et al. | |
| 2006/0149022 A1 | 7/2006 | Parham et al. | |
| 2006/0284140 A1 | 12/2006 | Breuning et al. | |
| 2007/0060736 A1 | 3/2007 | Becker et al. | |
| 2007/0205714 A1 | 9/2007 | Busing et al. | |
| 2009/0226759 A1 | 9/2009 | Heun et al. | |
| 2010/0102305 A1 | 4/2010 | Heun et al. | |
| 2010/0187977 A1 | 7/2010 | Kai et al. | |
| 2010/0288974 A1 | 11/2010 | Buesing et al. | |
| 2010/0297684 A1 * | 11/2010 | Miller | ............................. 435/29 |
| 2011/0049501 A1 | 3/2011 | Bold et al. | |

FOREIGN PATENT DOCUMENTS

| | | |
|---|---|---|
| DE | 102008033943 A1 | 1/2010 |
| DE | 102008036982 A1 | 2/2010 |
| DE | 102008056688 A1 | 5/2010 |
| EP | 0652273 A1 | 5/1995 |
| EP | 0676461 A2 | 10/1995 |
| EP | 0707020 A2 | 4/1996 |
| EP | 0842208 A1 | 5/1998 |
| EP | 0894107 B1 | 12/1999 |
| EP | 1028136 A2 | 8/2000 |
| EP | 1191612 A2 | 3/2002 |

(Continued)

OTHER PUBLICATIONS

Lister et al., "Synthesis and Properties of 1,3-Diaza-1,3-Dihydro-2-Phospholo(4,5-*d*)-Pyrimidine 2-Oxides," *J. Chem. Soc. (C)*, No. 14, pp. 1242-1244 (1966).

Anisimova et al., "Diaminophosphenium Ions in the Mass Spectra of 2,3-Dihydro-1H-1,3,2-Benzodiazaphospholes," *Journal of General Chemistry USSR*, vol. 46, pp. 807-811 (1976).

(Continued)

*Primary Examiner* — Dawn Garrett
(74) *Attorney, Agent, or Firm* — Drinker Biddle & Reath LLP

(57) ABSTRACT

The present invention relates to electronic devices, in particular organic electroluminescent devices, which comprise compounds of the formula (1), and to the corresponding compounds and to the use thereof in organic electroluminescent devices.

22 Claims, No Drawings

(56) References Cited

FOREIGN PATENT DOCUMENTS

| | | |
|---|---|---|
| EP | 1191613 A2 | 3/2002 |
| EP | 1191614 A2 | 3/2002 |
| EP | 1205527 A1 | 5/2002 |
| EP | 1617710 A1 | 1/2006 |
| EP | 1617711 A1 | 1/2006 |
| EP | 1731584 A1 | 12/2006 |
| GB | 884016 * | 12/1961 |
| JP | 2004-288381 A | 10/2004 |
| JP | 2005-347160 A | 12/2005 |
| JP | 2007-329495 A | 12/2007 |
| WO | WO-92/18552 A1 | 10/1992 |
| WO | WO-00/22026 A1 | 4/2000 |
| WO | WO-00/70655 A2 | 11/2000 |
| WO | WO-01/41512 A1 | 6/2001 |
| WO | WO-02/02714 A2 | 1/2002 |
| WO | WO-02/15645 A1 | 2/2002 |
| WO | WO-2004/013080 A1 | 2/2004 |
| WO | WO-2004/041901 A1 | 5/2004 |
| WO | WO-2004/070772 A2 | 8/2004 |
| WO | WO-2004/093207 A2 | 10/2004 |
| WO | WO-2004/113412 A2 | 12/2004 |
| WO | WO-2004/113468 A1 | 12/2004 |
| WO | WO-2005/003253 A2 | 1/2005 |
| WO | WO-2005/011013 A1 | 2/2005 |
| WO | WO-2005/014689 A2 | 2/2005 |
| WO | WO-2005/019373 A2 | 3/2005 |
| WO | WO-2005/033244 A1 | 4/2005 |
| WO | WO-2005/039246 A1 | 4/2005 |
| WO | WO-2005/040302 A1 | 5/2005 |
| WO | WO-2005/053051 A1 | 6/2005 |
| WO | WO-2005/104264 A1 | 11/2005 |
| WO | WO-2005/111172 A2 | 11/2005 |
| WO | WO-2006/005627 A1 | 1/2006 |
| WO | WO-2006/061181 A1 | 6/2006 |
| WO | WO-2006/117052 A1 | 11/2006 |
| WO | WO-2007/017066 A1 | 2/2007 |
| WO | WO-2007/063754 A1 | 6/2007 |
| WO | WO-2007/137725 A1 | 12/2007 |
| WO | WO-2008/056746 A1 | 5/2008 |
| WO | WO-2008/086851 A1 | 7/2008 |
| WO | WO-2009/030981 A2 | 3/2009 |
| WO | WO-2009/062578 A1 | 5/2009 |

OTHER PUBLICATIONS

Anchisi et al., "Studies on the Synthesis of Heterocyclic Compounds. V. Preparation of 1,3,2-Benzoxathiaphosphole, Arsole and Stibole Derivatives by Exchange Methods," *J. Heterocyclic Chem.*, vol. 16, pp. 1439-1441 (1979).

Ogawa et al., "Preparation and Multi-Nuclear NMR Study of New Benzodichalcogenaphospholes," *Heterocycles*, vol. 41, No. 5, pp. 889-892 (1995).

Anchisi, C., et al., "Studies on the Synthesis of Heterocyclic Compounds. V. Preparation of 1,3,2-Benzoxuthisphosphole, Arsole and Stibole Derivatives by Exchange Methods", Journal Heterocyclic Chemistry, vol. 16, (1979), pp. 1439-1441.

Ogawa, S., et al., "Preparation and Multi-Nuclear NMR Study of New Benzodichalcogenaphospholes", Heterocycles, vol. 41, No. 5, (1995), pp. 889-892.

Anisimova, O., "Diaminophosphenium Ions in The Mass Spectra of 2,3-Dihydro-1H-1,3,2-Benzodiazaphospholes", Journal of General Chemistry, vol. 46, (1976), pp. 807-811.

Lister, J., Synthesis and Properties of 1,3-Diaza-1,3-Dihydro-2-Phospholo [4.5-d]-Pyrimidine 2-Oxides, Journal of the Chemical Society, (1966), pp. 1242-1244.

* cited by examiner

ORGANIC ELECTROLUMINESCENT DEVICES

RELATED APPLICATIONS

This application is a national stage application (under 35 U.S.C. §371) of PCT/EP2009/007406, filed Oct. 15, 2009, which claims benefit of German Application No. 10 2008 056 688.8, filed Nov. 11, 2008, and German Application No. 10 2009 022 858.6, filed May 27, 2009.

The present invention relates to organic electroluminescent devices and to materials for use in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs, in particular also in OLEDs which exhibit triplet emission, in particular with respect to the efficiency, operating voltage and lifetime. This applies, in particular, to OLEDs which emit in the relatively short-wave range, i.e. green and in particular blue. Thus, no devices comprising blue-emitting triplet emitters which meet the technical requirements for industrial use have been disclosed to date.

The properties of phosphorescent OLEDs are not determined only by the triplet emitters employed. In particular, the other materials used, such as matrix materials, hole-blocking materials, electron-transport materials, hole-transport materials and electron- and exciton-blocking materials, are also of particular importance here. Improvements in these materials can thus also result in significant improvements in the OLED properties. There is still a need for improvement in these materials, including for fluorescent OLEDs.

In accordance with the prior art, ketones (for example in accordance with WO 04/093207 or in accordance with the unpublished application DE 102008033943.1) or phosphine oxides (for example in accordance with WO 05/003253), inter alia, are used as matrix materials for phosphorescent emitters.

However, there is still a need for improvement, in particular with respect to the efficiency and lifetime of the device, on use of these matrix materials as in the case of other matrix materials.

The object of the present invention is to provide compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, the object of the present invention is to provide matrix materials which are also suitable for blue- and green-phosphorescent OLEDs.

Surprisingly, it has been found that certain compounds described in greater detail below achieve this object and result in significant improvements in the organic electroluminescent device, in particular with respect to the lifetime, the efficiency and the operating voltage. This applies, in particular, to blue- and green-phosphorescent electroluminescent devices, especially on use of the compounds according to the invention as matrix material. The present invention therefore relates to organic electroluminescent devices which comprise compounds of this type and to the corresponding compounds.

The present invention relates to an electronic device comprising at least one compound of the following formula (1):

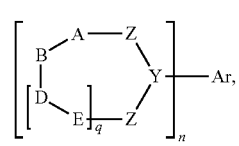

formula (1)

where the following applies to the symbols and indices used:
A-B and D-E are each, identically or differently on each occurrence, a unit of the following formula (2), (3), (4), (5) or (6):

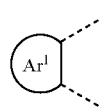

formula (2)

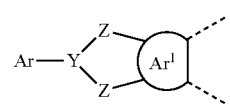

formula (3)

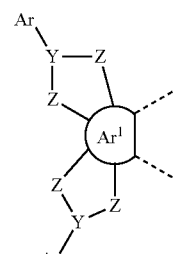

formula (4)

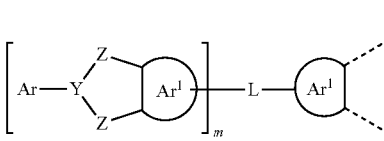

formula (5)

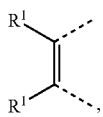

formula (6)

where the dashed bond in each case represents the link to Z;
and
Z is, identically or differently on each occurrence, $N-R^2$, O or S;
or
A-Z and B-Z are each, identically or differently on each occurrence, a unit of the following formula (7) and q=0,

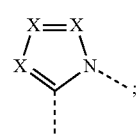

formula (7)

the dashed bond in formula (7) in each case represents the linking of this unit in the compound of the formula (1), where the nitrogen is linked to the group Y;
Y is on each occurrence, identically or differently, P(=O), P(=S), P, As(=O), As(=S), As, Sb(=O), Sb(=S), Sb, Bi(=O), Bi(=S) or Bi;

Ar is on each occurrence, identically or differently, an aromatic or heteroaromatic ring system having 5 to 60 aromatic ring atoms, which may be substituted by one or more radicals $R^1$;

$Ar^1$ is on each occurrence, identically or differently, an aryl or heteroaryl group having 5 to 18 aromatic ring atoms, which may be substituted by one or more radicals $R^1$;

X is on each occurrence, identically or differently, $CR^1$ or N;

L is a single bond or a divalent, trivalent or tetravalent group;

$R^1$ is selected on each occurrence, identically or differently, from the group consisting of H, D, F, Cl, Br, I, CN, $NO_2$, $N(R^3)_2$, $C(=O)R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of a straight-chain alkyl group having 1 to 40 C atoms or a branched or cyclic alkyl group having 3 to 40 C atoms, each of which may be substituted by one or more radicals $R^3$, where one or more non-adjacent $CH_2$ groups may be replaced by $R^3C=CR^3$, $C\equiv C$ or $C=O$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

n is 1 to 10, preferably 1, 2, 3, 4, 5 or 6;

m is 1 if L is a single bond or a divalent group, or is 2 if L is a trivalent group, or is 3 if L is a tetravalent group;

q is on each occurrence, identically or differently, 0 or 1.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. By contrast, aromatic rings which are linked to one another by a single bond, such as, for example, biphenyl, are not regarded as an aryl or heteroaryl group, but instead as an aromatic ring system.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a short alkyl group.

For the purposes of the present invention, an aliphatic hydrocarbon radical or an alkyl group or an alkenyl or alkynyl group, which may typically contain 1 to 40 or also 1 to 20 C atoms, and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynytthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-60 aromatic ring atoms, which may also in each case be substituted by the above-mentioned radicals $R^3$ or a hydrocarbon radical and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole; 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

If the compound of the formula (1) contains a unit of one or more of formulae (2) to (5), $Ar^1$ preferably stands, identically or differently on each occurrence, for an aryl or heteroaryl group having 5 to 14 aromatic ring atoms, particularly preferably having 5 to 10 aromatic ring atoms, very particularly preferably having 6 aromatic ring atoms. Particularly suitable aryl and heteroaryl groups $Ar^1$ are selected, identically or differently on each occurrence, from the group consisting of benzene, pyridine, pyrimidine, pyridazine, pyrazine, triazine, furan, thiophene, pyrrole, naphthalene, phenanthrene, quinoline, isoquinoline, quinoxaline, indole, benzofuran, benzothiophene and carbazole.

Preferred embodiments of the compounds of the abovementioned formula (1) are the compounds of the formulae (8) to (18):

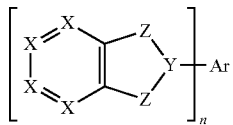

formula (8)

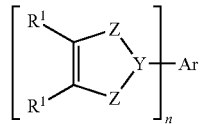

formula (9)

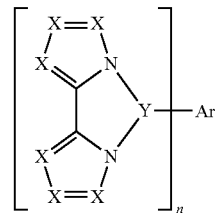

formula (10)

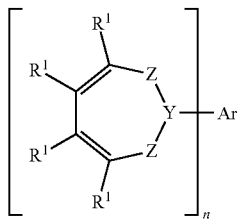

formula (11)

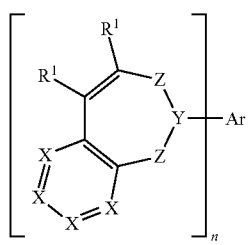

formula (12)

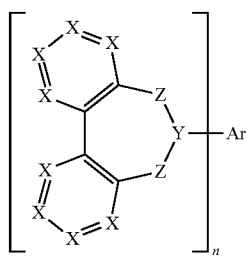

formula (13)

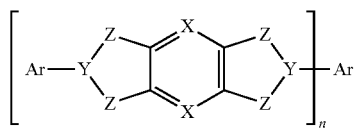

formula (14)

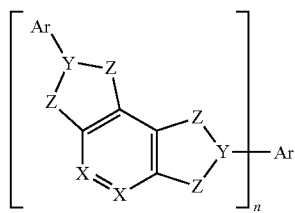

formula (15)

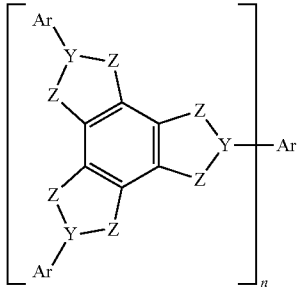

formula (16)

-continued

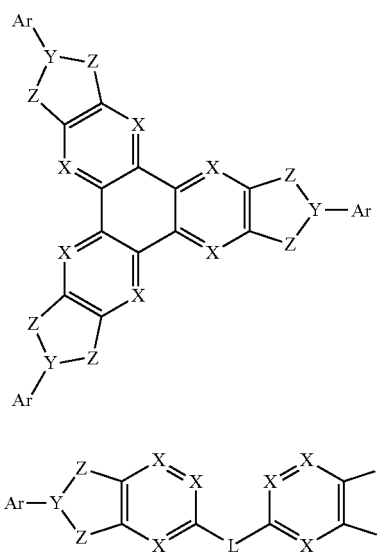

formula (17)

formula (18)

where the symbols and indices used have the meanings indicated above.

In a preferred embodiment of the compounds of the formula (1) or formulae (8) to (18), the symbol Y stands on each occurrence, identically or differently, for P(=O), P(=S) or P. The symbol Y particularly preferably stands for P(=O) or P(=S), very particularly preferably for P(=O).

In a further preferred embodiment of the compounds of the formula (1) or formulae (8) to (18), the symbol Z, if it does not form a ring of the formula (7) with A or B, stands, identically or differently on each occurrence, for N—$R^2$.

In a particularly preferred embodiment of the compounds of the formula (1) or formulae (8) to (18), the symbol Y stands for P(=O) and the symbol Z stands on each occurrence, identically or differently, for N—$R^2$.

In a further preferred embodiment of the compounds of the formula (1) or formula (18), the symbol L stands for a single bond, O, S, $NR^2$, an alkylene group having 1 to 10 C atoms, which may be substituted by one or more radicals $R^3$, or an aromatic or heteroaromatic ring system having 5 to 30 aromatic ring atoms, which may be substituted by one or more radicals $R^3$.

In a further preferred embodiment of the invention, a maximum of two symbols X in each ring stand for N and the other symbols X stand, identically or differently on each occurrence, for $CR^1$. Particularly preferably, a maximum of one symbol X in each ring stands for N and the other symbols X stand, identically or differently on each occurrence, for $CR^1$. Very particularly preferably, all symbols X stand, identically or differently on each occurrence, for $CR^1$.

In a further preferred embodiment of the invention, the group Ar stands for an aromatic or heteroaromatic ring system having 5 to 30 aromatic ring atoms, particularly preferably having 5 to 24 aromatic ring atoms. Preferably, none of the aryl or heteroaryl groups of the aromatic or heteroaromatic ring system contains more than 10 aromatic ring atoms. Preferred groups Ar are therefore built up from in each case one or more of the groups benzene, pyridine, pyrimidine, pyridazine, pyrazine, triazine, pyrrole, thiophene, furan, naphthalene, quinoline, isoquinoline, quinoxaline, indole, benzothiophene or benzofuran. Particularly preferred groups Ar are built up from in each case one or more of the groups benzene, pyridine, pyrimidine, pyridazine, pyrazine or triazine, in particular benzene. A further preferred group Ar is triphenylene.

In a particularly preferred embodiment of the invention, Ar is selected from the group consisting of the units of the following formulae (19) to (36), where the dashed bond in each case indicates a link to the group Y:

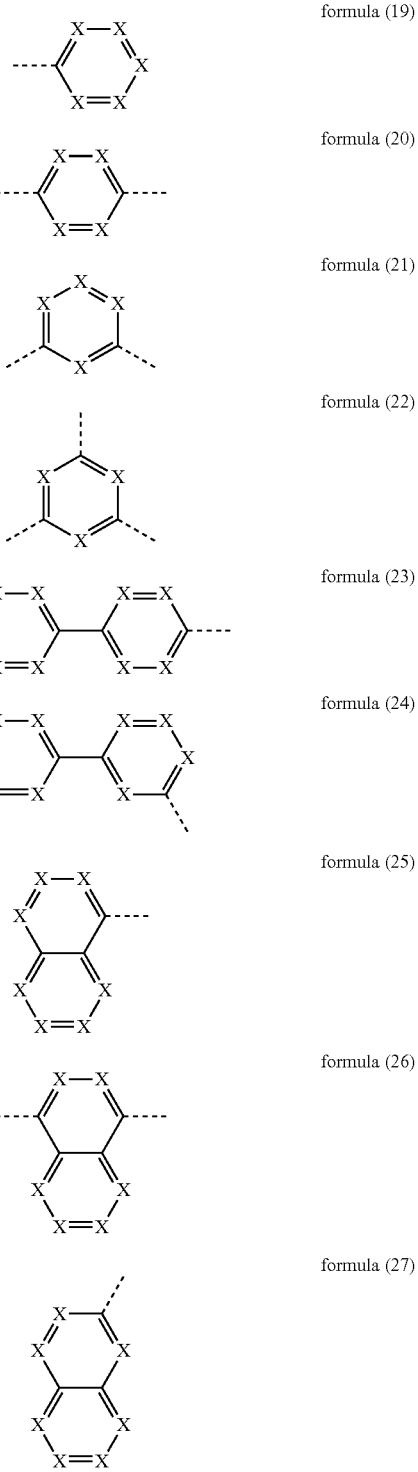

formula (28)

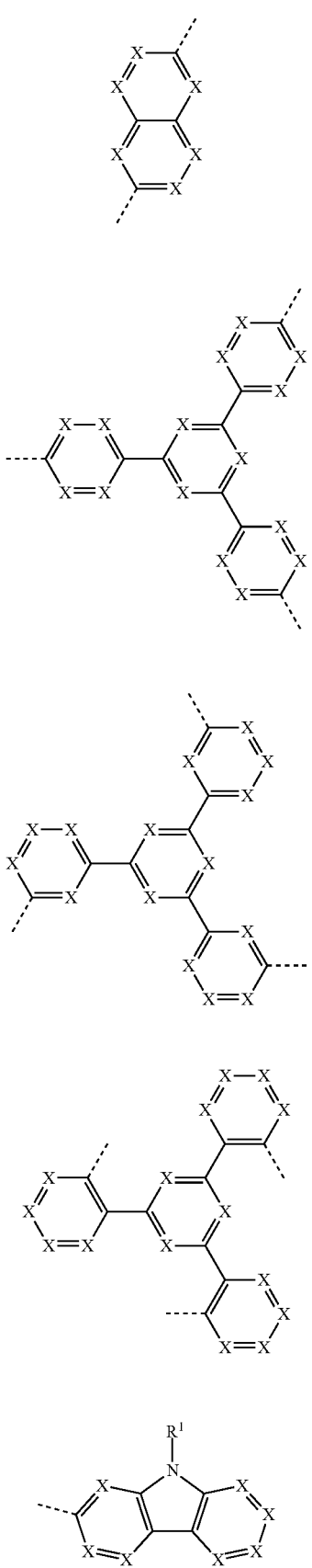

formula (29)

formula (30)

formula (31)

formula (32)

formula (33)

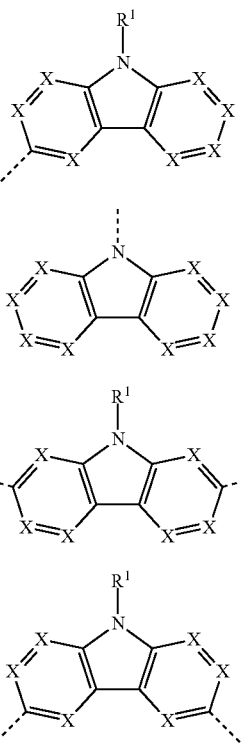

formula (34)

formula (35)

formula (36)

In a further preferred embodiment of the invention, the index q=0.

In a further preferred embodiment of the invention, the index n=1, 2, 3 or 4, particularly preferably 1, 2 or 3, very particularly preferably 1 or 2.

In a further preferred embodiment of the invention, the radical $R^1$ is selected, identically or differently on each occurrence, from the group consisting of H, D, F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C=CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$. The radical $R^1$ is particularly preferably selected, identically or differently on each occurrence, from the group consisting of H, D, CN, F, a straight-chain alkyl group having 1 to 10 C atoms, particularly preferably having 1 to 4 C atoms, or a branched or cyclic alkyl group having 3 to 10 C atoms, particularly preferably having 3 to 6 C atoms, or an alkenyl group having 2 to 10 C atoms, particularly preferably having 2 to 4 C atoms, each of which may be substituted by one or more radicals $R^3$, where one or more H atoms may be replaced by D, an aromatic or heteroaromatic ring system having 5 to 12 aromatic ring atoms, which may in each case be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$.

In a further preferred embodiment of the invention, $R^2$ is selected on each occurrence, identically or differently, from the group consisting of a straight-chain alkyl group having 1 to 10 C atoms or a branched or cyclic alkyl group having 3 to 10 C atoms, each of which may be substituted by one or more radicals $R^3$, where one or more H atoms may be replaced by D or F, an aromatic or heteroaromatic ring system having 5 to 30 aromatic ring atoms, which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$. In a particularly preferred embodiment of the invention, $R^2$ is selected on each occurrence, identically or differently, from the group consisting of an aromatic or heteroaromatic ring system having 5 to 24 aromatic ring atoms, which may in each case be substituted by one or more radicals $R^3$. In a very particularly preferred embodiment of the invention, $R^2$ stands for phenyl, naphthyl, biphenyl or terphenyl, each of which may be substituted by one or more radicals $R^3$, in particular for phenyl or biphenyl, each of which may be substituted by one or more radicals $R^3$, but is preferably unsubstituted.

Particular preference is given to compounds of the formulae (1) and (8) to (18) indicated above in which the above-mentioned preferences apply simultaneously. Particular preference is therefore given to compounds in which $R^3$ is as defined above and furthermore:

$Ar^1$ is, identically or differently on each occurrence, an aryl or heteroaryl group having 5 to 14 aromatic ring atoms, particularly preferably having 5 to 10 aromatic ring atoms, very particularly preferably having 6 aromatic ring atoms;

Y is on each occurrence, identically or differently, P(=O) or P(=S);

Z is, identically or differently on each occurrence, N—$R^2$ if it does not form a ring of the formula (7) with A or B;

X stands for $CR^1$ or N, where a maximum of two symbols X stand for N, preferably a maximum of one symbol X stands for N;

Ar is, identically or differently, an aromatic or heteroaromatic ring system having 5 to 30 aromatic ring atoms, particularly preferably having 5 to 24 aromatic ring atoms; preferably; none of the aryl or heteroaryl groups of the aromatic or heteroaromatic ring system contains more than 10 aromatic ring atoms;

q is 0;

n is 1, 2, 3 or 4, preferably 1, 2 or 3;

$R^1$ is selected, identically or differently on each occurrence, from the group consisting of H, D, F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C$=$CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of a straight-chain alkyl group having 1 to 10 C atoms or a branched or cyclic alkyl group having 3 to 10 C atoms, each of which may be substituted by one or more radicals $R^3$, where one or more H atoms may be replaced by F or D, an aromatic or heteroaromatic ring system having 5 to 30 aromatic ring atoms, which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$.

Very particular preference is given to compounds of the formula (1) or formulae (8) to (18) in which $R^3$ is as defined above and furthermore:

$Ar^1$ is selected, identically or differently on each occurrence, from the group consisting of benzene, pyridine, pyrimidine, pyridazine, pyrazine, triazine, furan, thiophene, pyrrole, naphthalene, quinoline, isoquinoline, quinoxaline, indole, benzofuran, benzothiophene and carbazole;

Y is P(=O);

Z is, identically or differently on each occurrence, N—$R^2$ if it does not form a ring of the formula (7) with A or B;

X is, identically or differently on each occurrence, $CR^1$;

Ar is an aromatic or heteroaromatic ring system having 5 to 24 aromatic ring atoms, which is built up from in each case one or more of the groups benzene, pyridine, pyrimidine, pyridazine, pyrazine, pyrrole, thiophene, furan, naphthalene, triphenylene, quinoline, isoquinoline, quinoxaline, indole, benzothiophene or benzofuran, preferably from in each case one or more of the groups benzene, pyridine, pyrimidine, pyridazine, pyrazine or triazine, in particular benzene;

q is 0;

n is 1 or 2;

$R^1$ is selected, identically or differently on each occurrence, from the group consisting of H, D, F, CN, a straight-chain alkyl group having 1 to 10 C atoms, preferably having 1 to 4 C atoms, or a branched or cyclic alkyl group having 3 to 10 C atoms, particularly preferably having 3 to 5 C atoms, or an alkenyl group having 2 to 10 C atoms, preferably having 2 to 4 C atoms, each of which may be substituted by one or more radicals $R^3$, where one or more H atoms may be replaced by D, an aromatic or heteroaromatic ring system having 5 to 12 aromatic ring atoms, which may in each case be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of an aromatic or heteroaromatic ring system having 5 to 24 aromatic ring atoms, which may in each case be substituted by one or more radicals $R^3$.

For compounds which are processed from solution, suitable substituents are, in particular, also long alkyl groups, for example having 5 to 10 C atoms, or substituted or unsubstituted oligoarylene groups. Suitable oligoarylene groups are, for example, terphenyl, in particular meta-terphenyl, branched terphenyl, meta-quarterphenyl or branched quarterphenyl.

Preference is furthermore given to compounds in which all radicals $R^2$ are selected identically.

Examples of preferred compounds in accordance with the above-mentioned embodiments or compounds as can preferably be employed in organic electronic devices are the compounds of the following structures (1) to (274).

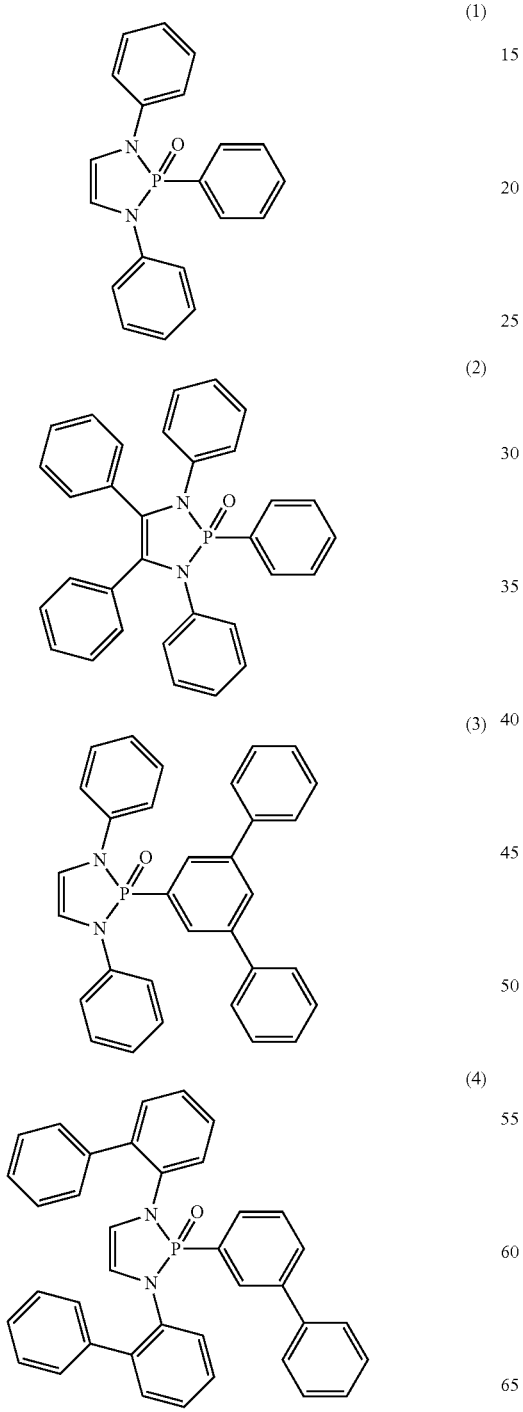

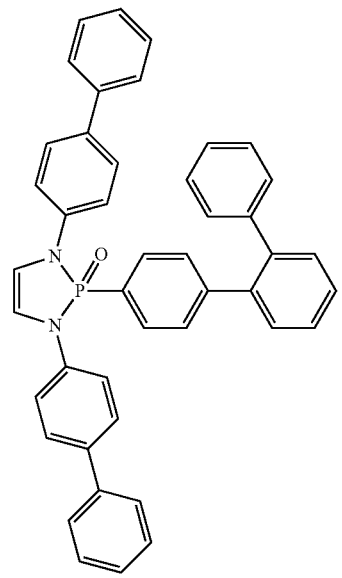

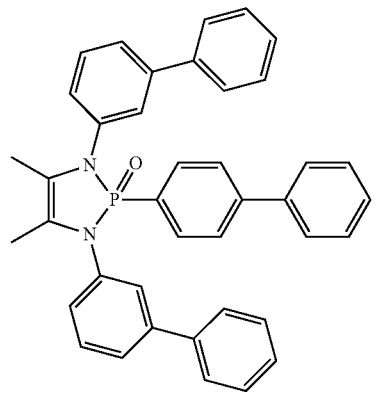

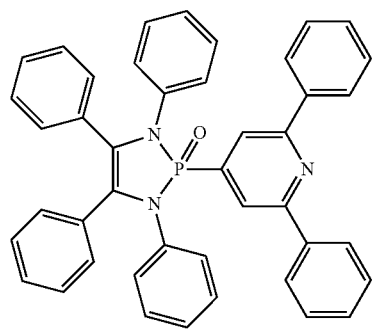

-continued
(8)
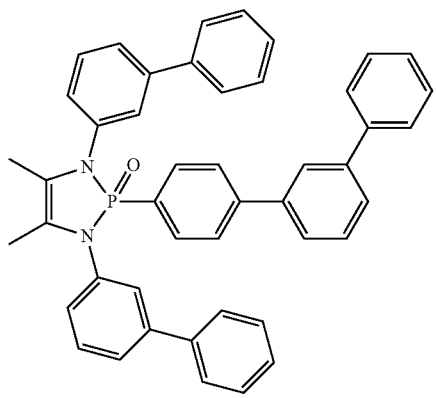
(9)
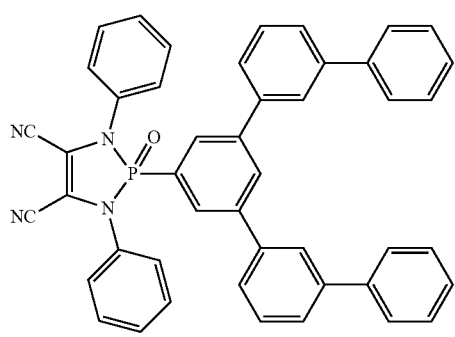
(10)
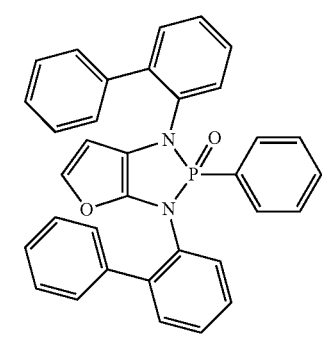
(11)
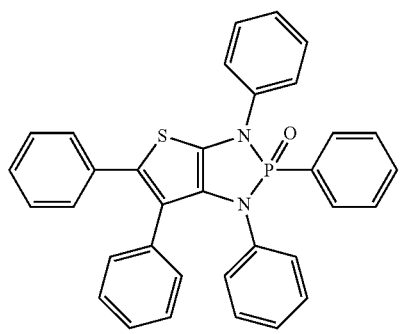
(12)
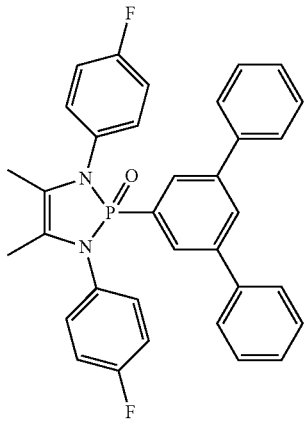
(13)
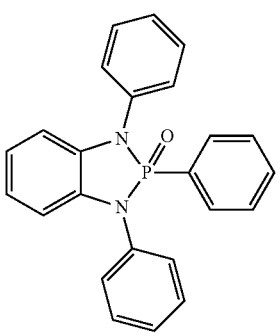
(14)
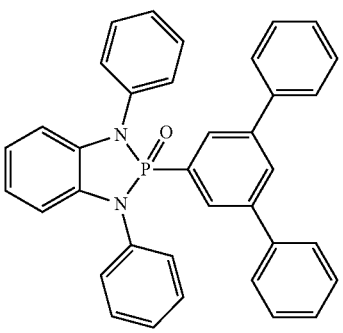
(15)
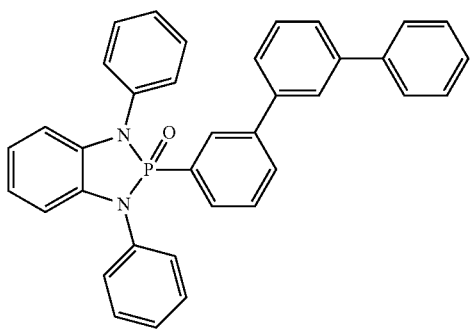

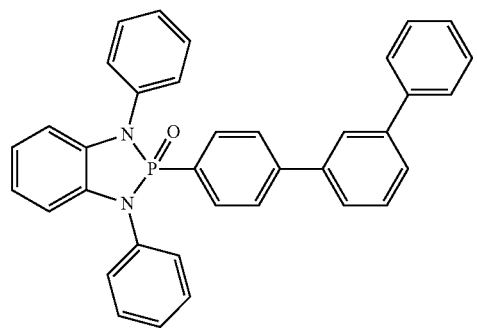
(16)
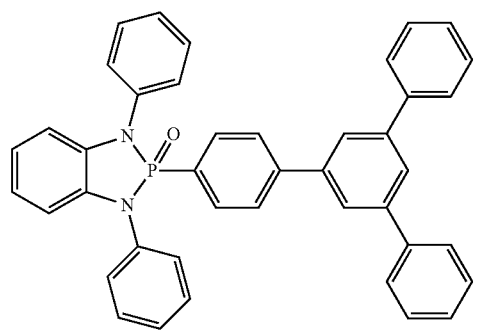
(17)
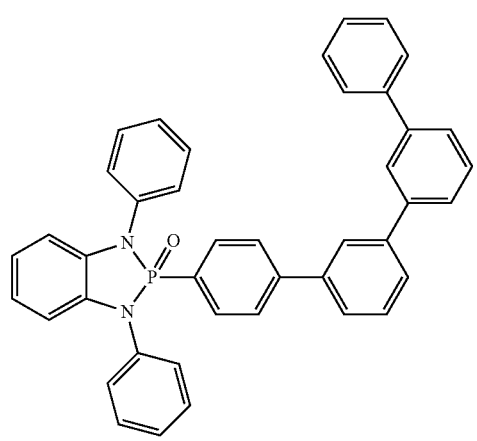
(18)
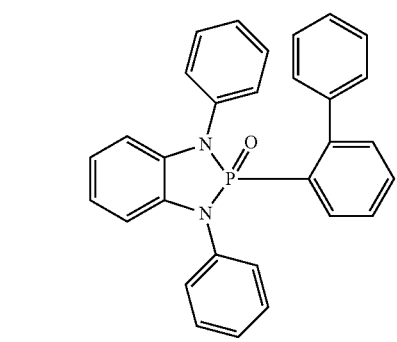
(19)
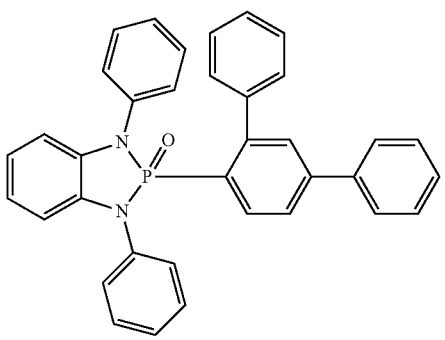
(20)
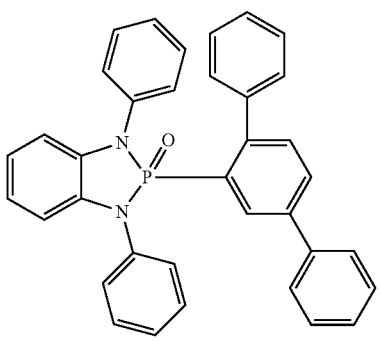
(21)
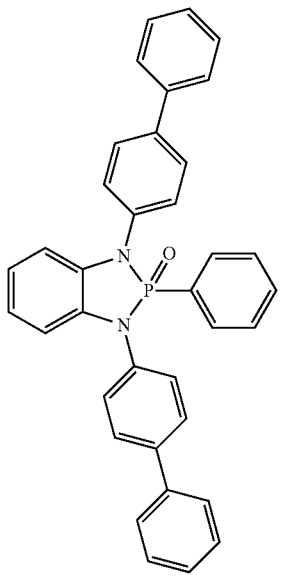
(22)
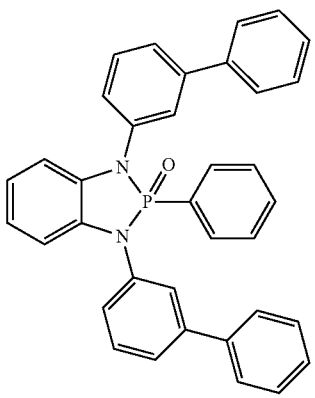
(23)

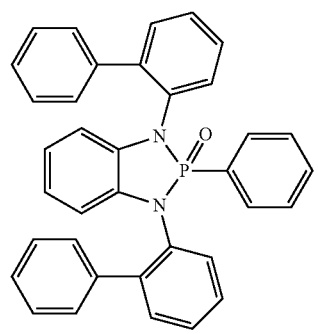
(24)
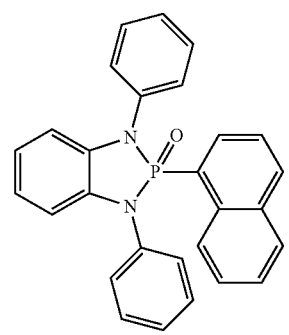
(25)
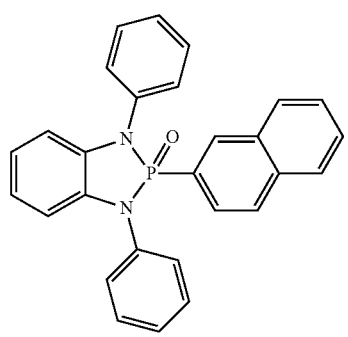
(26)
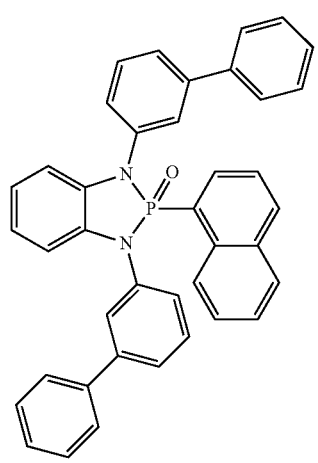
(27)
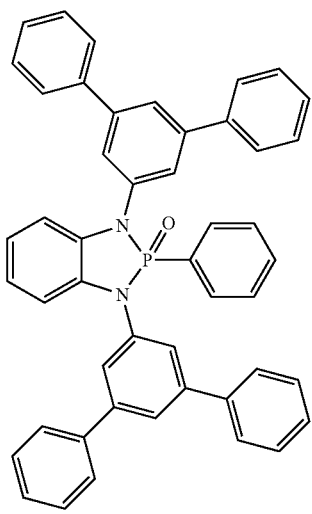
(28)
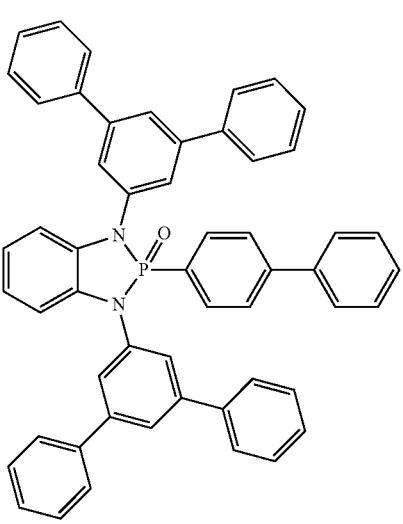
(29)
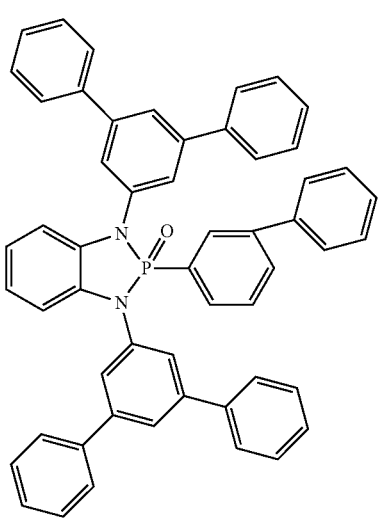
(30)

-continued
(31)
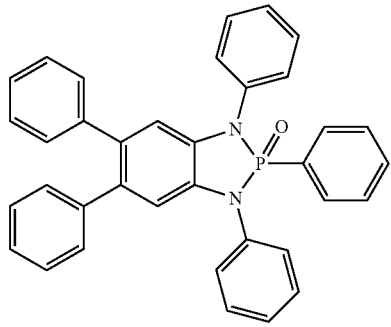
(32)
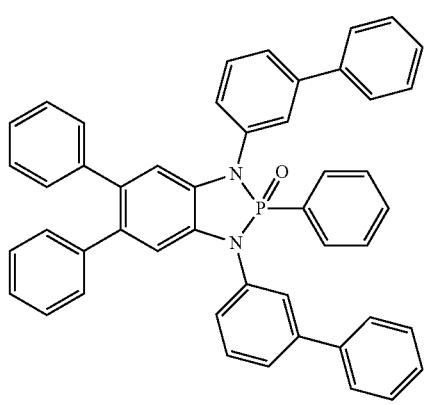
(33)
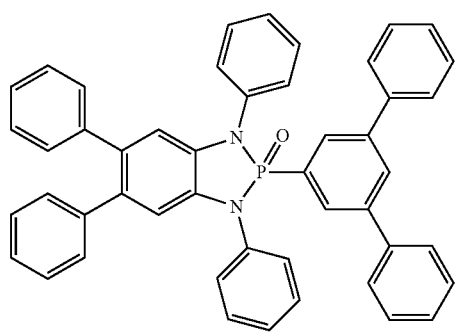
(34)
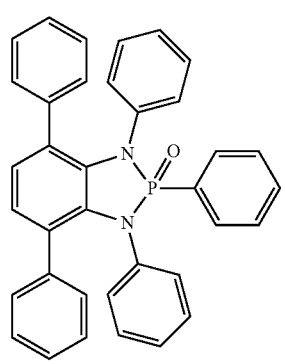
(35)
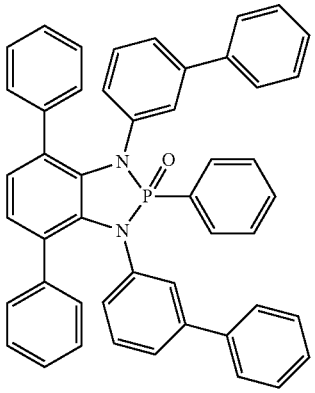
(36)
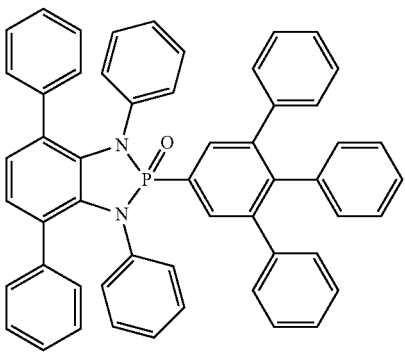
(37)
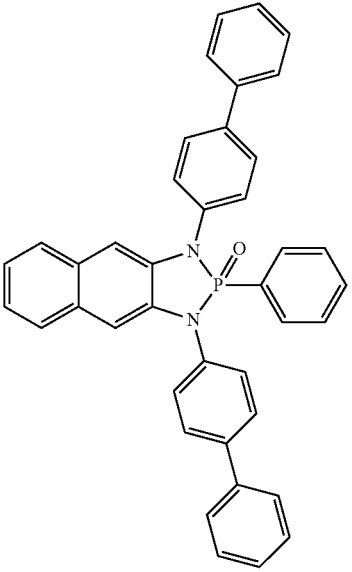
(38)
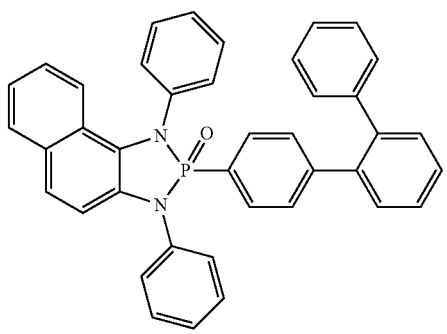

(39)
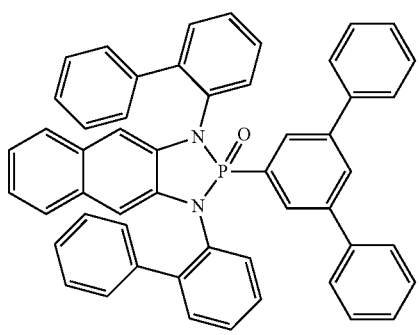
(40)
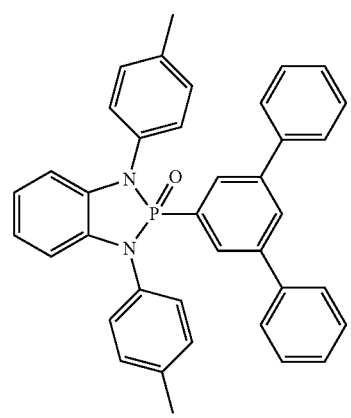
(41)
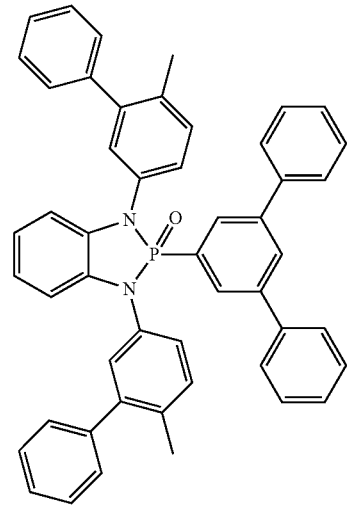
(42)
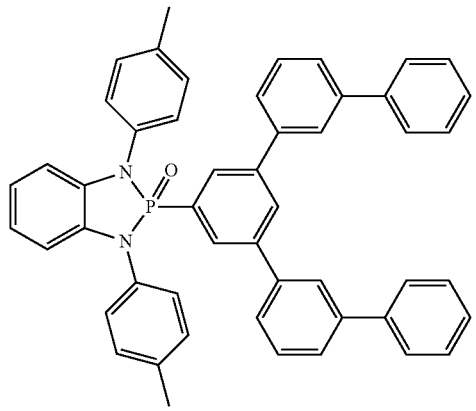
(43)
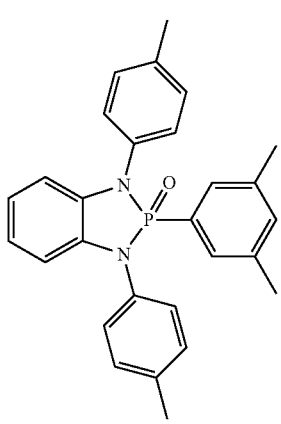
(44)
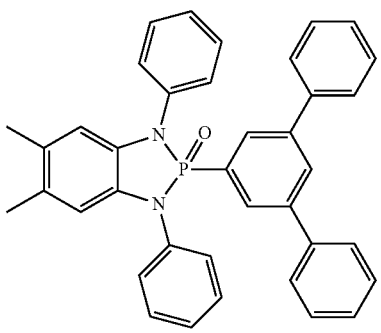
(45)
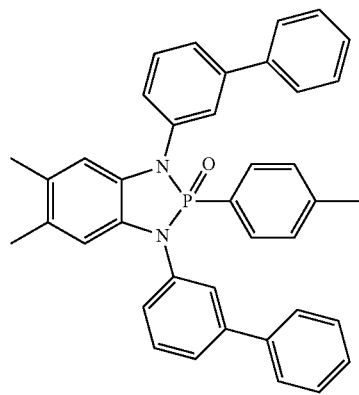

(46)
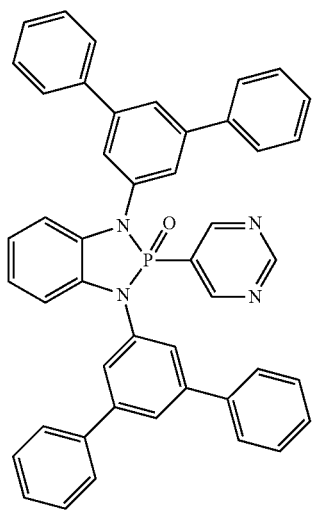
(47)
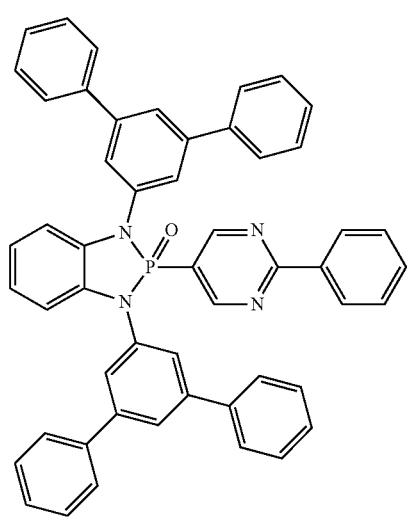
(48)
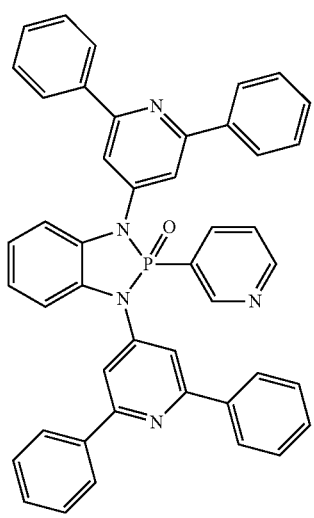
(49)
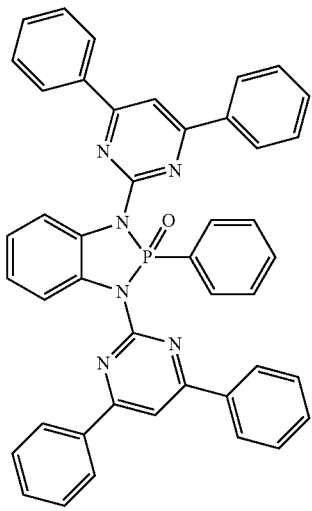
(50)
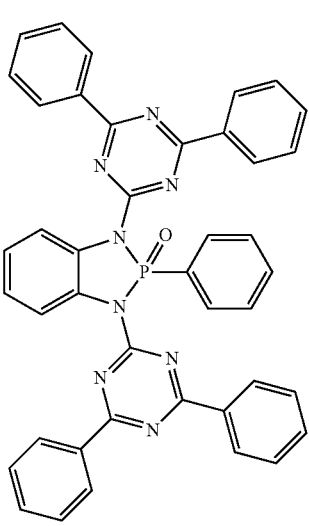
(51)
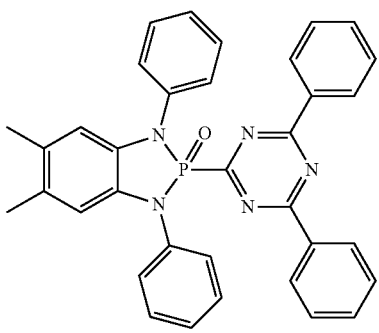

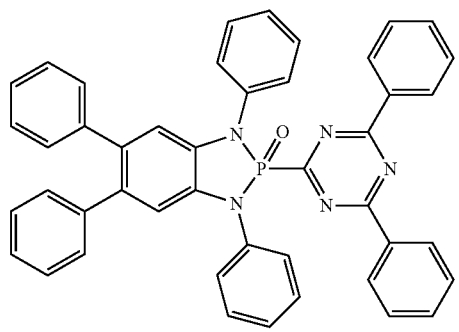
(52)
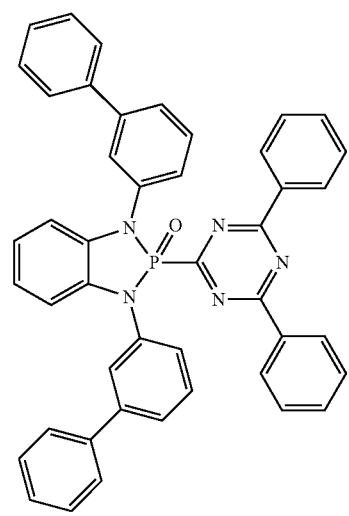
(53)
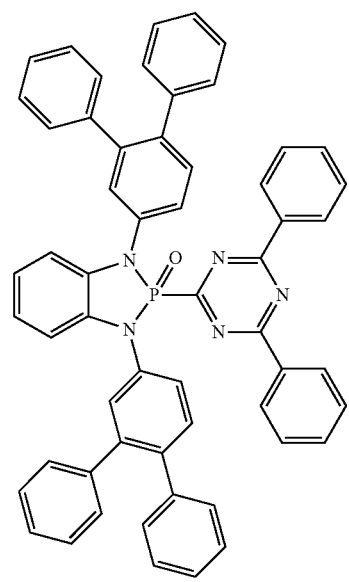
(54)
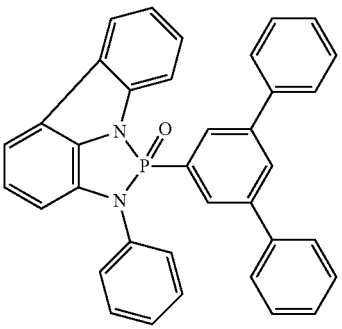
(55)
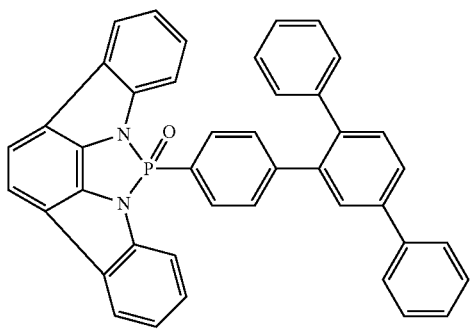
(56)
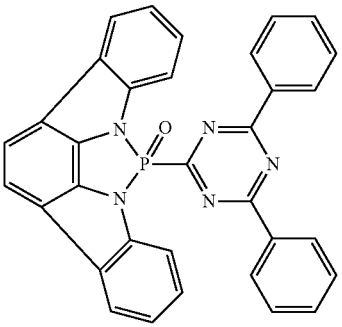
(57)
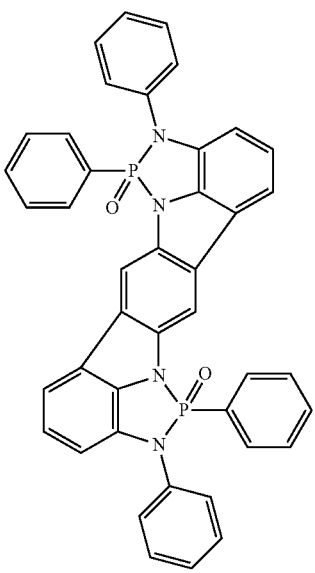
(58)

(59)
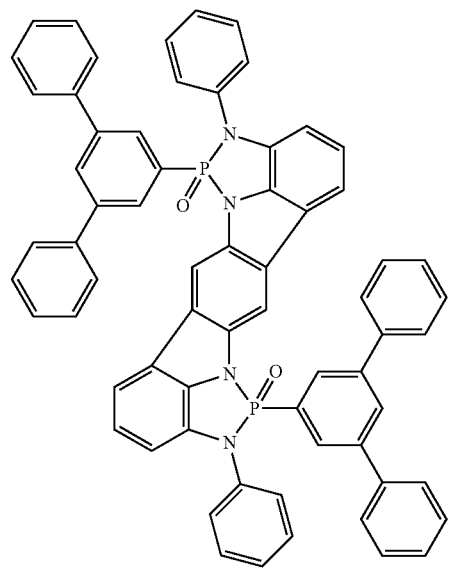
(60)
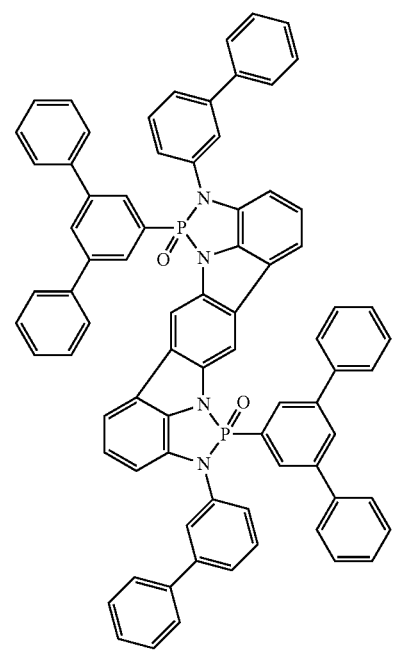
(61)
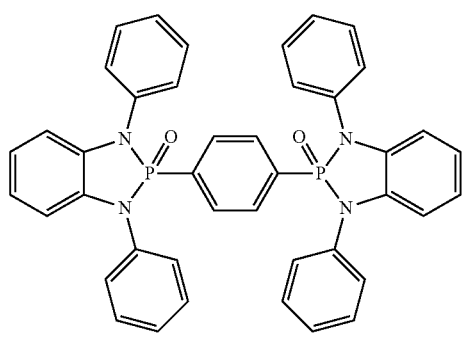
(62)
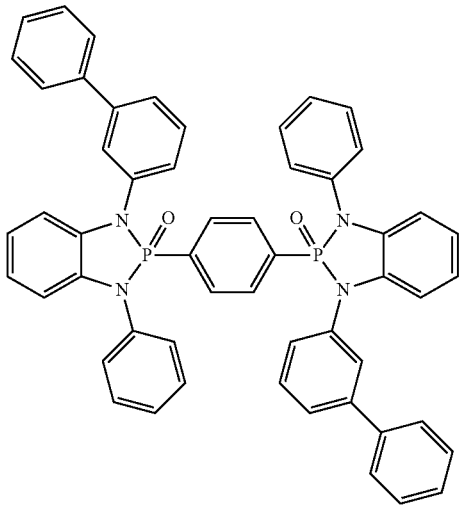
(63)
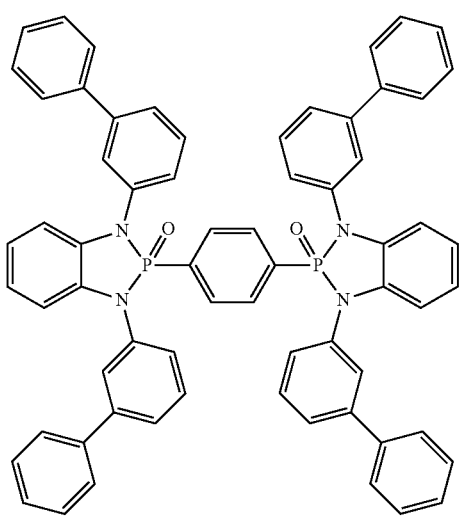
(64)
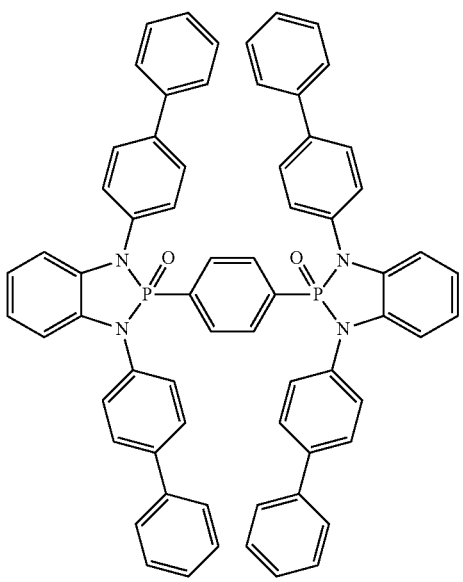

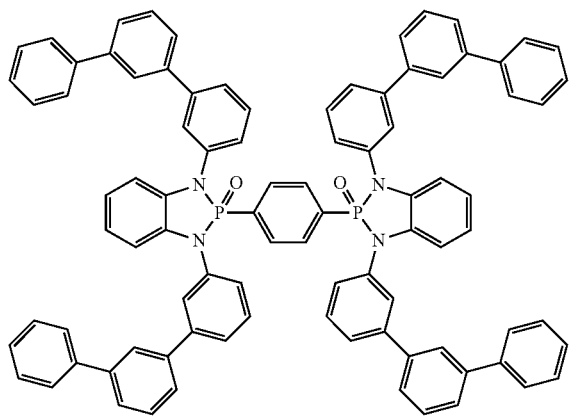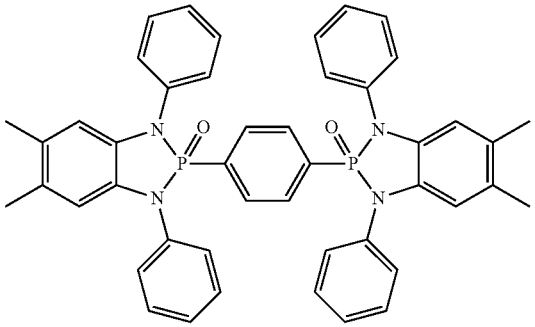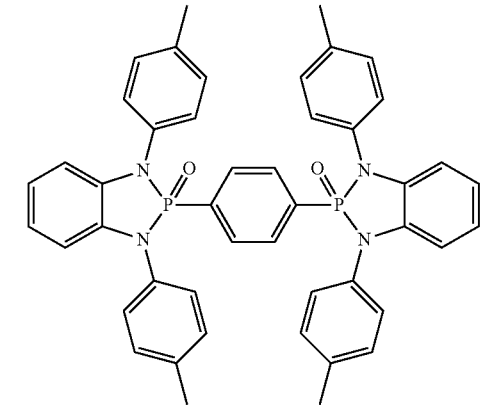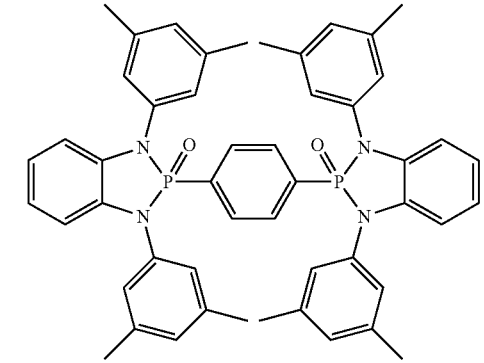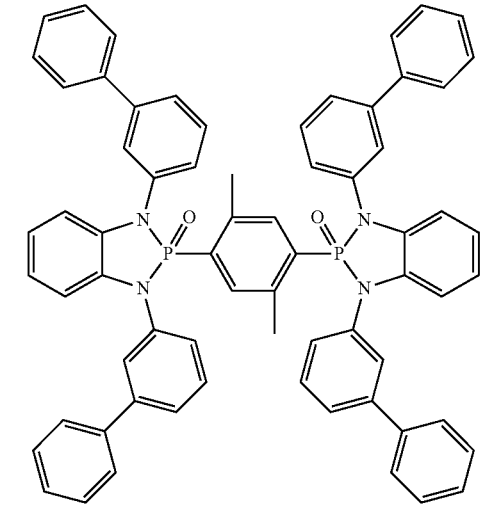

(72)
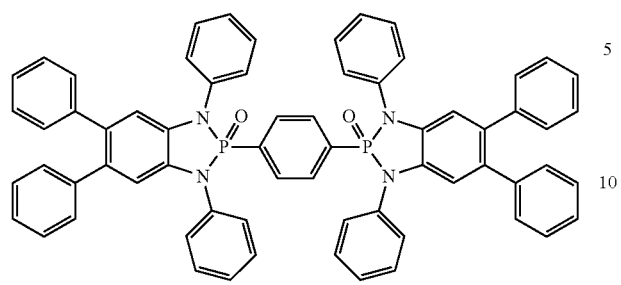
(73)
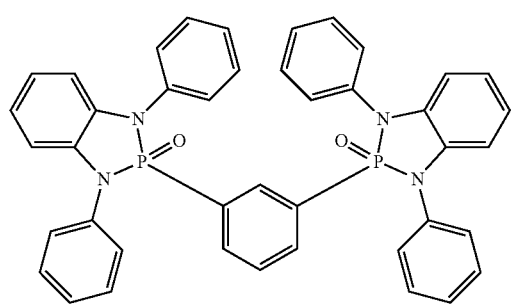
(74)
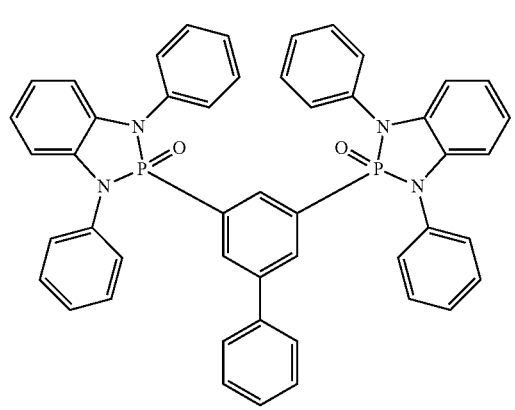
(75)
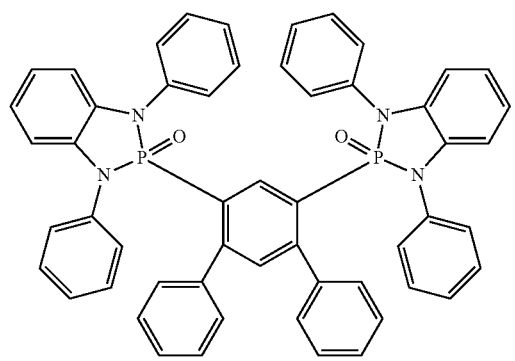
(76)
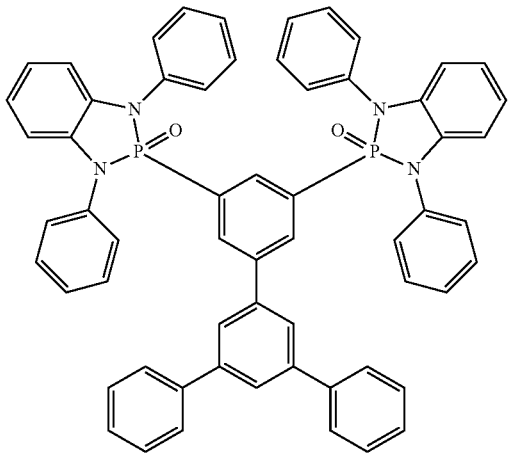
(77)
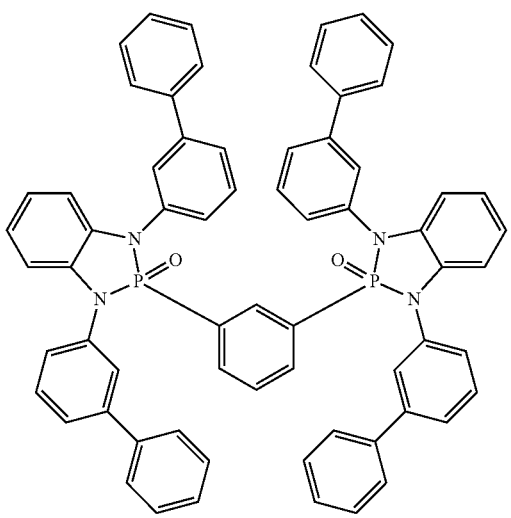
(78)
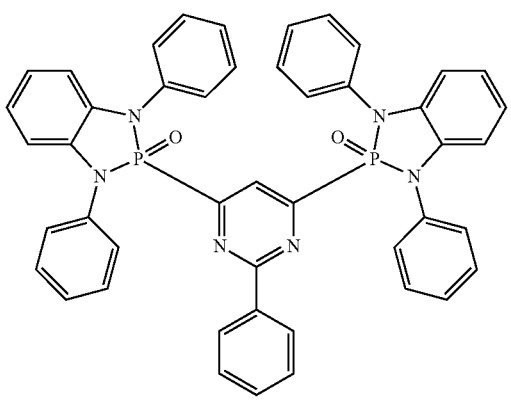

-continued
(79)
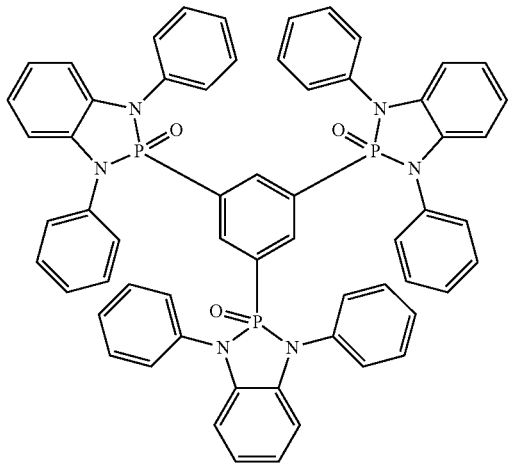
(80)
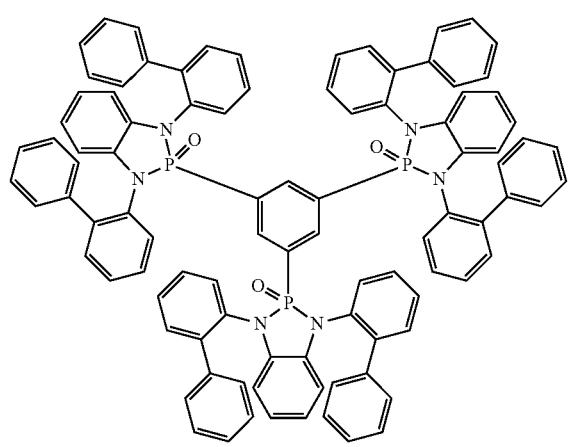
(81)
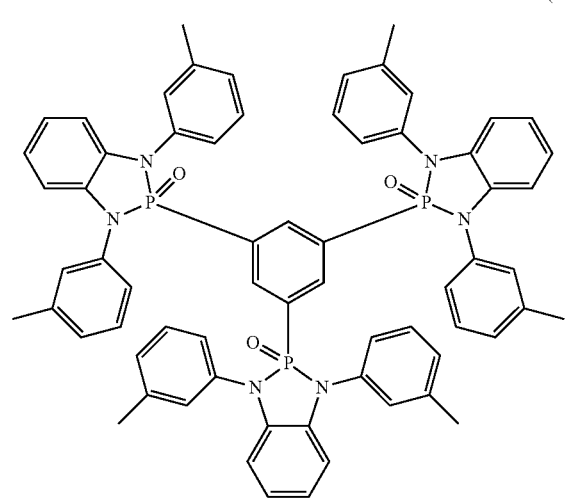
-continued
(82)
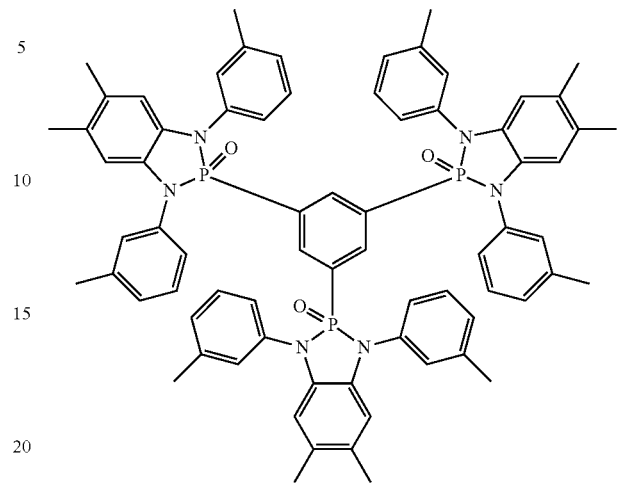
(83)
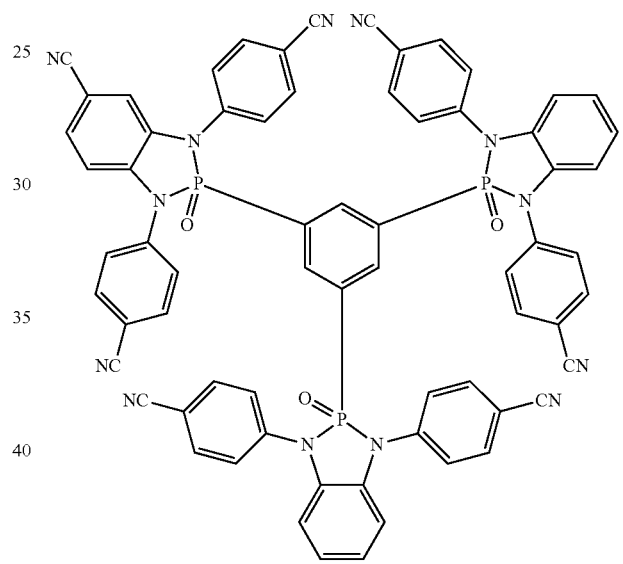
(84)
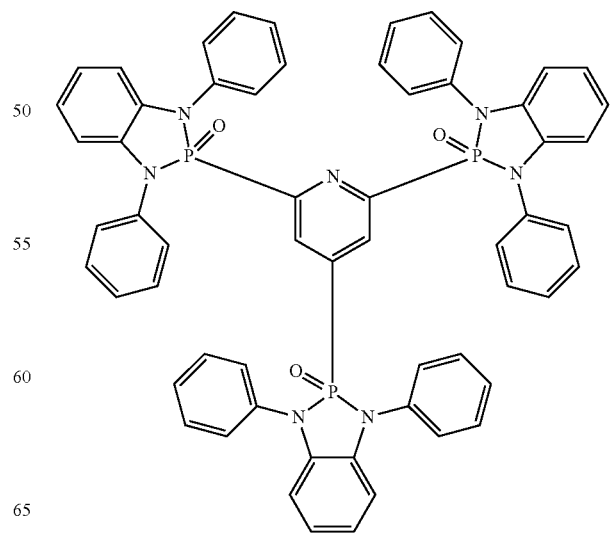

(85)
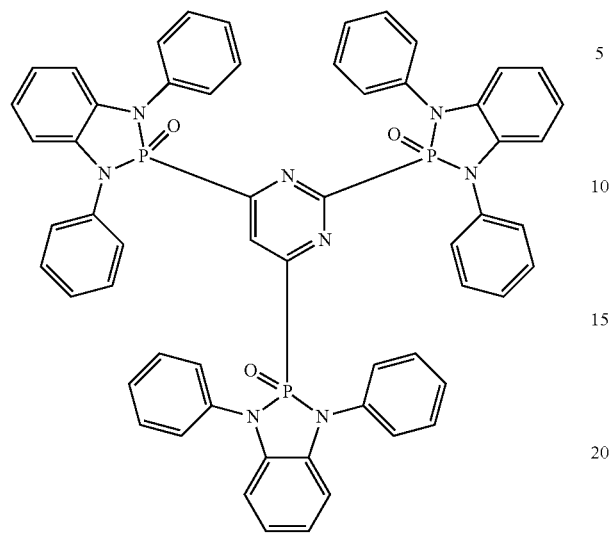
(87)
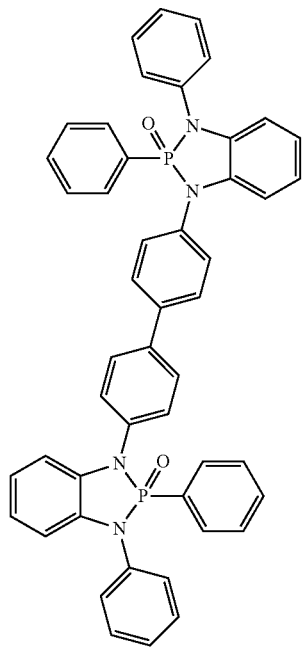
(86)
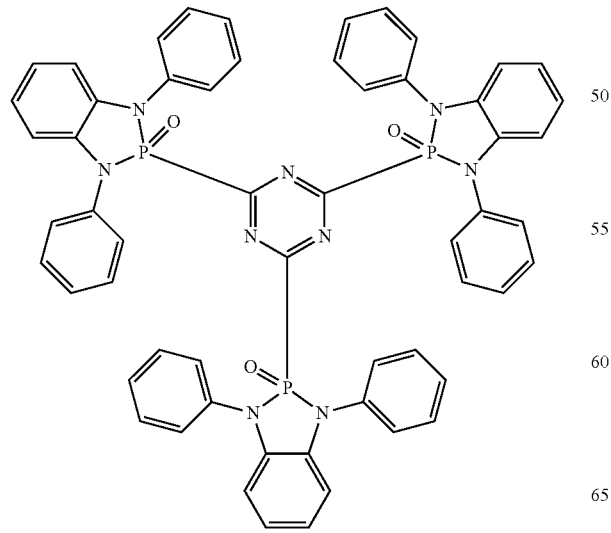
(88)
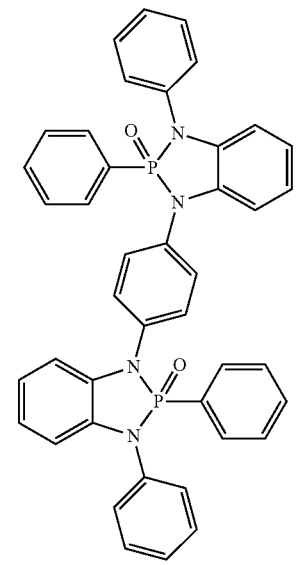

(89)
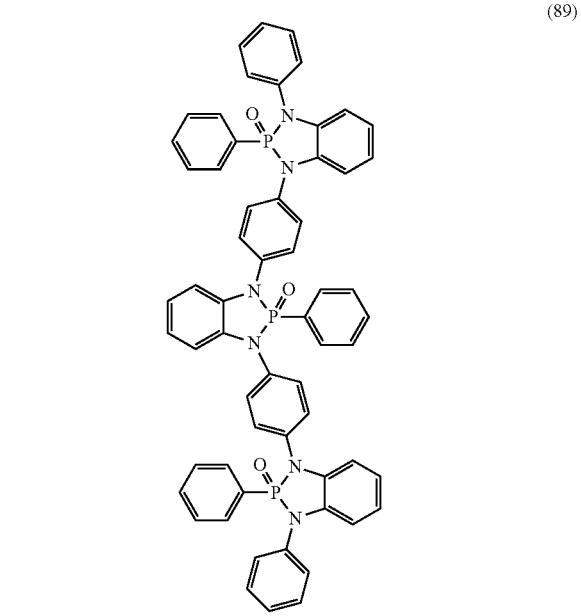
(92)
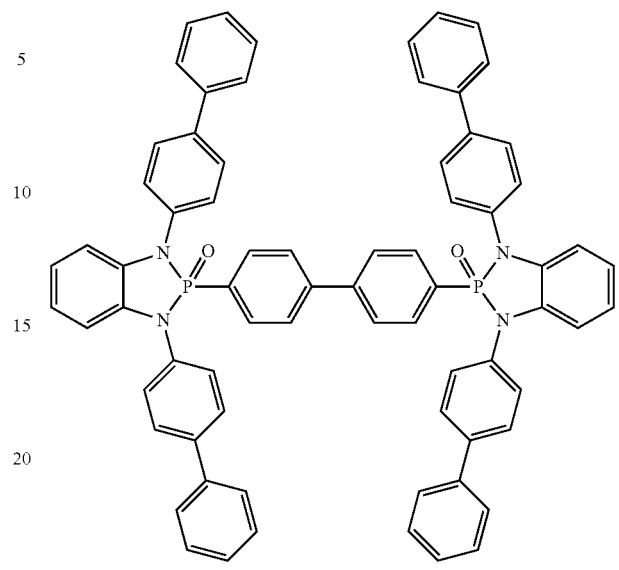
(90)
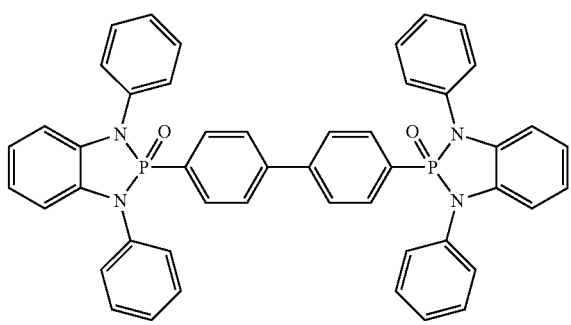
(93)
(94)
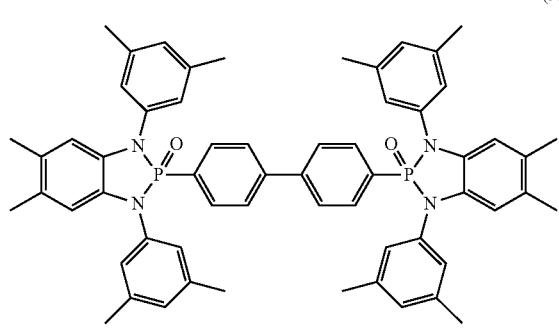
(91)
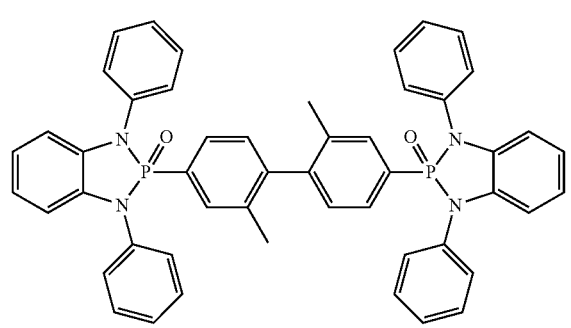
(95)

-continued
(96)
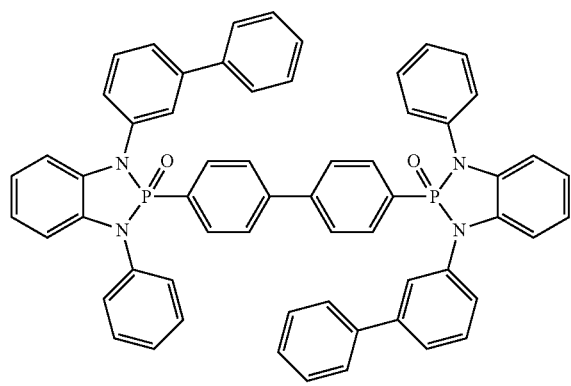
(97)
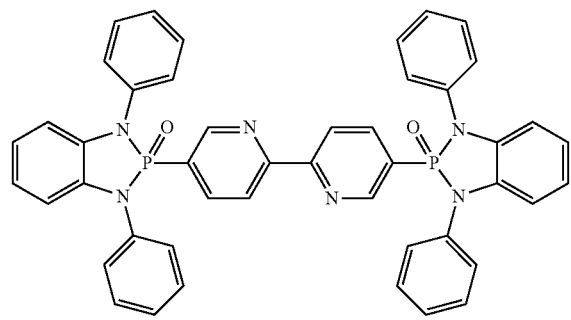
(98)
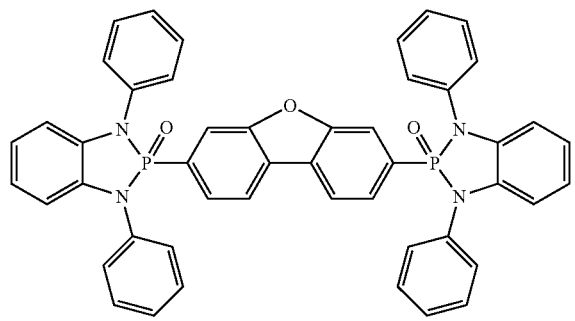
(99)
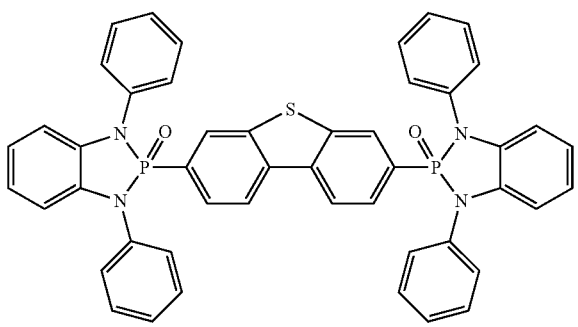
-continued
(100)
(101)
(102)
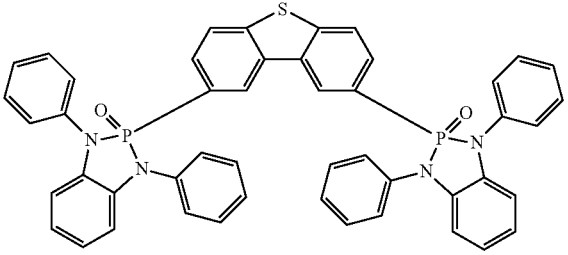
(103)
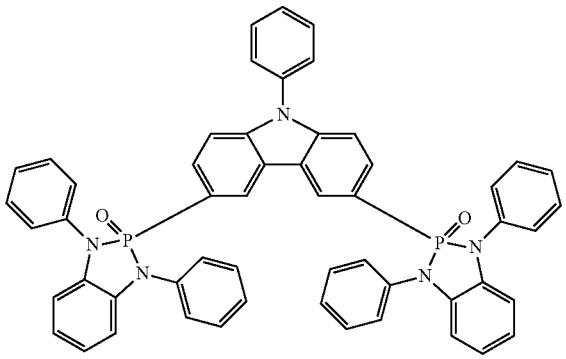

(104)
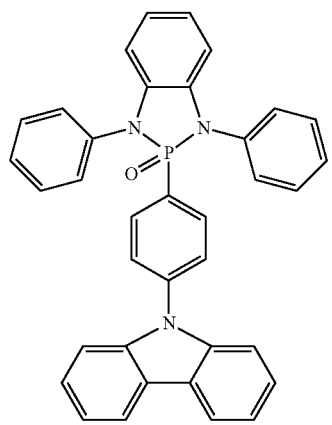
(105)
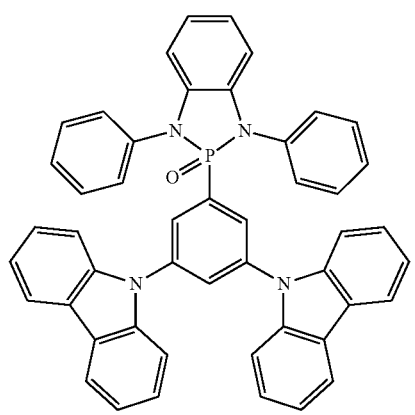
(106)
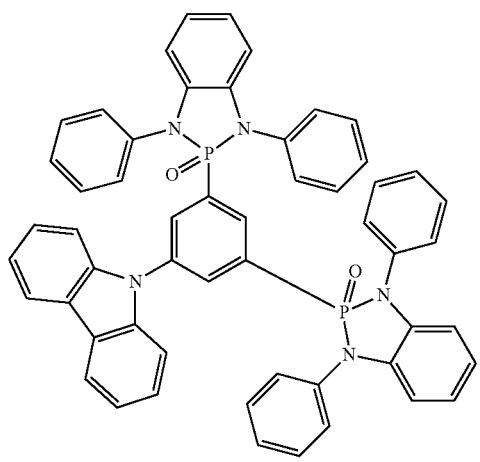
(107)
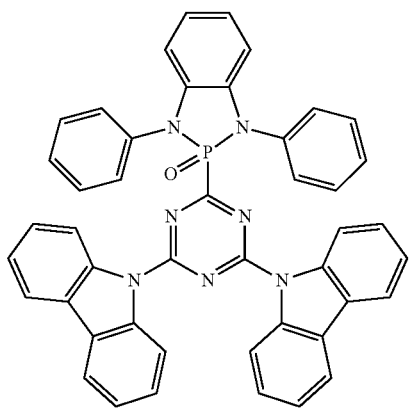
(108)
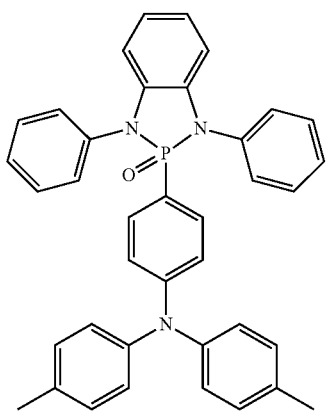
(109)
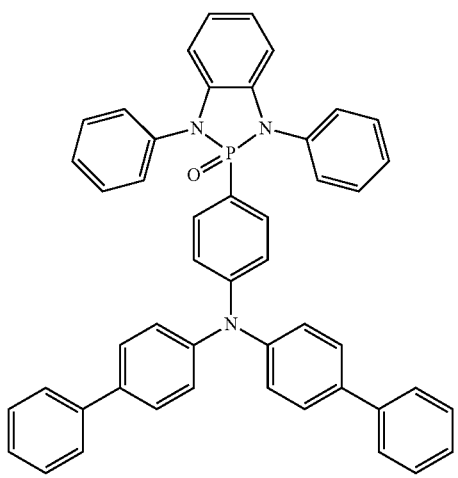

(110)
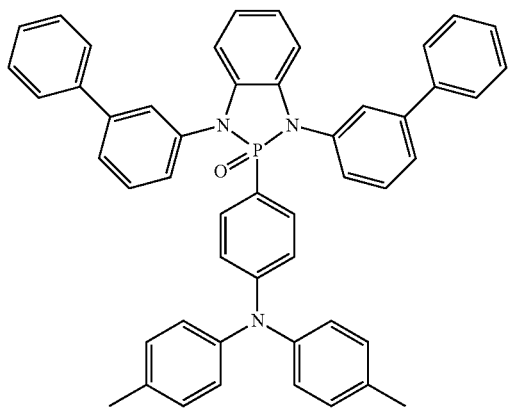
(111)
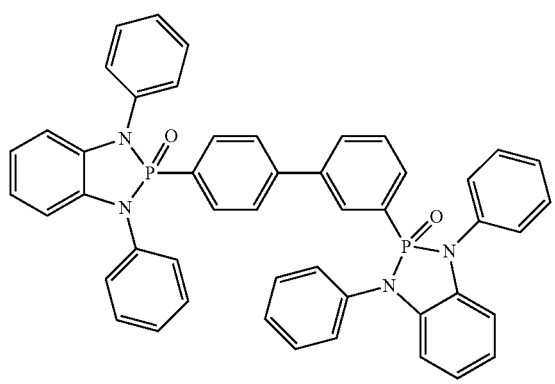
(113)
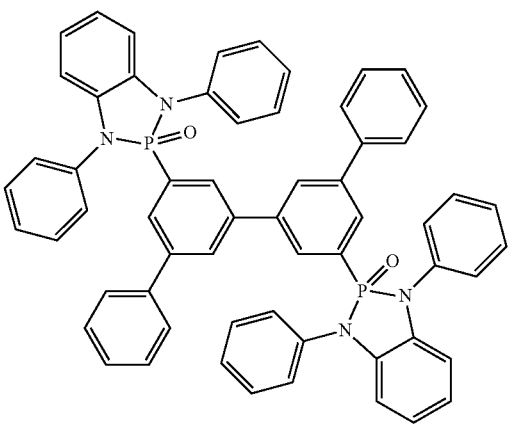
(114)
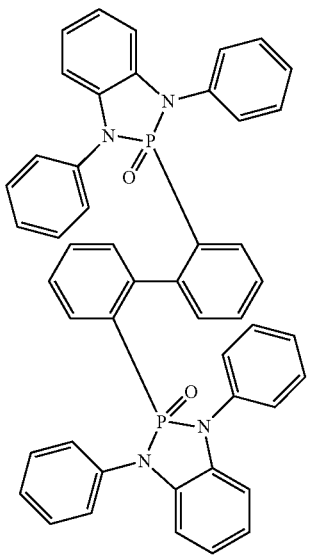
(112)
(115)
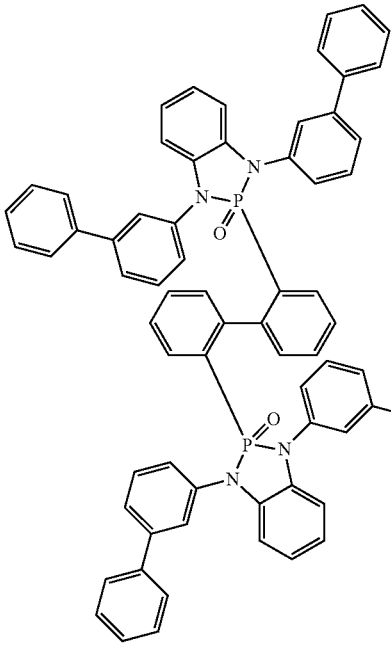

(116)
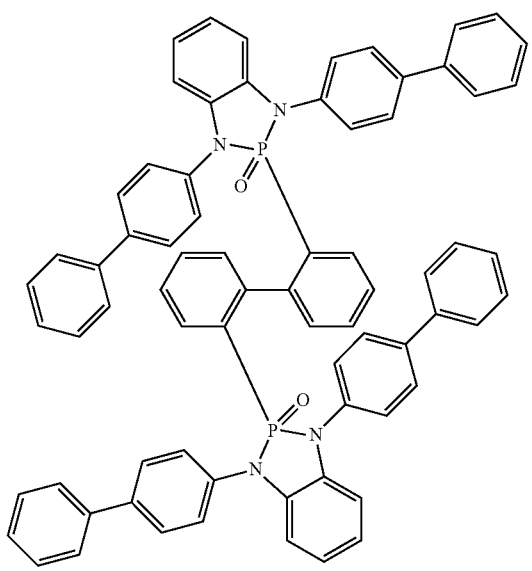
(117)
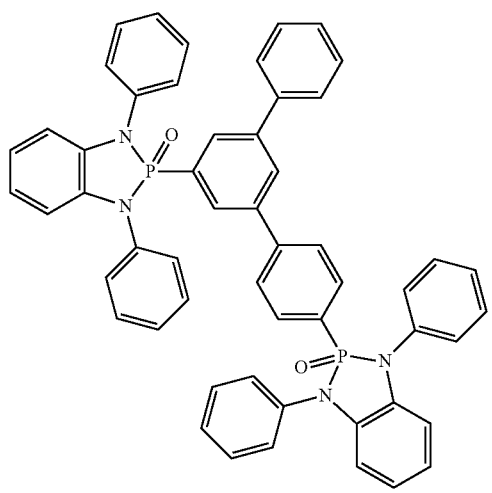
(118)
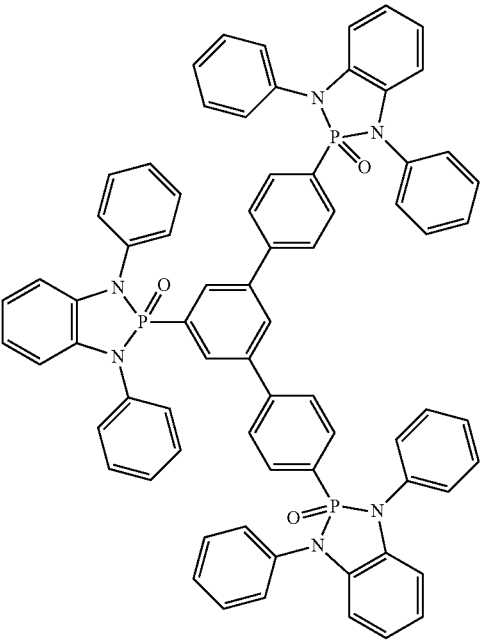
(119)
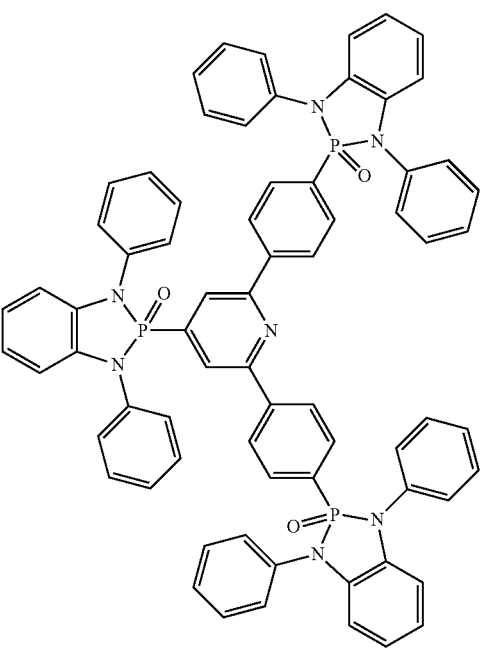

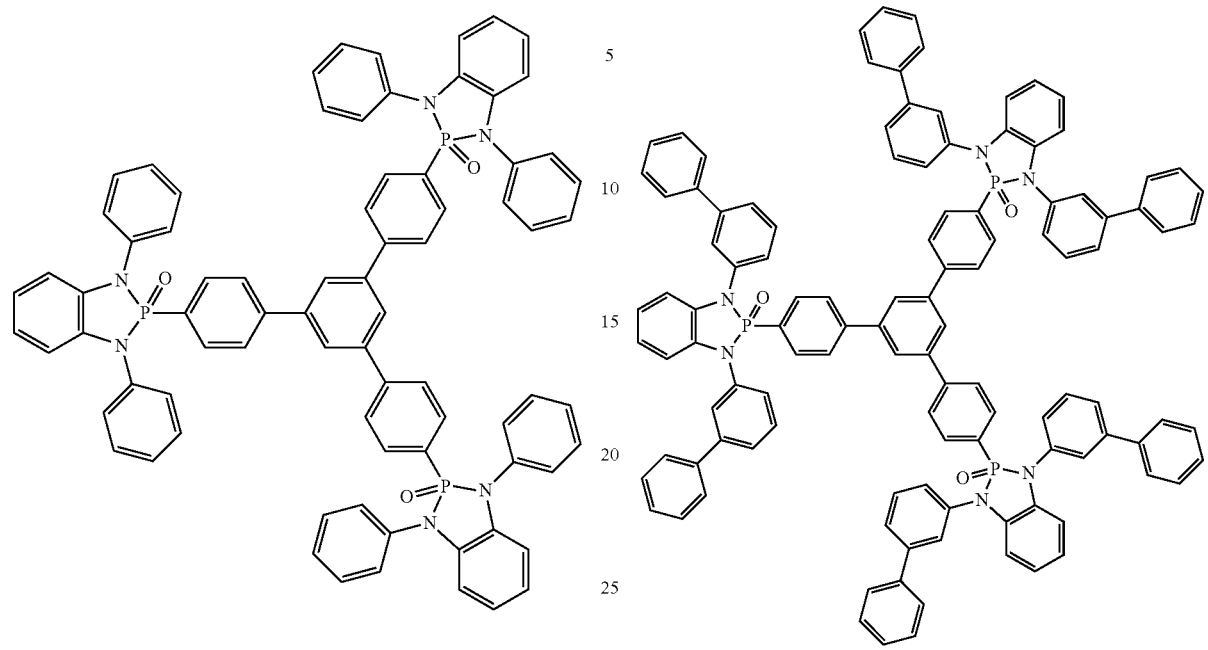
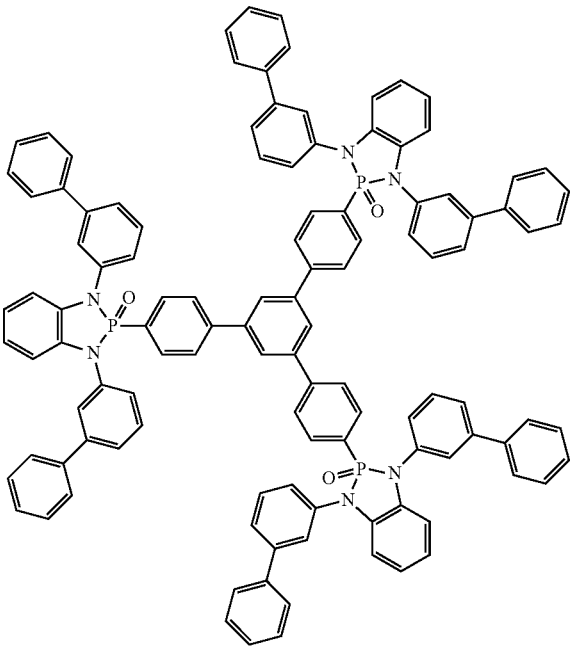
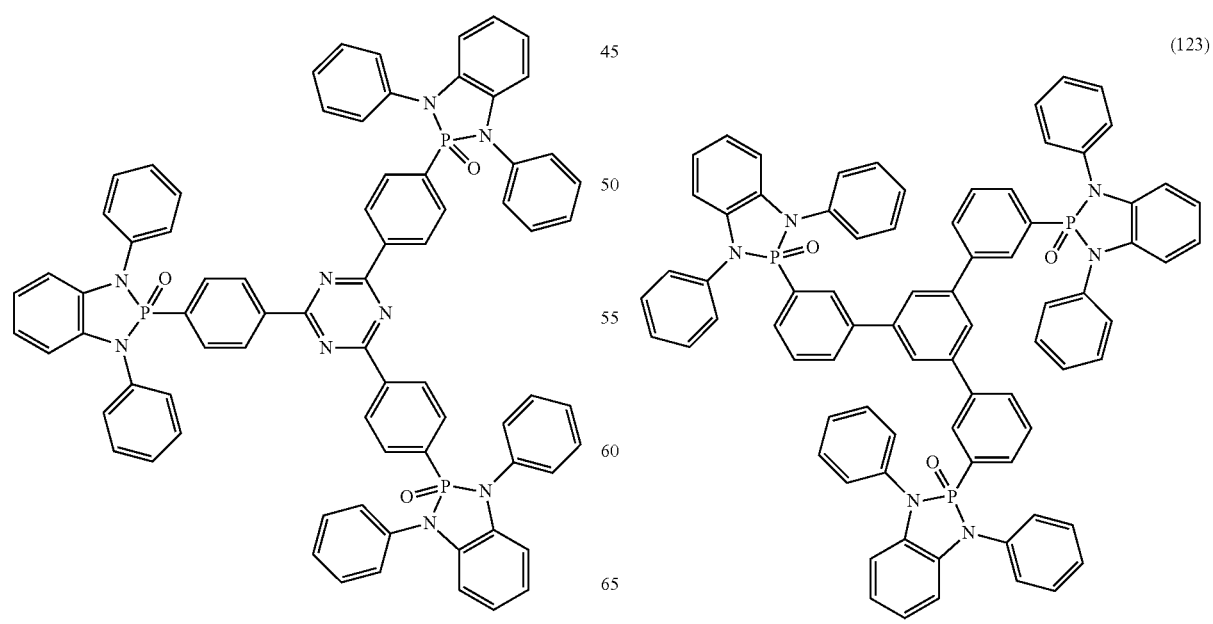

(124)
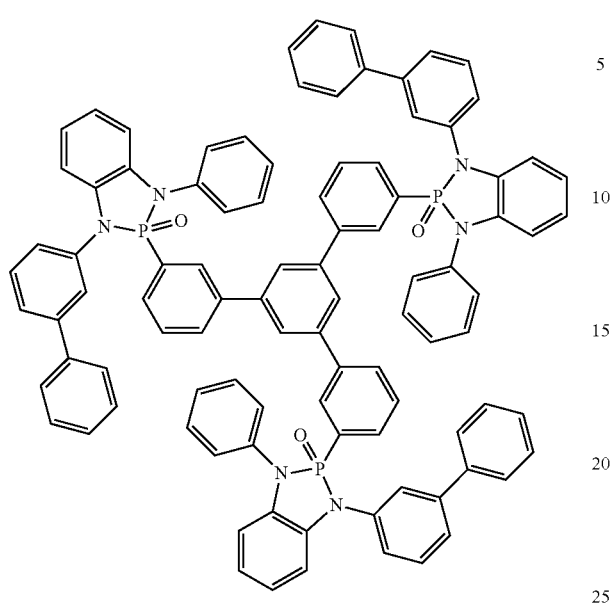
(125)
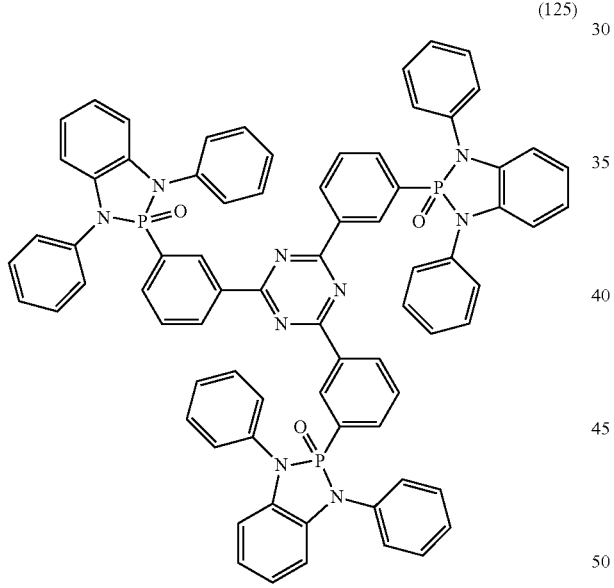
(126)
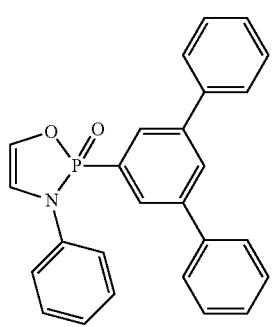
(127)
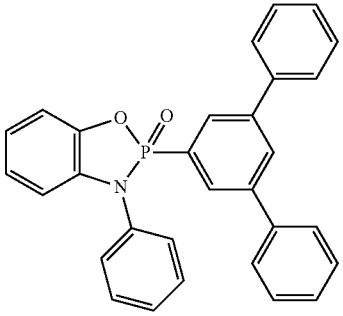
(128)
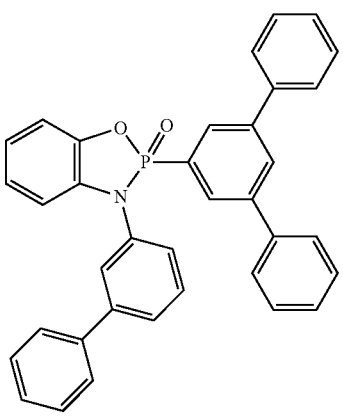
(129)
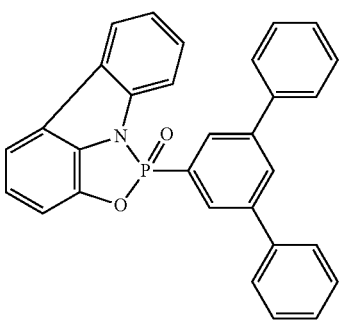
(130)
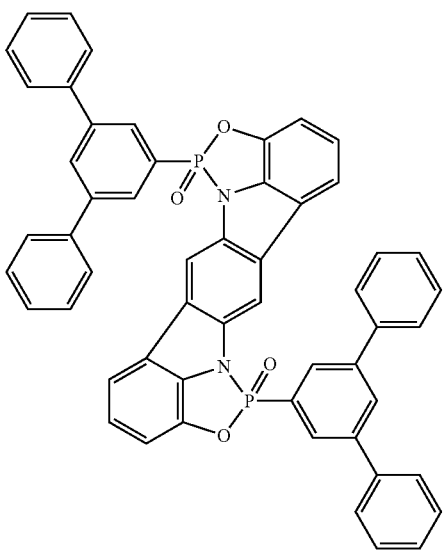

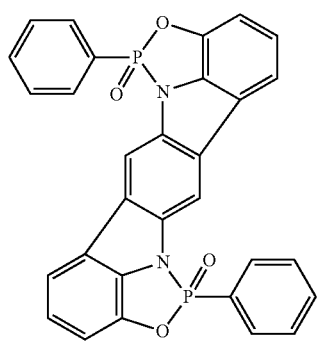
(131)
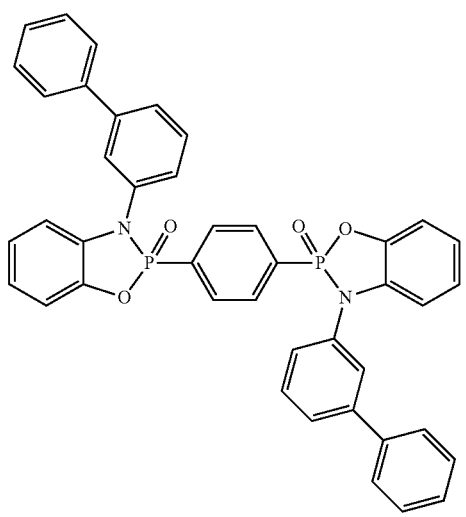
(132)
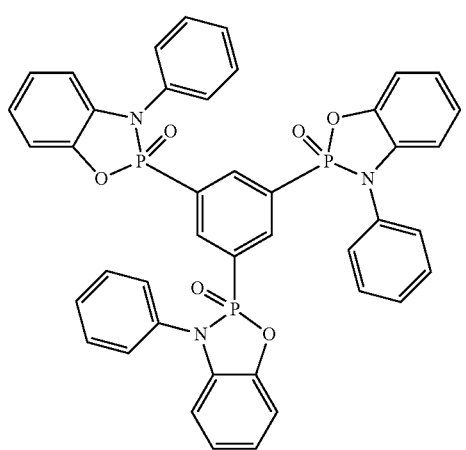
(133)
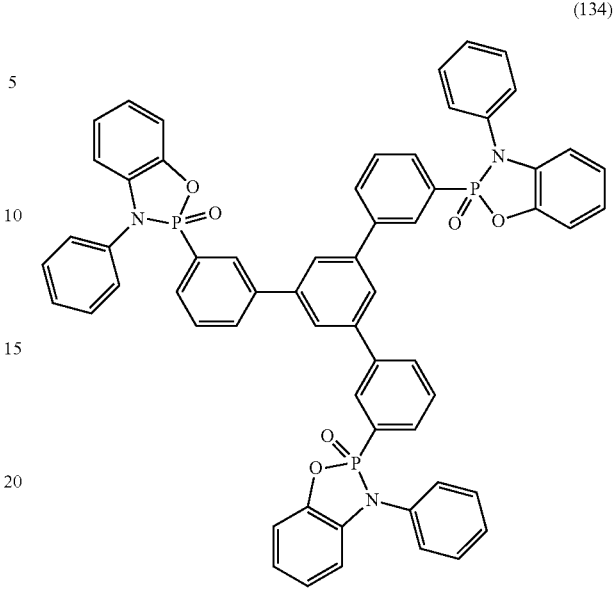
(134)
(135)
(136)
(137)

(138)
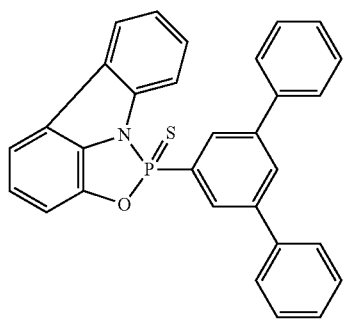
(141)
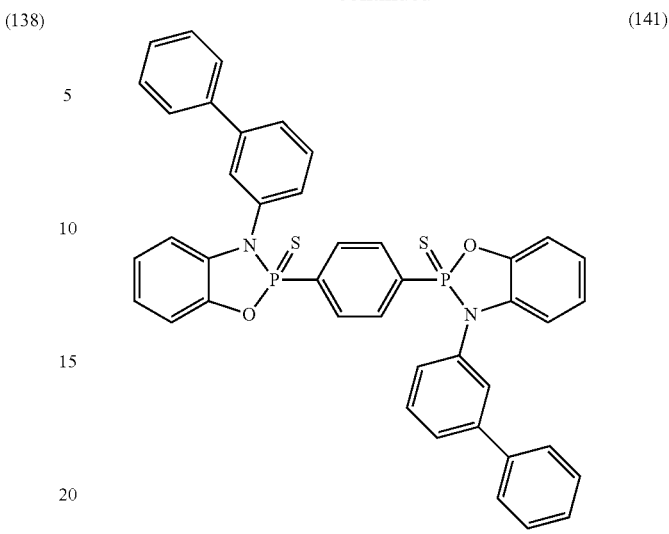
(139)
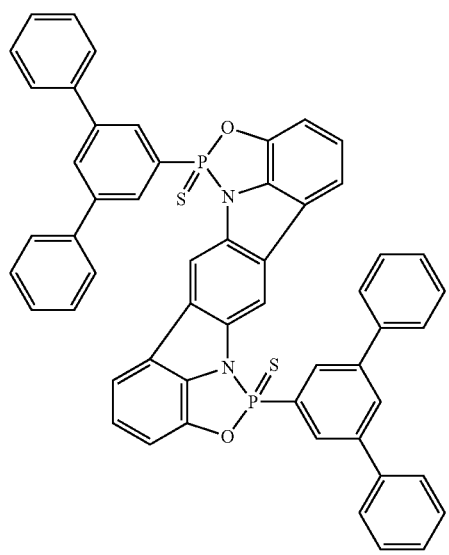
(142)
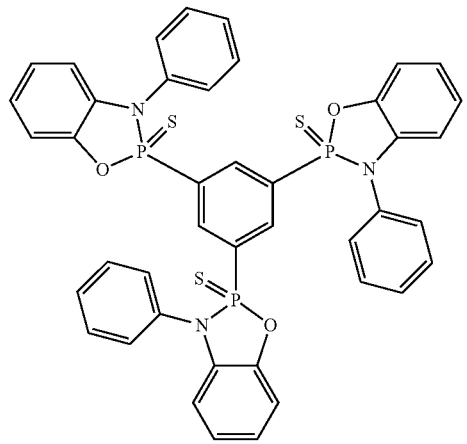
(140)
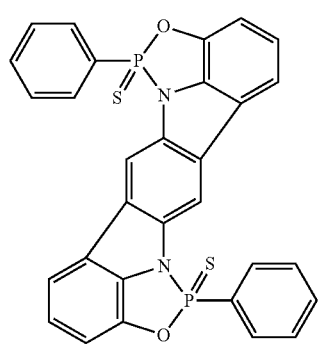
(143)
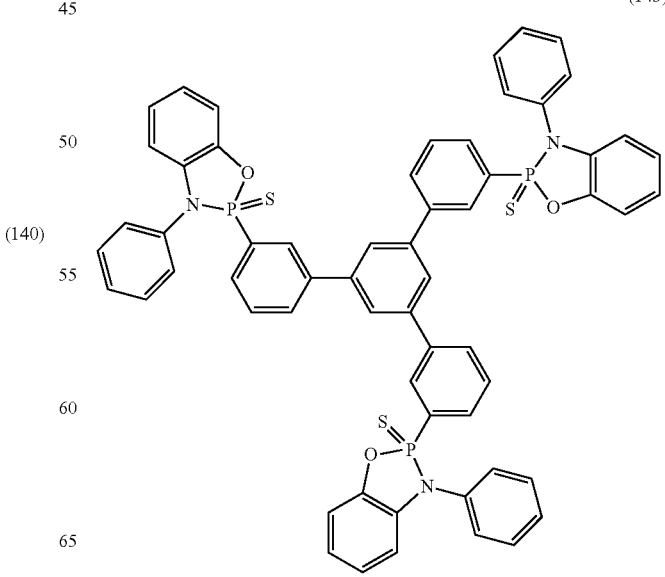

-continued
(144)
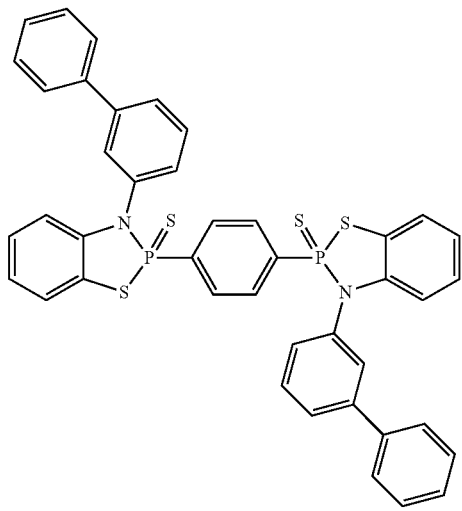
(145)
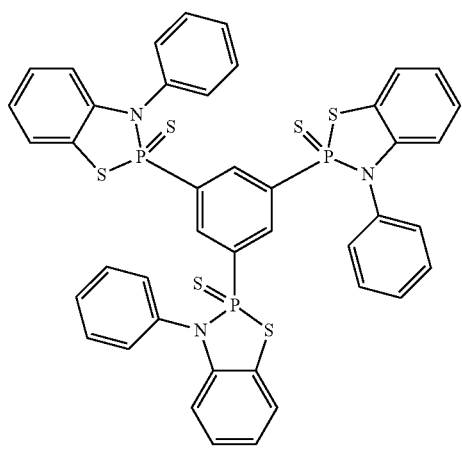
(146)
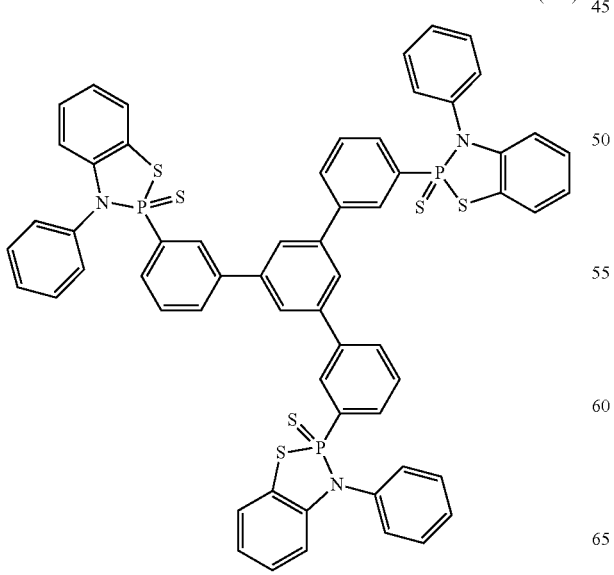
-continued
(147)
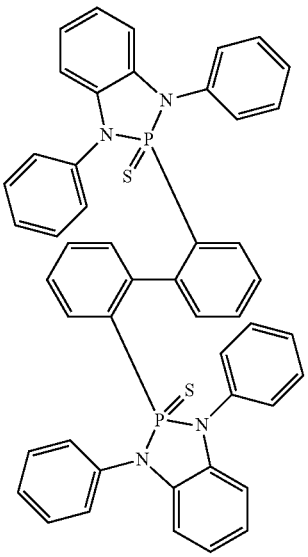
(148)
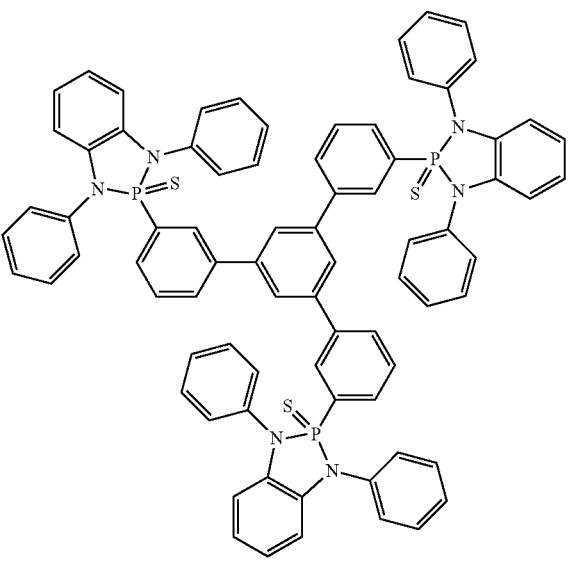
(149)
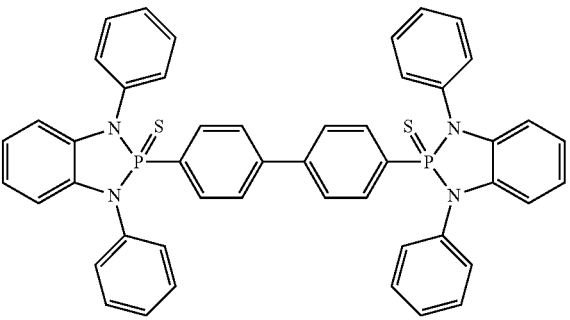

(150)
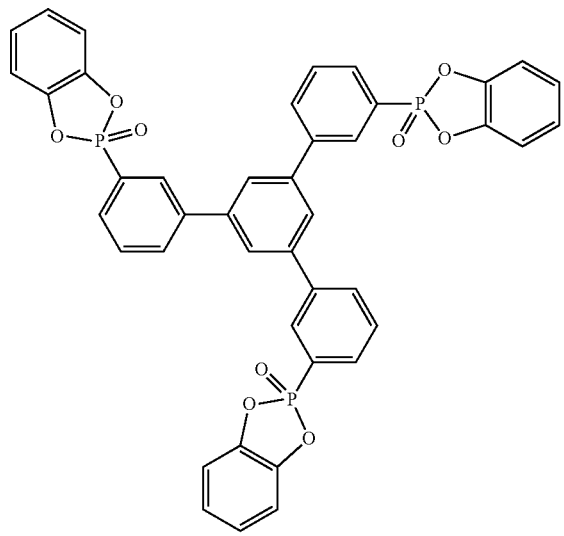
(151)
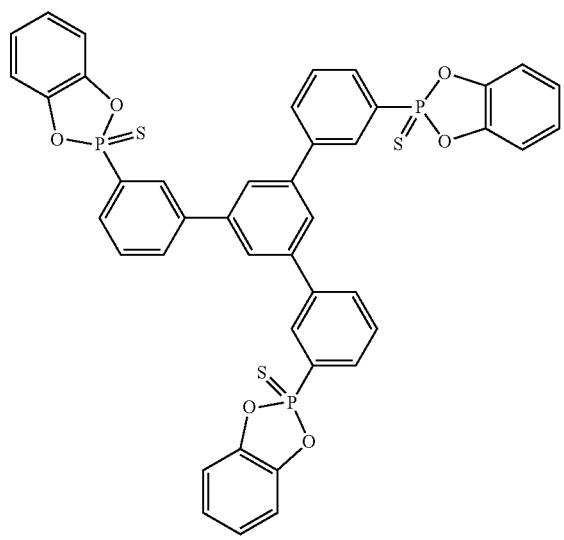
(152)
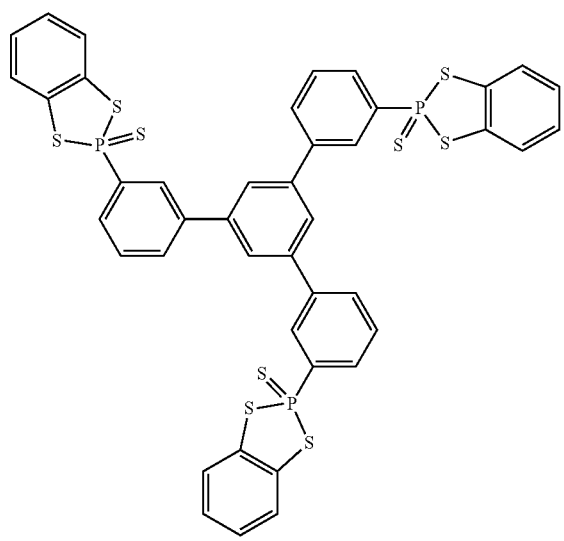
(153)
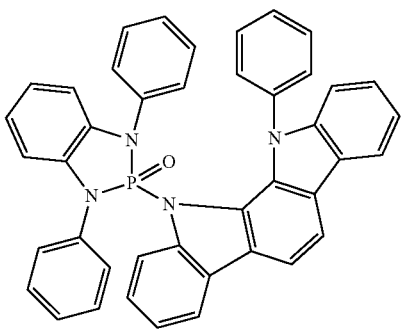
(154)
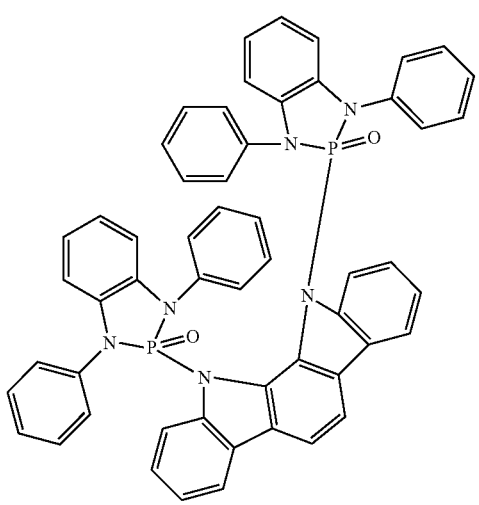
(155)
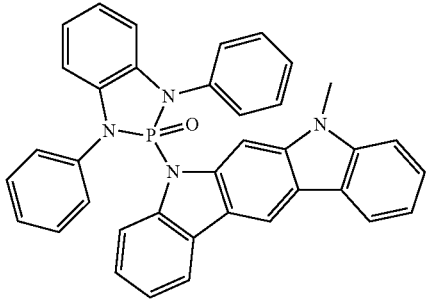
(156)
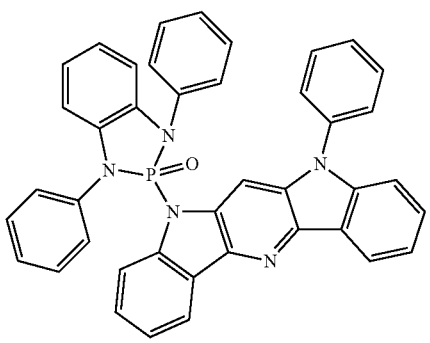

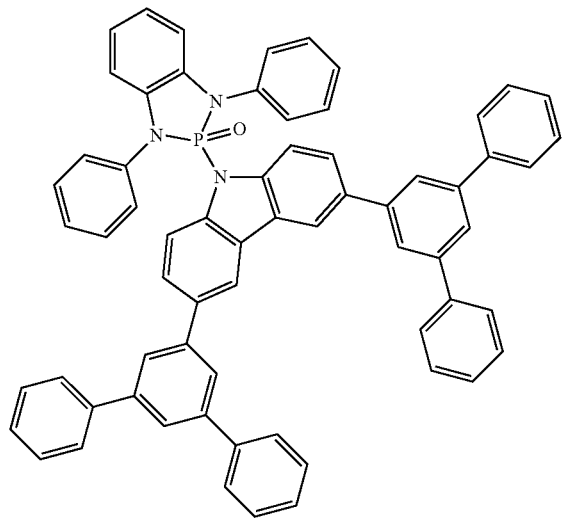
(157)
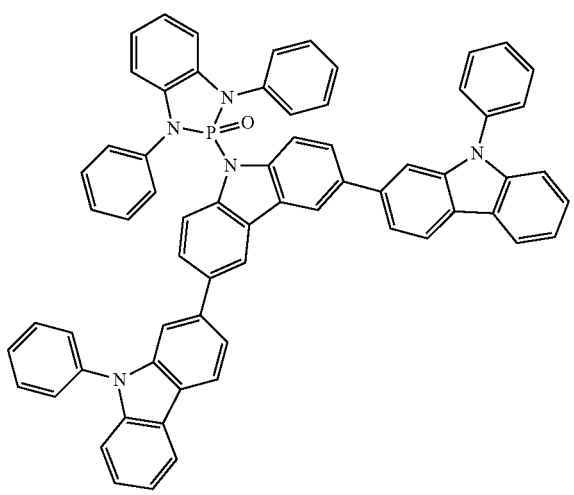
(158)
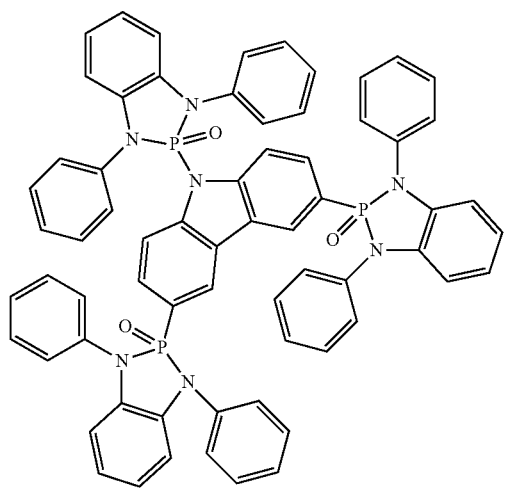
(159)
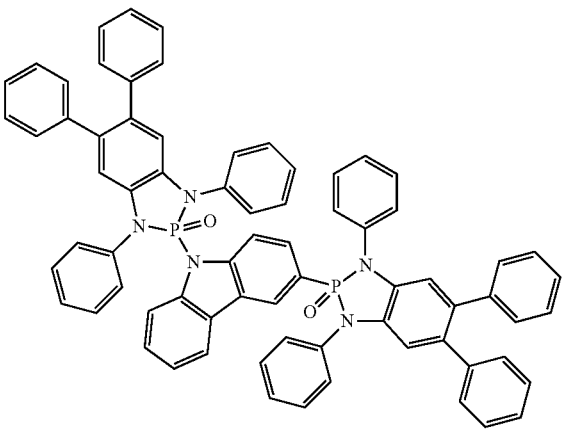
(160)
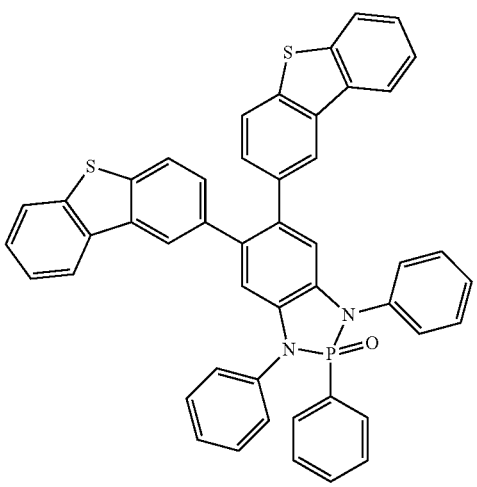
(161)
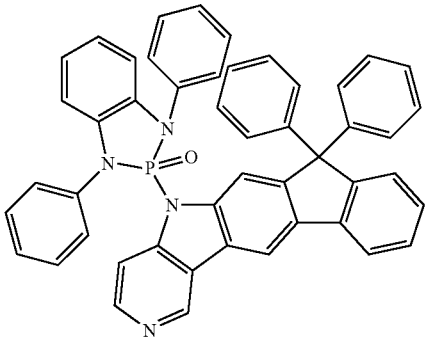
(162)
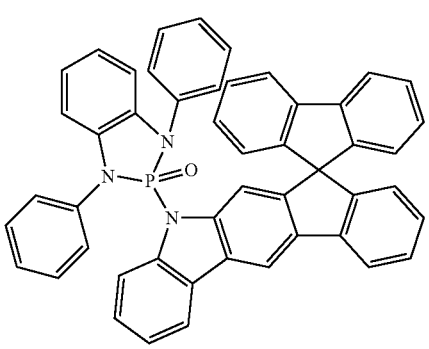
(163)

-continued
(164)
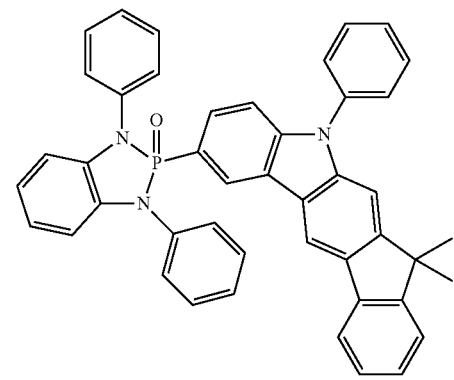
(165)
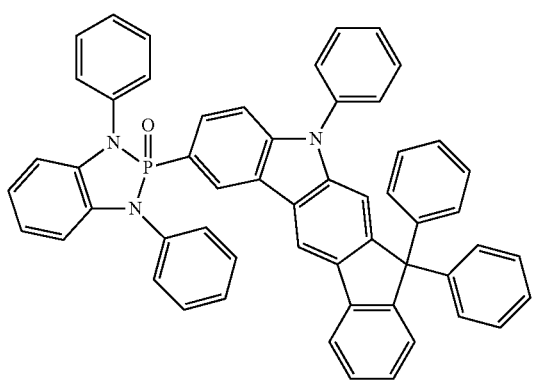
(166)
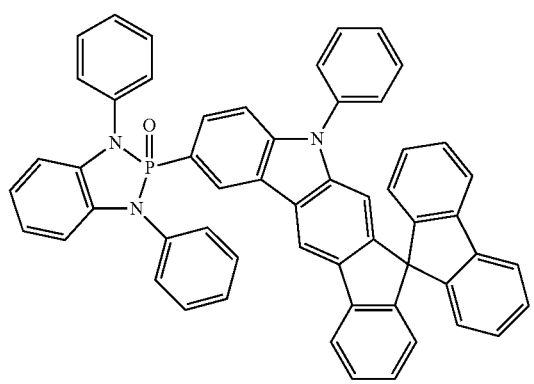
(167)
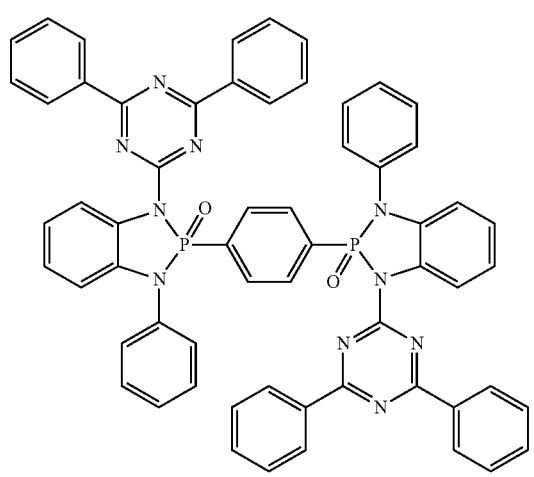
-continued
(168)
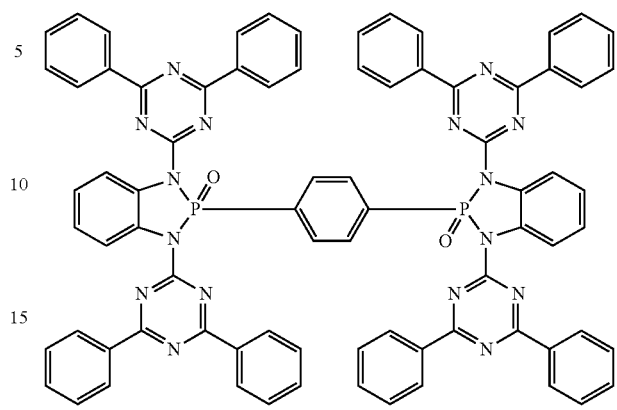
(169)
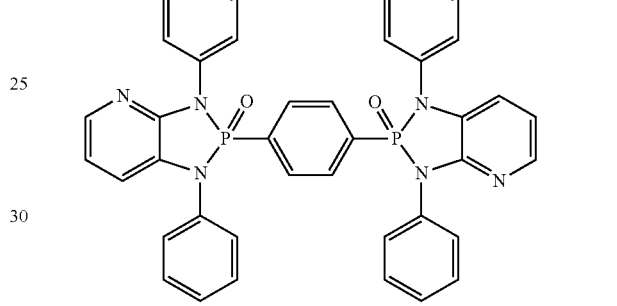
(170)
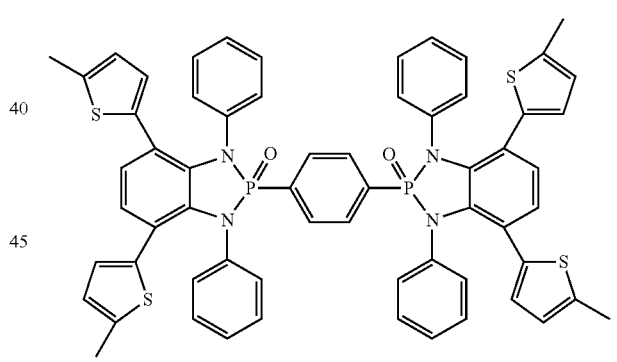
(171)
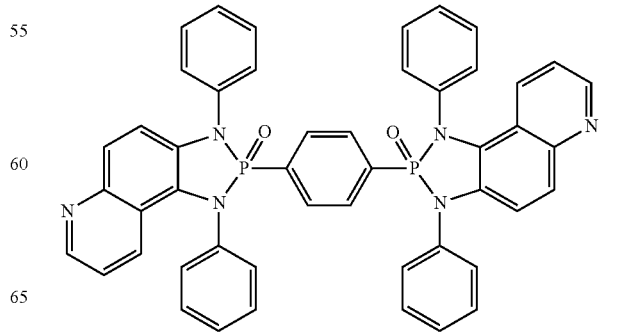

-continued
(172)
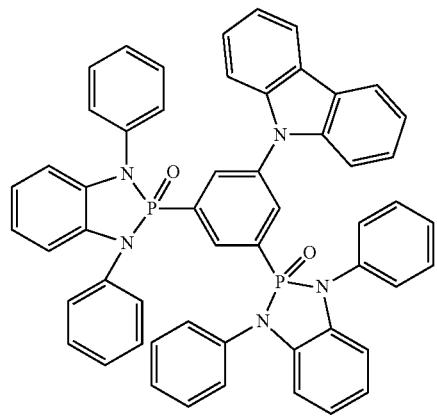
(173)
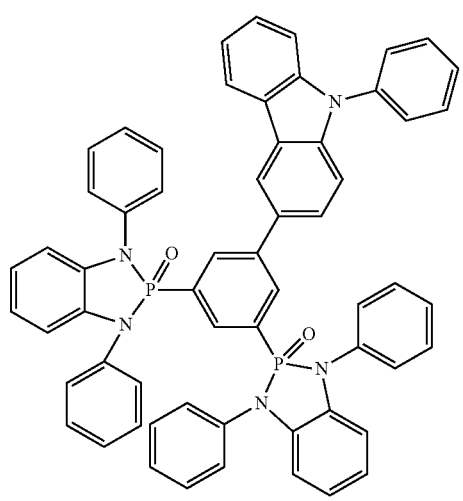
(174)
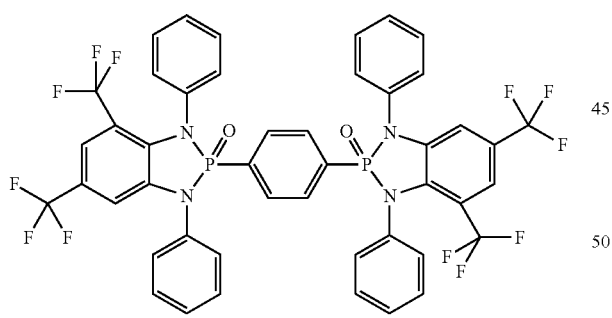
(175)
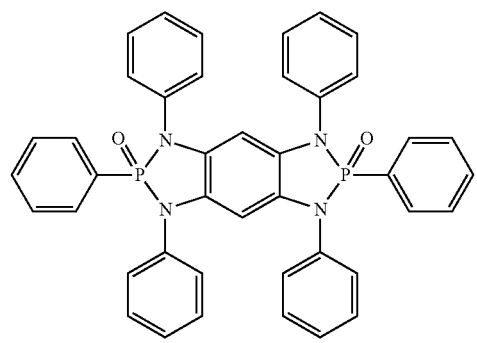
-continued
(176)
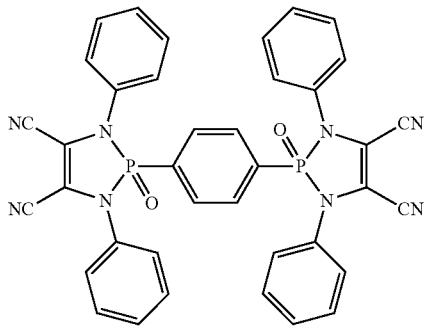
(177)
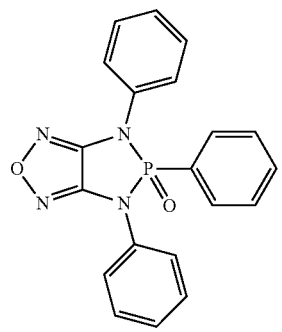
(178)
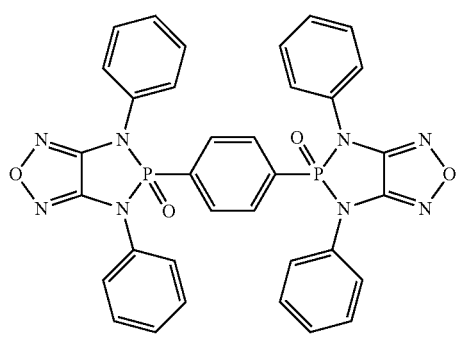
(179)
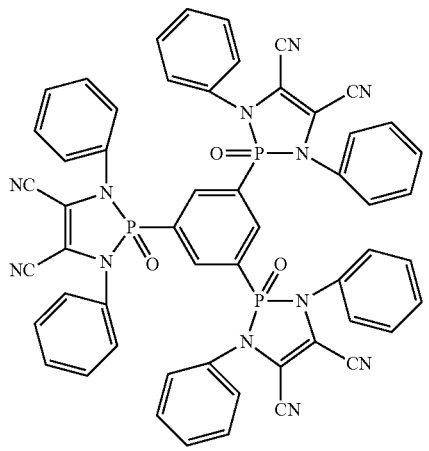

(180)
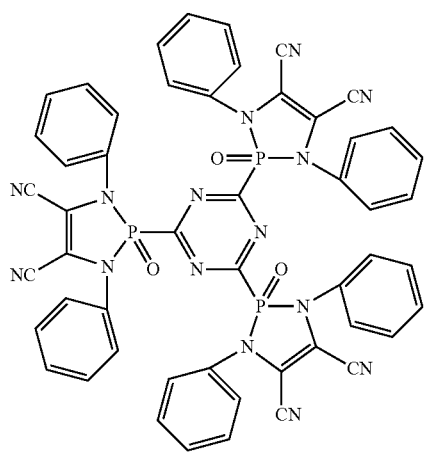
(181)
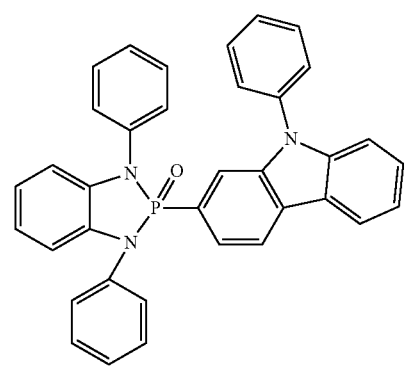
(182)
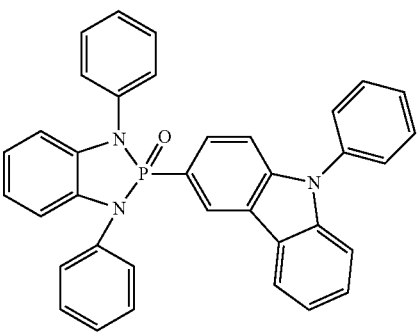
(182)
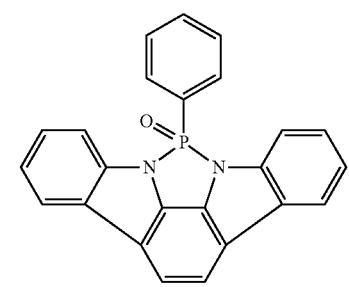
(183)
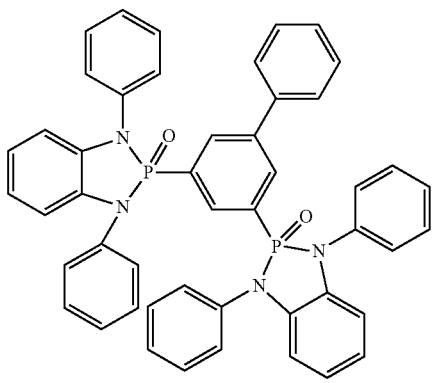
(184)
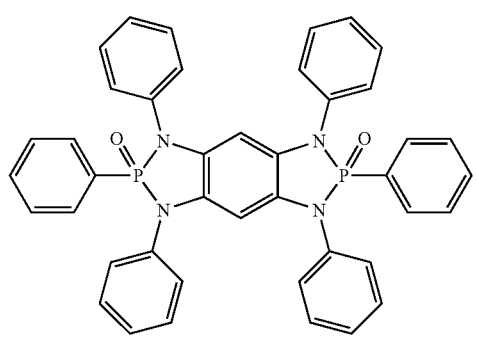
(185)
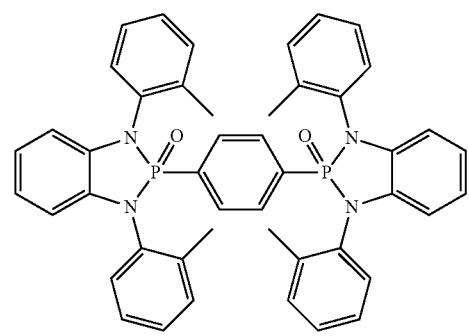
(186)
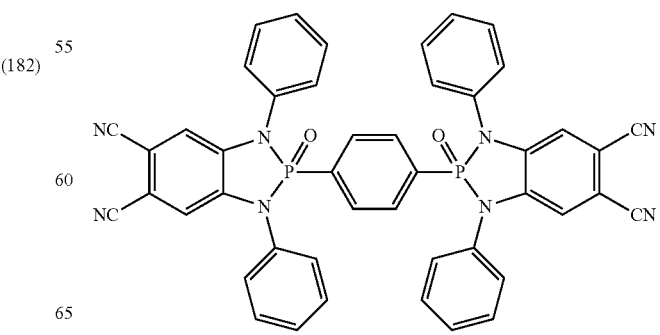

-continued
(187)
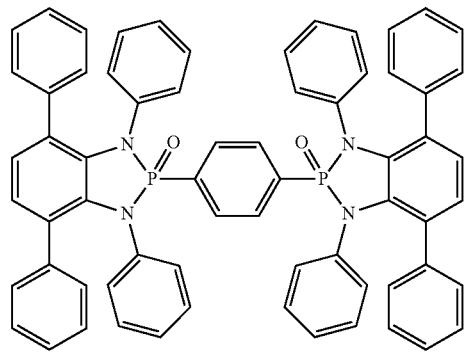
(188)
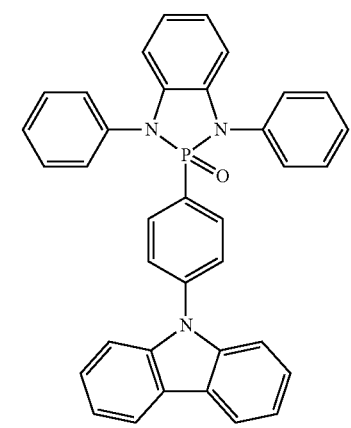
(189)
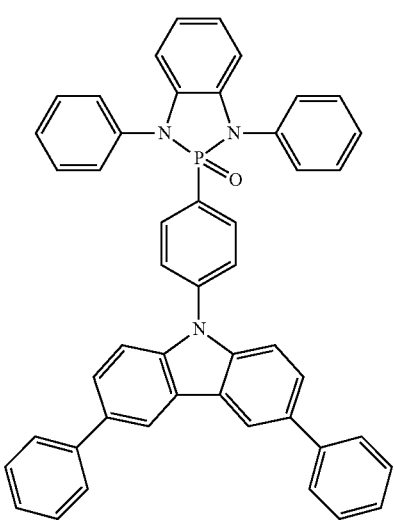
-continued
(190)
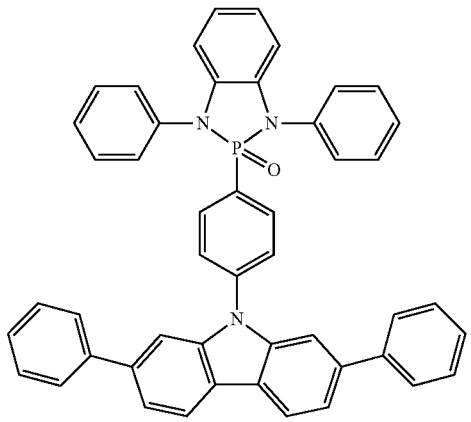
(191)
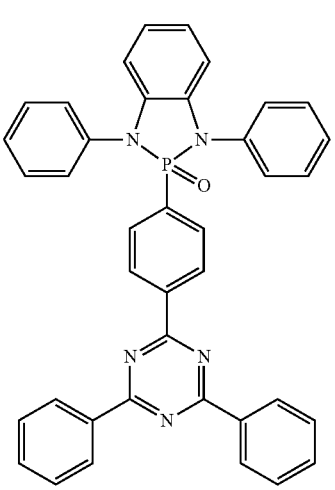
(192)
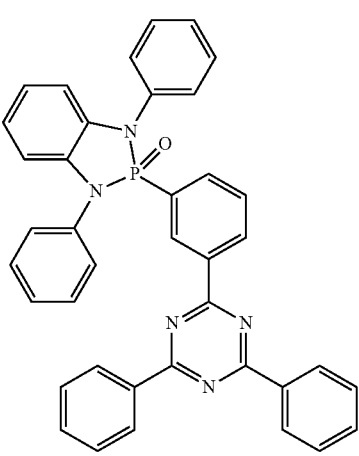

-continued
(193)
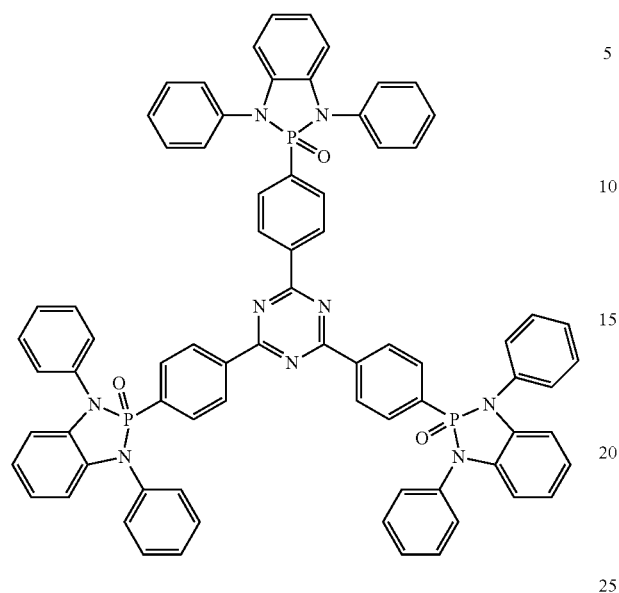
(194)
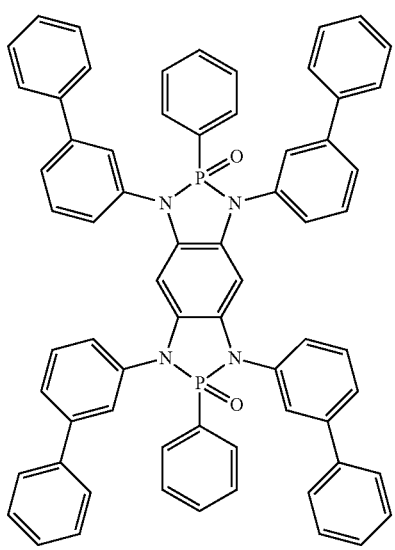
-continued
(195)
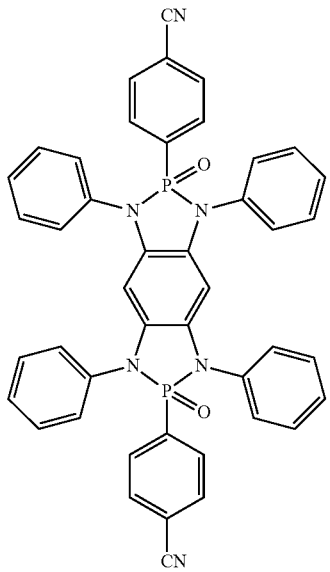
(196)
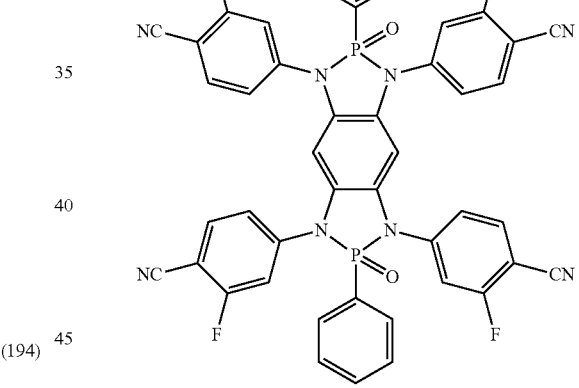
(197)
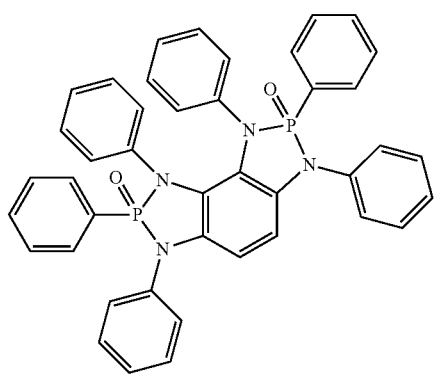

(198)
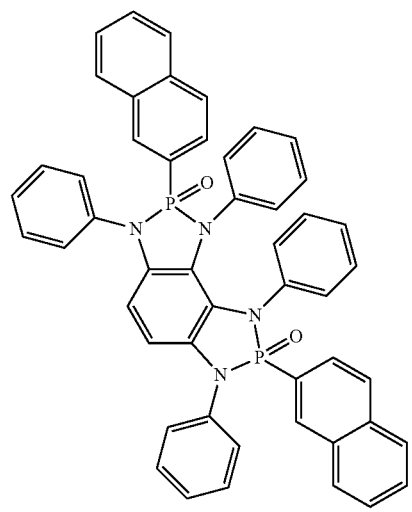
(199)
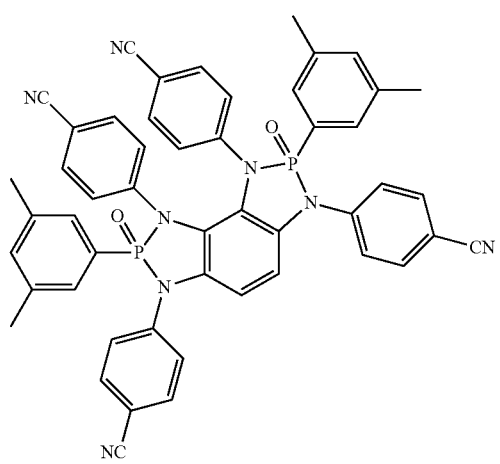
(200)
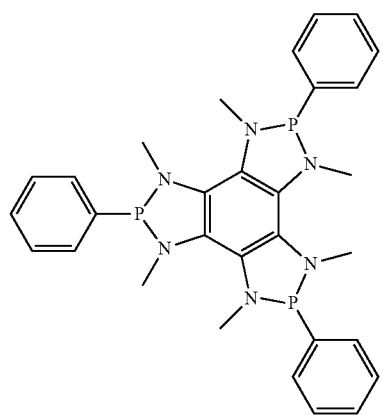
(201)
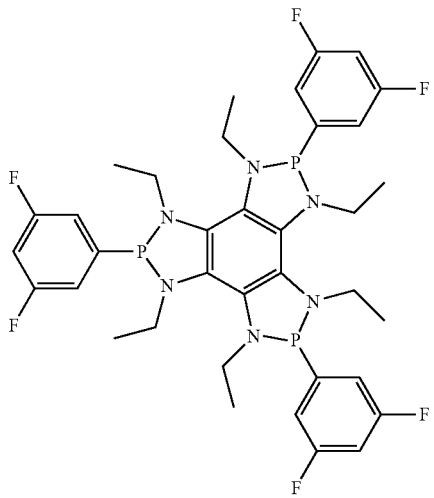
(202)
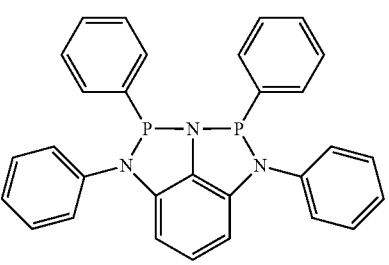
(203)
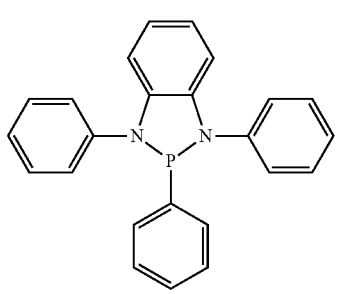
(204)
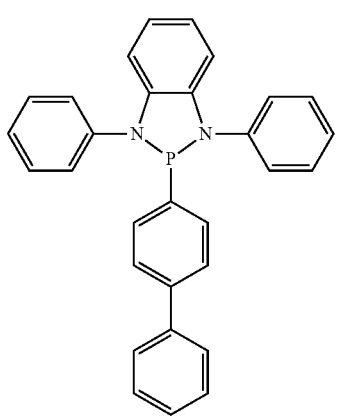

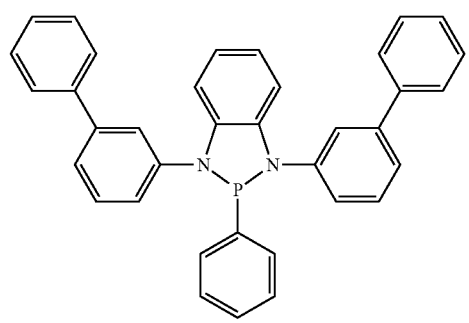 (205)
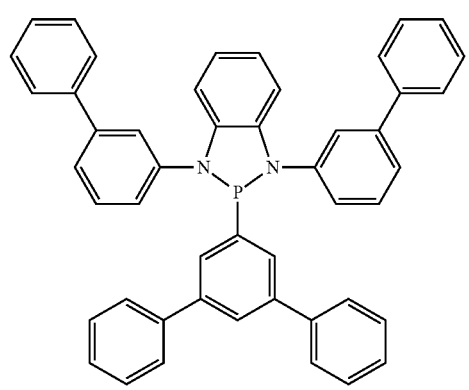 (206)
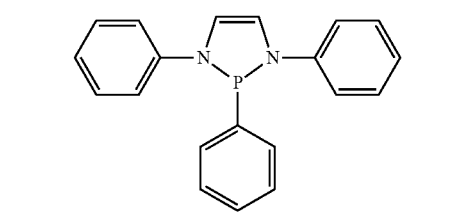 (207)
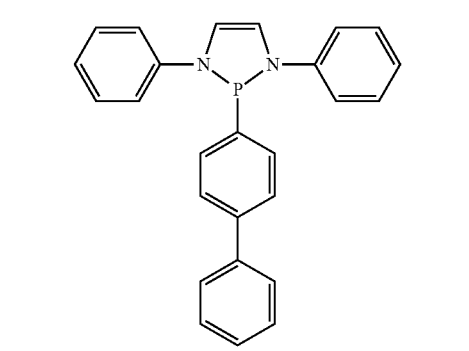 (208)
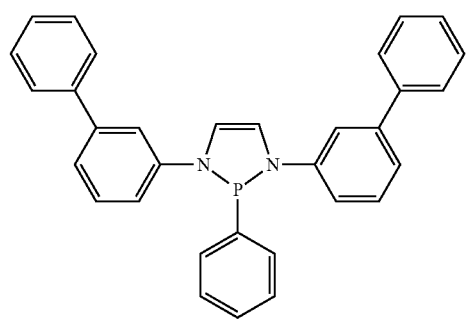 (209)
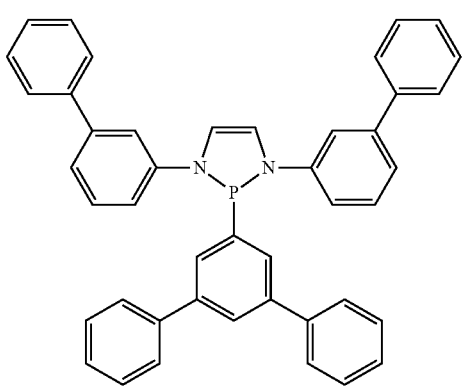 (210)
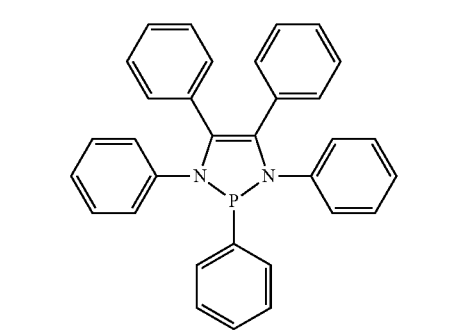 (211)
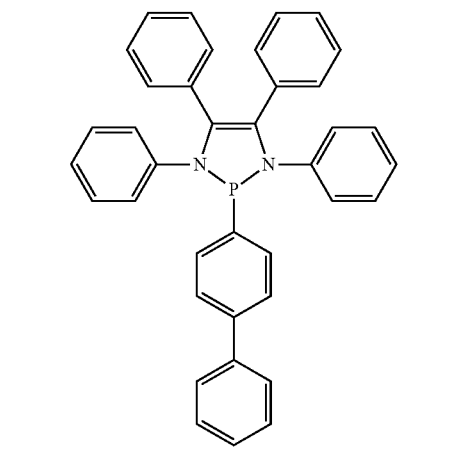 (212)
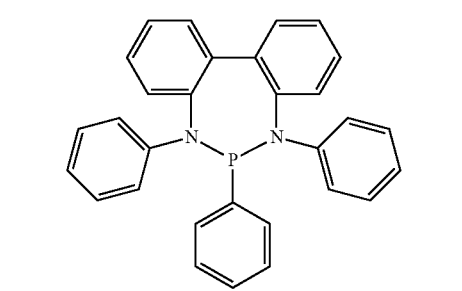 (213)

(214) 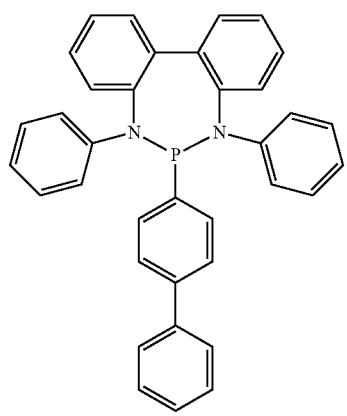
(215) 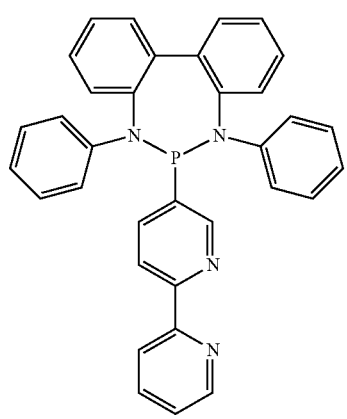
(216) 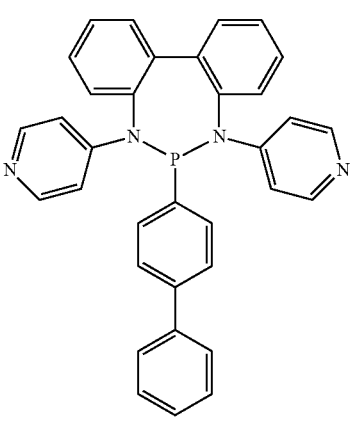
(217) 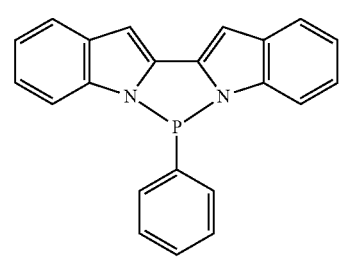
(218) 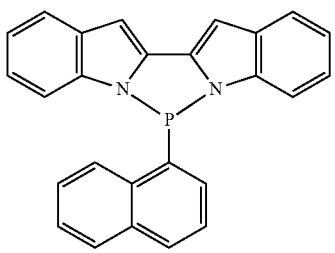
(219) 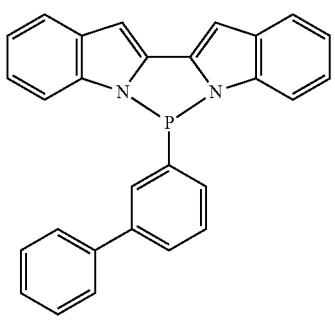
(220) 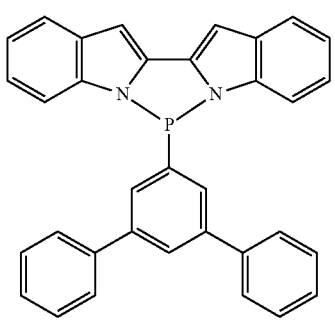
(221) 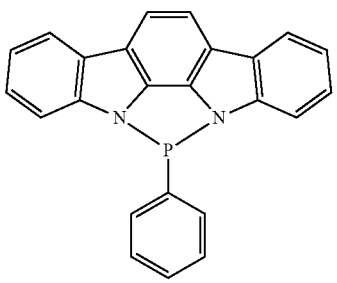
(222) 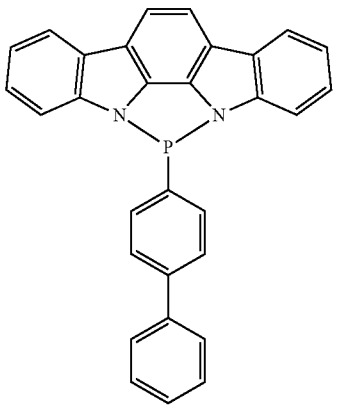

(223)
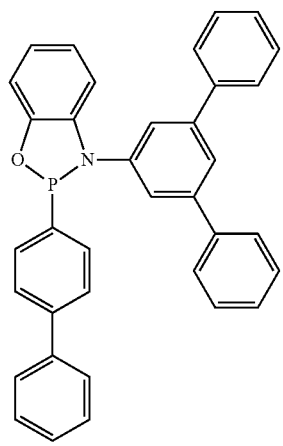
(226)
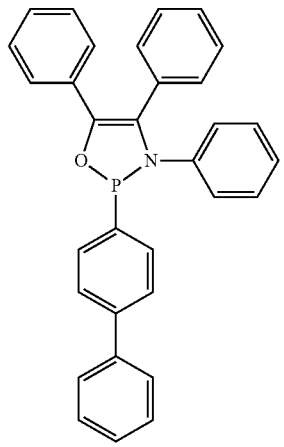
(224)
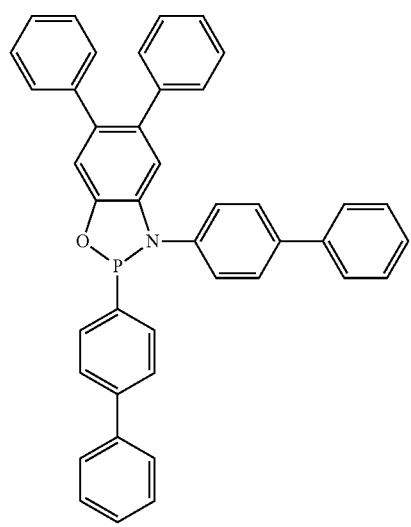
(227)
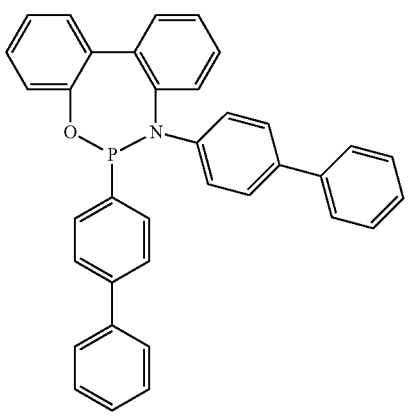
(228)
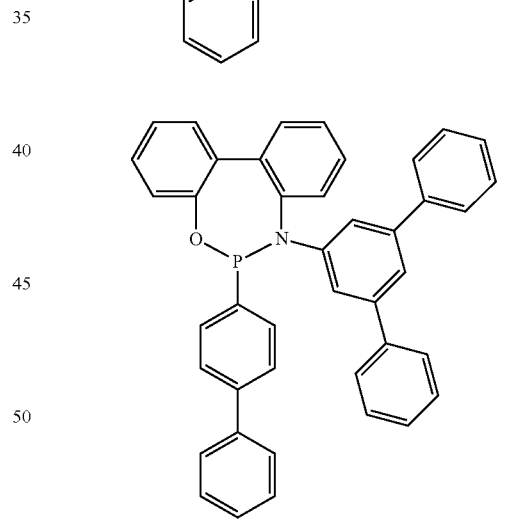
(225)
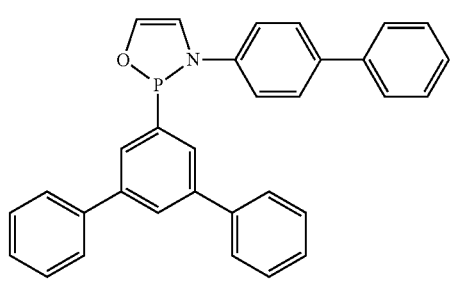
(229)
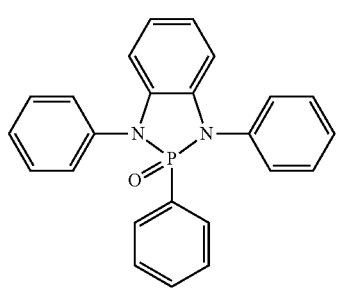

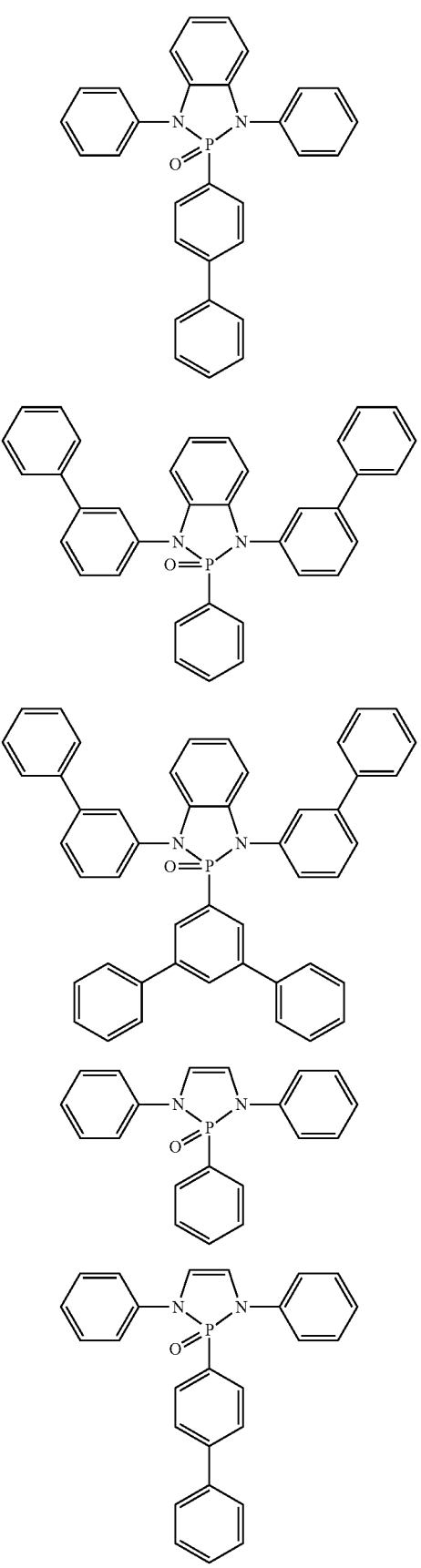
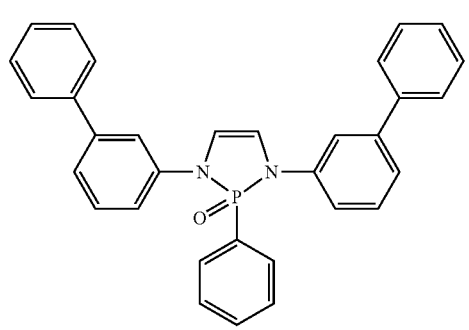
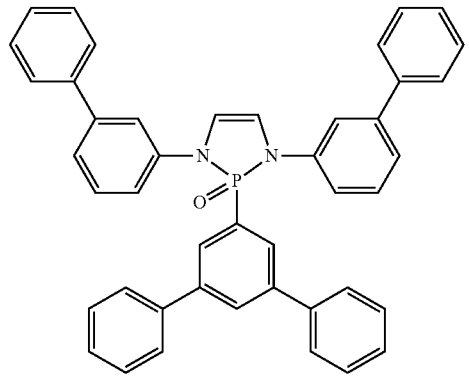
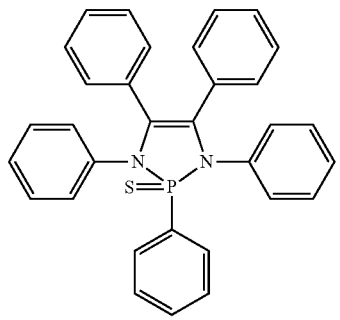
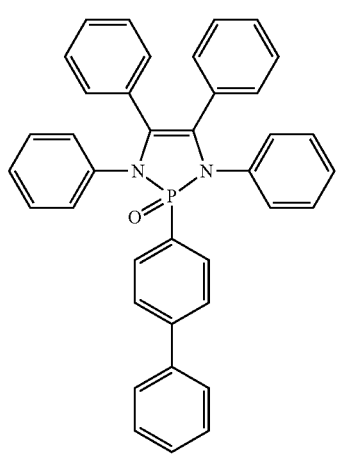

(239) 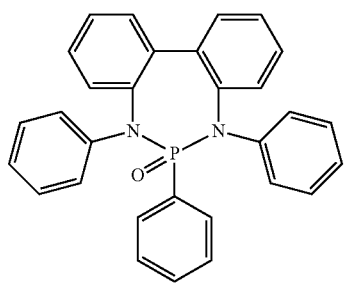
(240) 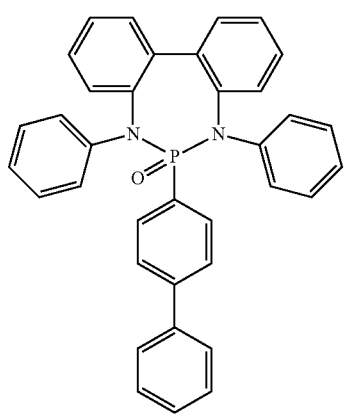
(241) 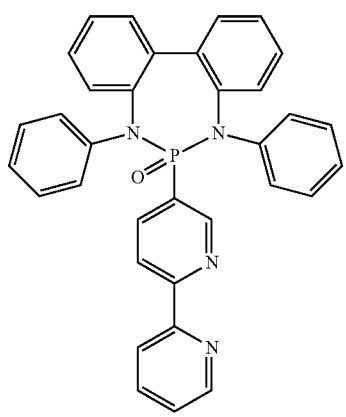
(242) 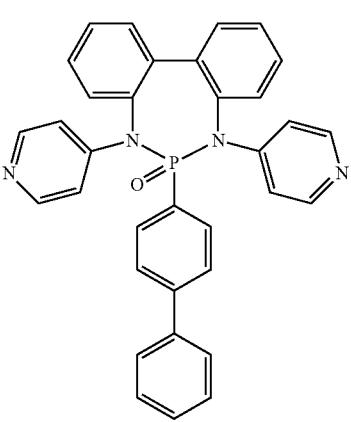
(243) 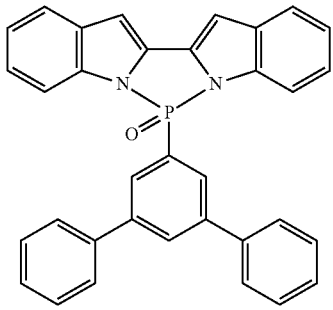
(244) 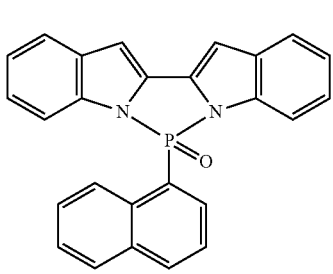
(245) 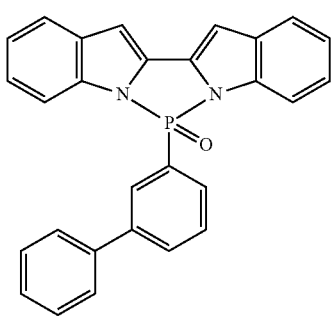
(246) 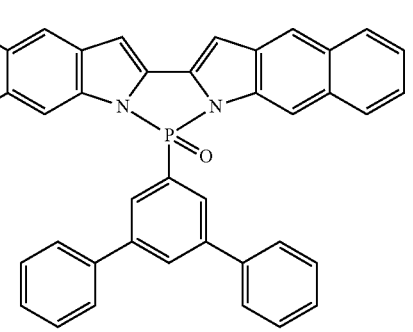
(247) 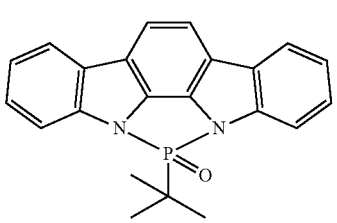

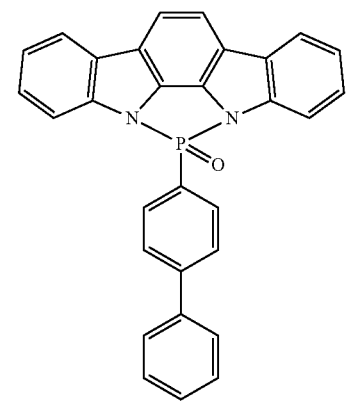
(248)
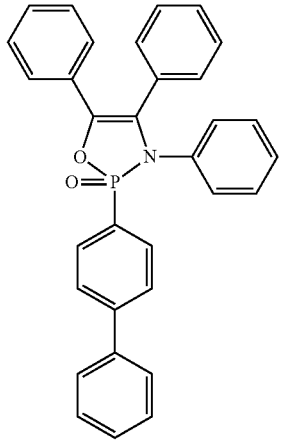
(252)
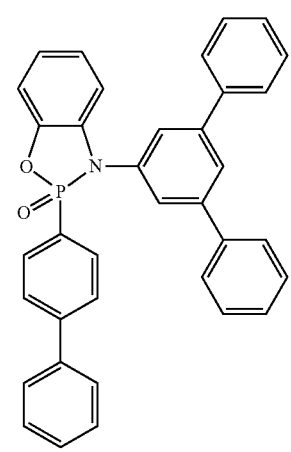
(249)
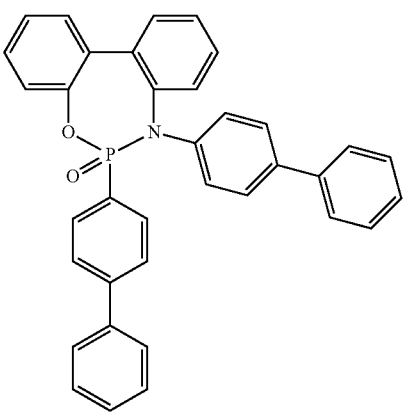
(253)
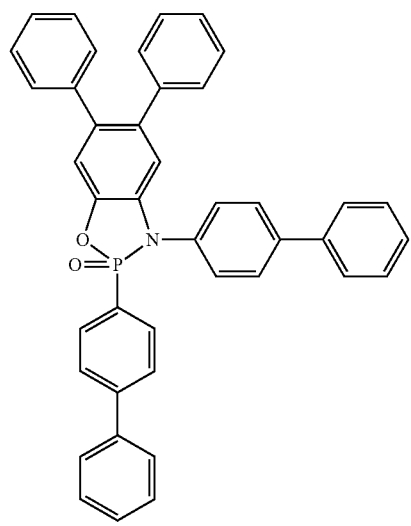
(250)
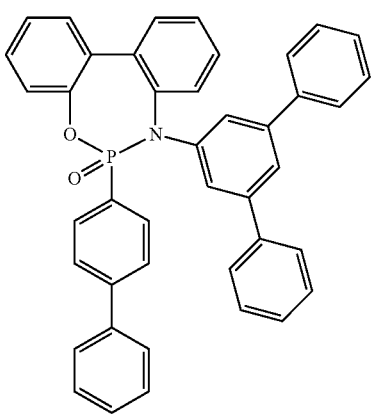
(254)
(251)

(255)
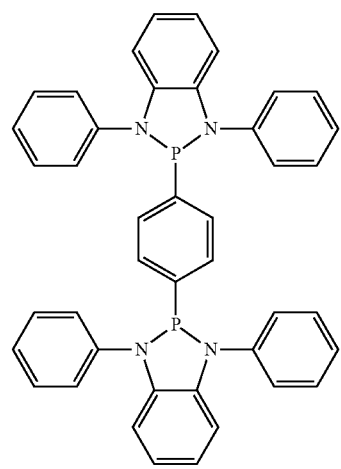
(256)
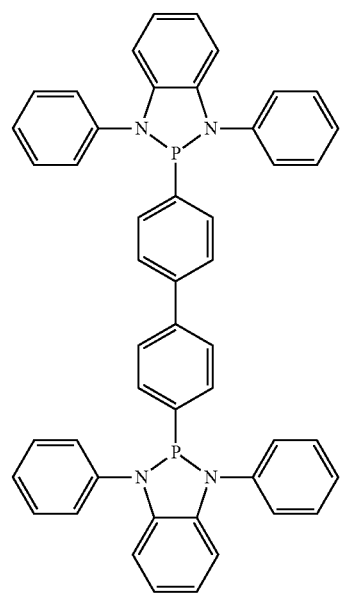
(257)
(258)
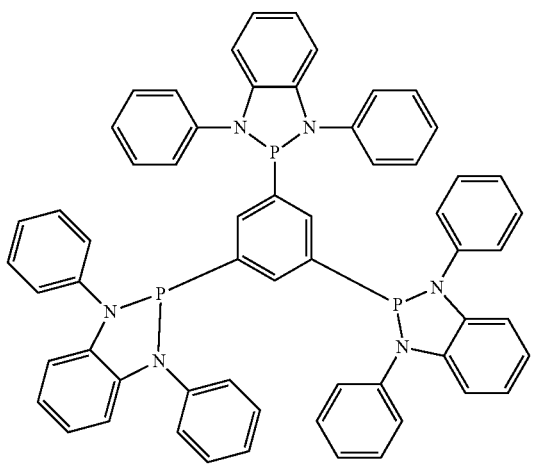
(259)
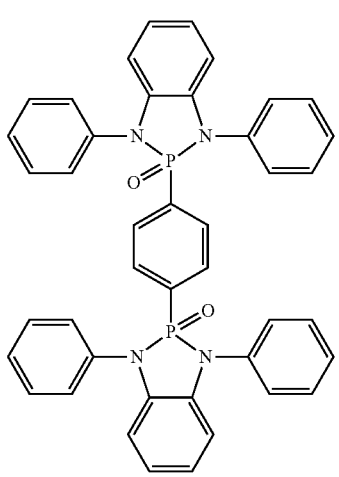
(260)
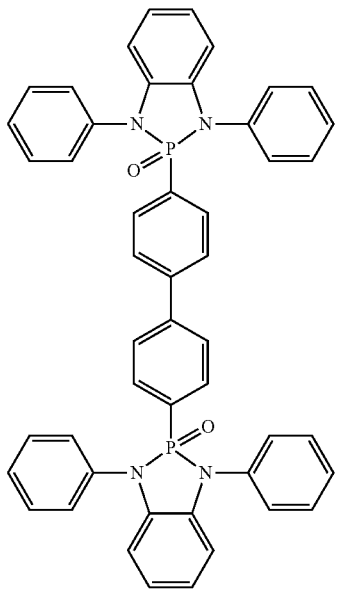

(261)
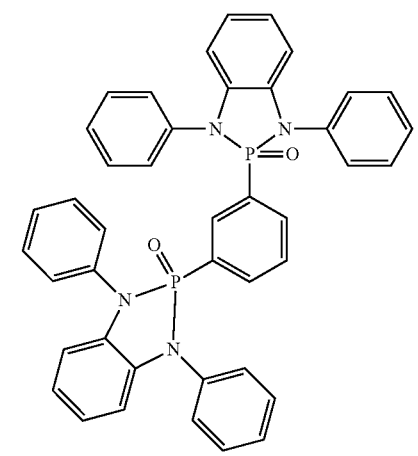
(264)
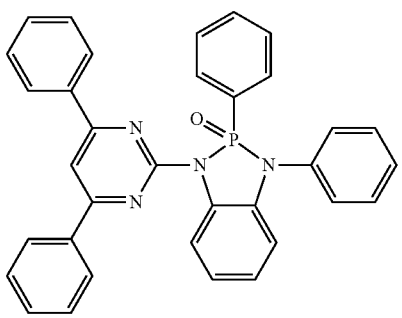
(265)
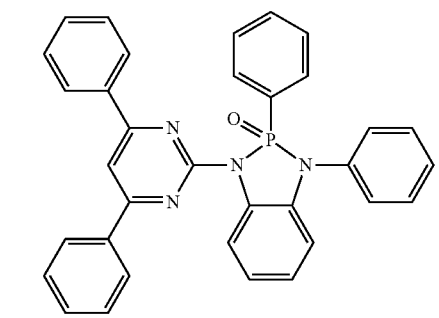
(262)
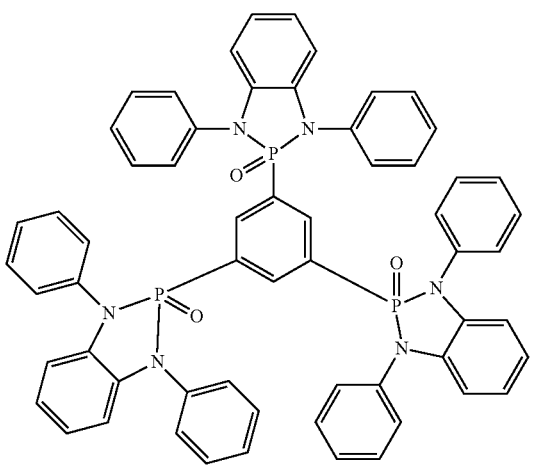
(266)
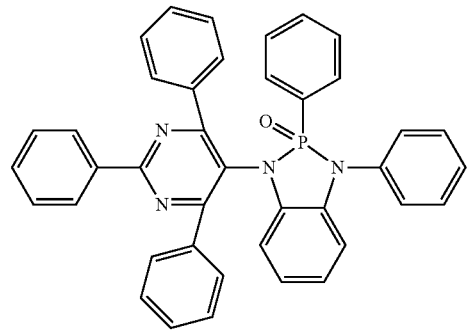
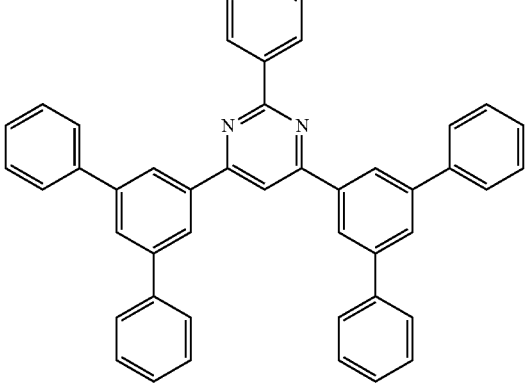
(263)
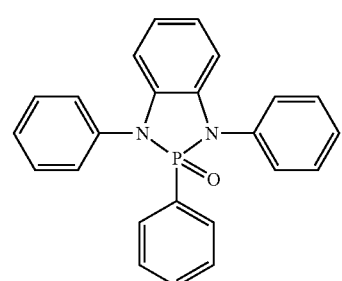
(267)
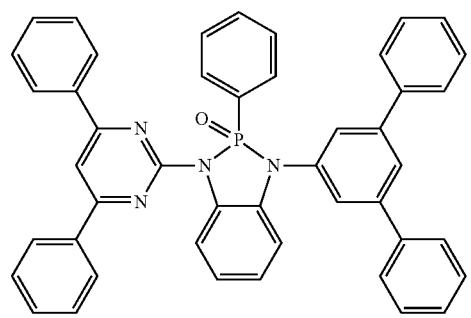

-continued
(268)
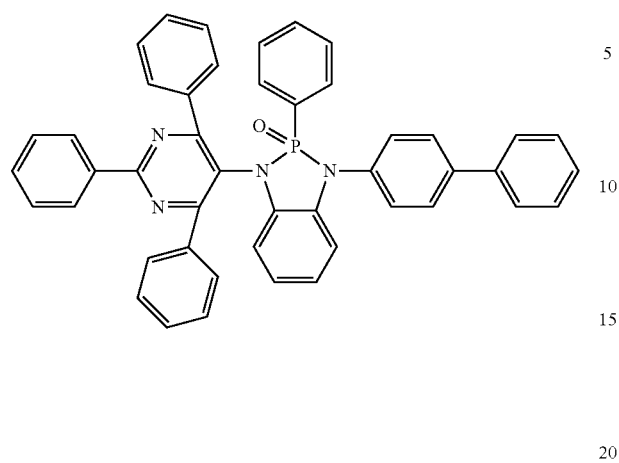
(269)
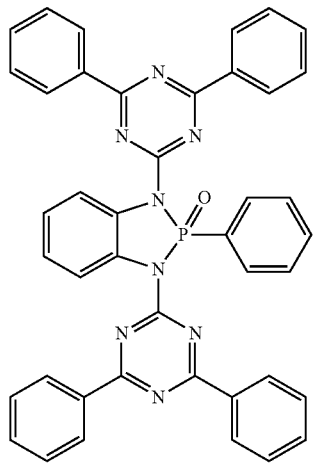
(270)
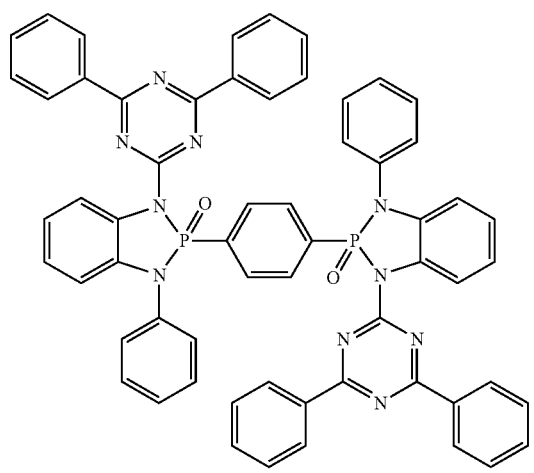
-continued
(271)
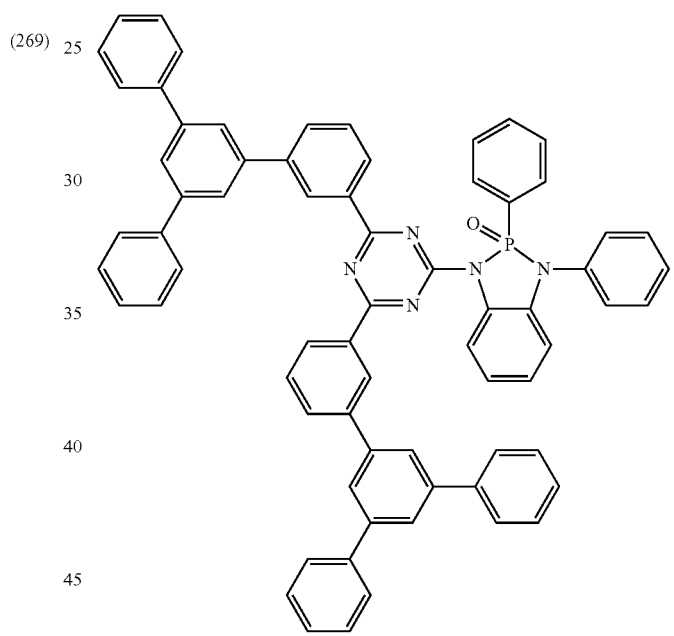
(272)
(273)
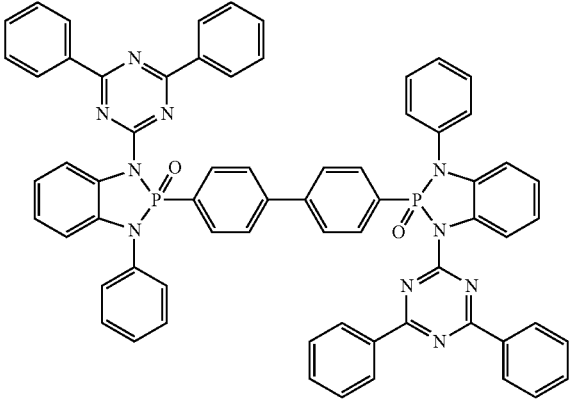

-continued (274)

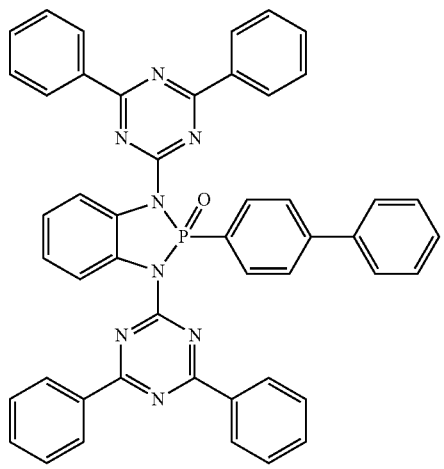

As stated above, the compounds of the formula (1) are used in an electronic device. An electronic device here is taken to mean a device which comprises at least one layer which comprises at least one organic compound. However, the component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers which have, for example, an exciton-blocking function may likewise be introduced between two emitting layers. However, it should be pointed out that each of these layers does not necessarily have to be present. The organic electroluminescent device here may comprise one emitting layer or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

The compound in accordance with the embodiments indicated above can be employed in various layers, depending on the precise structure. Preference is given to an organic electroluminescent device comprising a compound of the formula (1) or formulae (8) to (18) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer. The preferred embodiments indicated above also apply to the use of the materials in organic electronic devices.

In a preferred embodiment of the invention, the compound of the formula (1) or formulae (8) to (18) is employed as matrix material for a fluorescent or phosphorescent compound in an emitting layer. The organic electroluminescent device here may comprise one emitting layer or it may comprise a plurality of emitting layers, where at least one emitting layer comprises at least one compound according to the invention as matrix material.

If the compound of the formula (1) or formulae (8) to (18) is employed as matrix material for an emitting compound in an emitting layer, it is preferably employed in combination with one or more phosphorescent materials (triplet emitters). For the purposes of this invention, phosphorescence is taken to mean the luminescence from an excited state of relatively high spin multiplicity, i.e. a spin state >1, in particular from an excited triplet state. For the purposes of this application, all luminescent complexes with metals from the second and third transition-metal series, in particular all iridium and platinum complexes, are to be regarded as phosphorescent compounds.

The mixture of the compound of the formula (1) or (8) to (18) and the emitting compound comprises between 99 and 1% by vol., preferably between 98 and 10% by vol., particularly preferably between 97 and 60% by vol., in particular between 95 and 80% by vol., of the compound of the formula (1) or (8) to (18), based on the entire mixture of emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture of emitter and matrix material.

A further preferred embodiment of the present invention is the use of the compound of the formula (1) or formulae (8) to (18) as matrix material for a phosphorescent emitter in combination with a further matrix material. Particularly suitable matrix materials which can be employed in combination with the compounds of the formula (1) or formulae (8) to (18) are aromatic ketones, aromatic phosphine oxides or aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolyl-biphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the unpublished application DE 102008036982.9, WO 07/063754 or WO 08/056746, zinc complexes, for example in accordance with EP 652273 or WO 09/062578, or diazasilole or tetraazasilole derivatives, for example in accordance with the unpublished application DE 102008056688.8.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 05/053051. It is furthermore possible to use a metal complex which is identical or similar to the metal complex in the emitting layer as hole-transport or hole-injection material directly adjacent to the emitting layer, as described, for example, in WO 09/030981.

In a further preferred embodiment of the invention, the compound of the formula (1) or (8) to (18) is employed as electron-transport material in an electron-transport or electron-injection layer. The emitting layer here may be fluorescent or phosphorescent. If the compound is employed as electron-transport material, it may be preferred for it to be doped, for example with alkali metal complexes, such as, for example, Liq (lithium hydroxy-quinolinate).

In still a further preferred embodiment of the invention, the compound of the formula (1) or (8) to (18) is employed in a hole-blocking layer. A hole-blocking layer is taken to mean a layer which is directly adjacent to an emitting layer on the cathode side.

In still a further embodiment of the invention, the compound of the formula (1) or (8) to (18) is employed in a hole-transport layer or in an electron-blocking layer or exciton-blocking layer.

It is furthermore possible to use the compound of the formula (1) or (8) to (18) both in a hole-blocking layer or electron-transport layer and as matrix in an emitting layer and/or both in a hole-transport layer or exciton-blocking layer and as matrix in an emitting layer.

All materials as usually employed in accordance with the prior art can be used in the further layers of the organic electroluminescent device according to the invention. The person skilled in the art will therefore be able, without inventive step, to employ all materials known for organic electroluminescent devices in combination with the compounds of the formula (1) or formulae (8) to (18) according to the invention.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose. These processes are also particularly suitable for oligomers, dendrimers and polymers.

These processes are generally known to the person skilled in the art and can be applied by him, without inventive step, to organic electroluminescent devices comprising the compounds according to the invention.

The compounds of the formula (1) indicated as preferred above are novel and are thus likewise a subject-matter of the present invention.

The invention therefore relates to compounds of the formula (1')

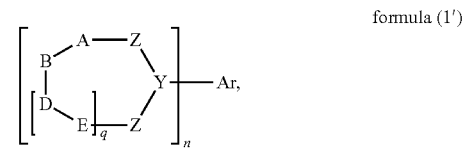

formula (1')

where the following applies to the symbols and indices used:
A-B and D-E are each, identically or differently on each occurrence, a unit of the following formula (2), (3), (4), (5) or (6):

formula (2)

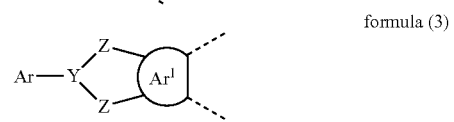

formula (3)

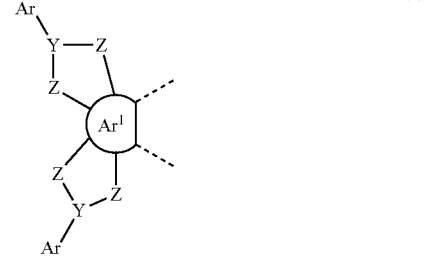

formula (4)

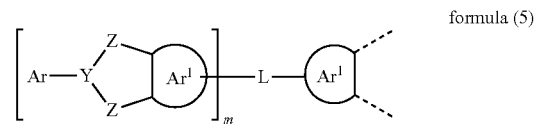

formula (5)

formula (6)

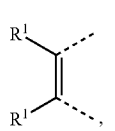

where the dashed bond in each case represents the bond to Z;
and
Z is, identically or differently on each occurrence, N—R², O or S, with the proviso that both groups Z bonded to the same group Y do not stand for O;
or
A-Z and B-Z are each, identically or differently on each occurrence, a unit of the following formula (7) and q=0, formula (7)

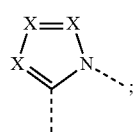

the dashed bond in formula (7) represents the linking of this unit in the compound of the formula (1), where the nitrogen is linked to the group Y;
Y is on each occurrence, identically or differently, P(=O), As(=O), As(=S), Sb(=O), Sb(=S), Bi(=O) or Bi(=S);
Ar is on each occurrence, identically or differently, an aromatic or heteroaromatic ring system having 5 to 60 aromatic ring atoms, which may be substituted by one or more radicals R¹;
Ar¹ is on each occurrence, identically or differently, an aryl or heteroaryl group having 5 to 16 aromatic ring atoms, which may be substituted by one or more radicals R¹;
X is on each occurrence, identically or differently, CR¹ or N;
L is a single bond or a divalent, trivalent or tetravalent group;
R¹ is selected on each occurrence, identically or differently, from the group consisting of H, D, F, Cl, Br, I, CN, NO₂, N(R³)₂, C(=O)R³, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R³, where one or more non-adjacent CH₂ groups may be replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, CN or NO₂, an aromatic or heteroaromatic ring system having 5 to 60 aromatic ring atoms, which may in each case be substituted by one or more radicals R³, an aryloxy or heteroaryloxy group having 5 to 60 aromatic ring atoms, which may be substituted by one or more radicals R³, or a combination of these systems, where two or more adjacent substituents R¹ may optionally form a monocyclic or polycyclic, aliphatic, aromatic or heteroaromatic ring system, which may be substituted by one or more radicals R³;
R² is selected on each occurrence, identically or differently, from the group consisting of a straight-chain alkyl group having 1 to 40 C atoms or a branched or cyclic alkyl group having 3 to 40 C atoms, each of which may be substituted by one or more radicals R³, where one or more non-adjacent CH₂ groups may be replaced by R³C=CR³, C≡C or C=O and where one or more H atoms may be replaced by D, F, Cl, Br, I, CN or NO₂, an aromatic or heteroaromatic ring system having 5 to 60 aromatic ring atoms, which may in each case be substituted by one or more radicals R³, or a combination of these systems; R¹ and R² which are adjacent to one another in the 1,2-position may optionally form a monocyclic or polycyclic, aliphatic, aromatic or heteroaromatic ring system, which may be substituted by one or more radicals R³;
R³ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R³ may form a mono- or polycyclic, aliphatic, aromatic or heteroaromatic ring system with one another;
n is 1 to 10, preferably 1, 2, 3, 4, 5 or 6;
m is 1 if L is a single bond or a divalent group, or is 2 if L is a trivalent group, or is 3 if L is a tetravalent group;
q is on each occurrence, identically or differently, 0 or 1;
the following compounds are excluded from the invention:

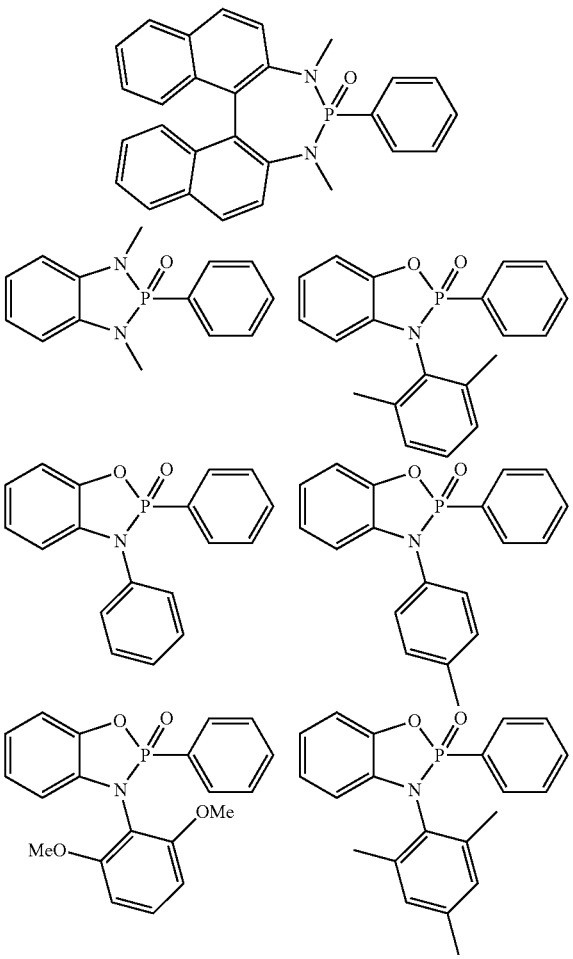

-continued

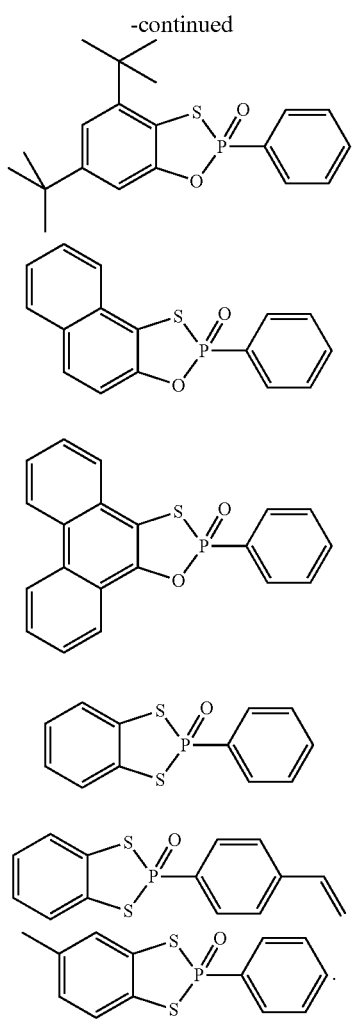

The same preferences as already indicated above for the electronic device apply to the compounds of the formula (1') according to the invention.

The invention therefore furthermore relates to the use of the compounds according to the invention in an electronic device.

The invention furthermore relates to compounds of the formula (39) and to the use thereof in electronic devices and to electronic devices, in particular organic electroluminescent devices, comprising these compounds:

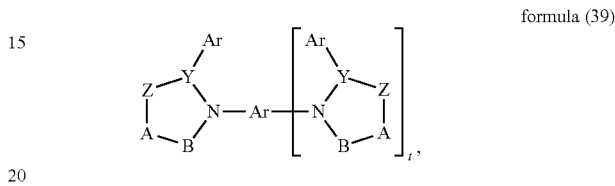

formula (39)

where the symbols and indices used have the meanings indicated above for formula (1), and t represents an integer from 1 to 10, preferably 1, 2, 3, 4, 5 or 6. The preferred embodiments indicated above for formula (1) likewise apply to compounds of the formula (39).

For the preparation of the compounds of the formula (1) and the compounds according to the invention, the process described below has proven particularly suitable. To this end, either an ortho-dibromo-substituted aromatic compound is reacted with a primary amine or an ortho-diamino-substituted aromatic compound is reacted with an aryl bromide in a Hartwig-Buchwald coupling, as indicated in Scheme 1 as route A or route B. The resultant diamine is reacted with an aromatic phosphonyl chloride or an aromatic bis(phosphonyl chloride) to give the corresponding compound of the formula (1) or (1'). The synthesis shown by way of example in Scheme 1 can of course be carried out entirely analogously with other aromatic groups or with differently substituted groups.

Scheme 1:

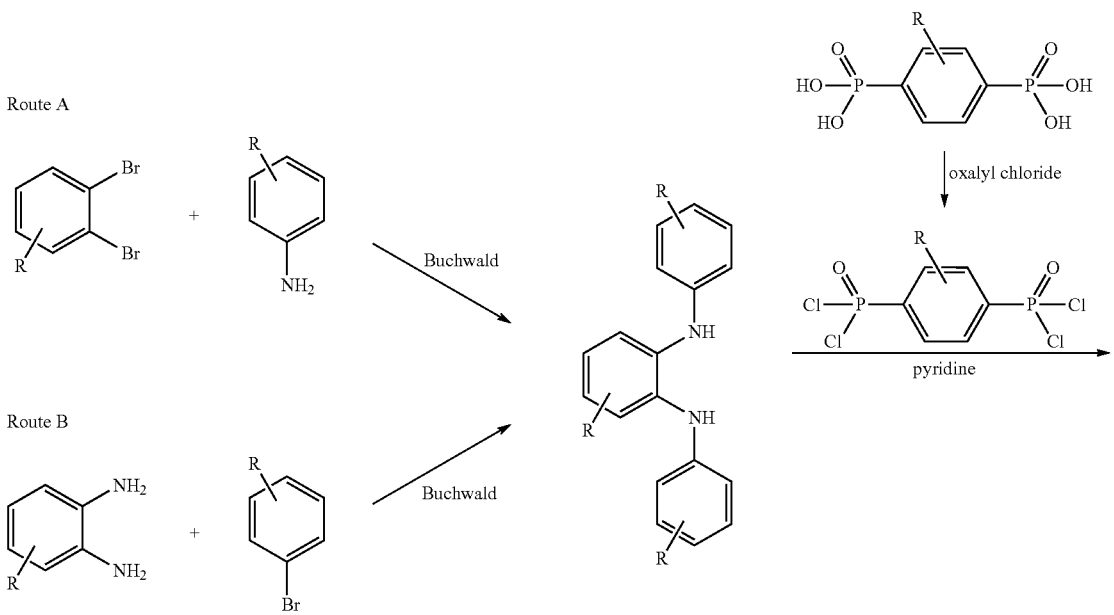

-continued

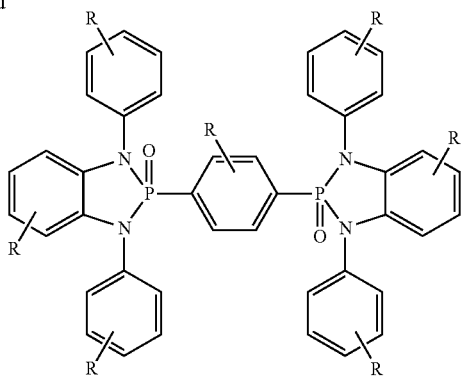

The synthesis of compounds of the formula (1) which are substituted differently at the two ortho nitrogen atoms is shown in Scheme 2. These compounds are accessible through the use of an ortho-diamino-substituted aromatic compound in which one of the two amino groups is substituted.

Scheme 2:

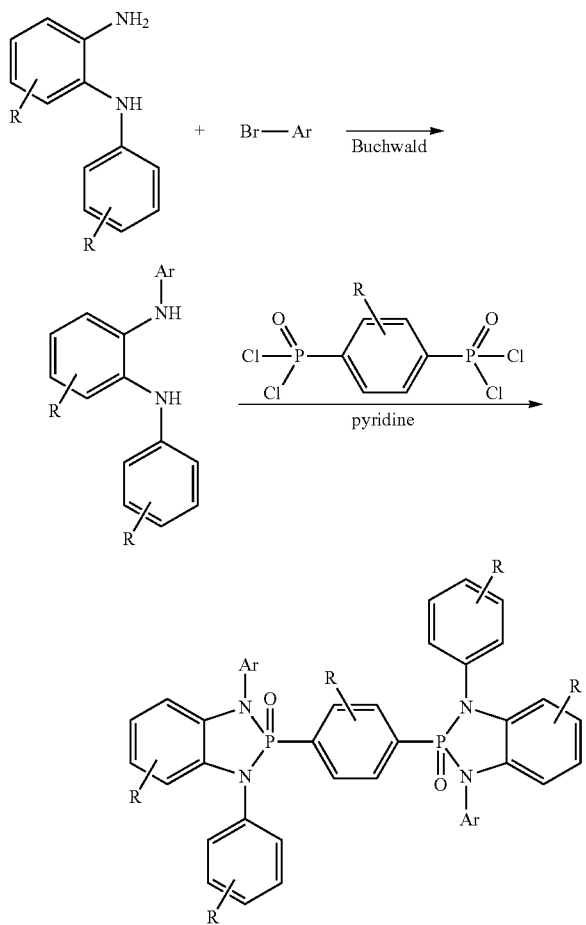

The present invention furthermore relates to a process for the preparation of the compounds according to the invention indicated above by reaction of an ortho-diamino-substituted aromatic compound, in which the amino groups are unsubstituted or preferably monosubstituted, with an aromatic phosphonyl chloride derivative or an aromatic oligophosphonyl chloride derivative.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisation here is preferably carried out via the halogen functionality or the boronic acid functionality or via the polymerisable group. It is furthermore possible to crosslink the polymers via groups of this type. The polymers according to the invention can be employed as crosslinked or uncrosslinked layer.

The invention therefore furthermore relates to oligomers, polymers or dendrimers containing one or more of the compounds according to the invention indicated above, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. For the recurring units of the compounds according to the invention in oligomers, dendrimers and polymers, the same preferences apply as described above.

For the preparation of the oligomers or polymers, the monomers according to the invention are homopolymerised or copolymerised with further monomers. Preference is given to homopolymers or copolymers in which the units of the formula (1) or (8) to (18) or (39) are present in an amount of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. Precisely the combination of units of the formulae (1) and (8) to (18) with triplet emitters gives particularly good results.

A further possibility of polymerisation consists in the reaction of a compound Hal$_2$Y—Ar—YHal$_2$, where Hal stands for Cl, Br or I, with a corresponding tetramine. This gives compounds, oligomers and polymers of the following formula (37). The formation of compounds, oligomers and polymers of the following formula (38) is possible entirely analogously.

formula (37)

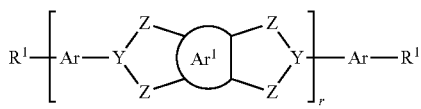

formula (38)

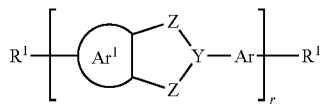

where the symbols used have the meanings indicated above, and r stands for an integer between 2 and 1,000,000. The present invention likewise relates to these compounds, oligomers and polymers. The preferences indicated above apply to the symbols indicated in formulae (37) and (38). The group Ar$^1$ is particularly preferably selected, identically or differently on each occurrence, from 1,2,4,5-linked benzene or 1,2,3,4-linked benzene.

The compounds of the formula (1) or (1') may furthermore also be functionalised further and thus converted into extended structures. An example which may be mentioned here is the reaction with arylboronic acids by the SUZUKI method or with primary or secondary amines by the HARTWIG-BUCHWALD method. Thus, the compounds of the formula (1) or (1') may also be bonded directly to phosphorescent metal complexes or also to other metal complexes.

The compounds according to the invention and the organic electroluminescent devices according to the invention are distinguished by the following surprising advantages over the prior art:

1. The compounds according to the invention and compounds of the formula (1) or formulae (8) to (18), employed as matrix material for fluorescent or phosphorescent emitters, result in very high efficiencies and in long lifetimes. This applies in particular if the compounds are employed as matrix material for a phosphorescent emitter. Significantly better efficiencies, in particular power efficiencies, and lifetimes are obtained than on use of structurally similar phosphine oxides as matrix materials.
2. The compounds according to the invention and compounds of the formula (1) or (8) to (18) are suitable not only as matrix for green- and red-phosphorescent compounds, but also, in particular, for blue-phosphorescent compounds.
3. In contrast to many compounds in accordance with the prior art which undergo partial or complete pyrolytic decomposition on sublimation, the compounds according to the invention have high thermal stability.
4. The compounds according to the invention, employed in organic electroluminescent devices, result in high efficiencies and in steep current-voltage curves with low use voltages.

These advantages indicated above are not accompanied by an impairment in the other electronic properties.

The invention is explained in greater detail by the following examples, without wishing to restrict it thereby. From the descriptions, the person skilled in the art will be able to carry out the invention throughout the range disclosed and prepare further complexes according to the invention without inventive step and use them in electronic devices or use the process according to the invention.

EXAMPLES

The following syntheses are carried out under a protective-gas atmosphere in dried solvents, unless indicated otherwise. The starting compound used can be, for example, 1,4-bis(phosphonic acid)benzene (Inorganic Chemistry 1996, 35(17), 4942-4949), N,N'-diphenyl-1,2-benzenediamine (Organic Letters 2007, 9(7), 1339-1342) or N-phenyl-o-phenylenediamine (Indian Journal of Pharmaceutical Sciences 2003, 65(2), 135-138).

Example 1a

Synthesis of 1,4-bis(phosphonyl chloride)benzene

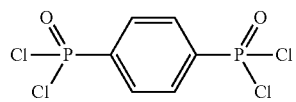

55.2 g (232 mmol) of 1,4-bis(phosphonic acid)benzene are initially introduced in 1400 ml of methylene chloride, and 10 drops of DMF are added. 86.3 ml (1020 mmol) of oxalyl chloride in 400 ml of methylene chloride are added dropwise at room temperature, and the mixture is stirred at 45° C. for 5 h. The solvent is removed in vacuo, and the product is recrystallised from hexane under protective gas. Yield: 70 g (227 mmol), 98%.

The following compounds can be obtained analogously:

| Ex. | Staring material | Product | Yield |
|---|---|---|---|
| 1b | | | 89% |

-continued

| Ex. | Staring material | Product | Yield |
|---|---|---|---|
| 1c | | | 95% |
| 1d | | | 84% |

Example 2

General Synthesis of N,N'-diaryl-1,2-benzenediamine 1.06 g (4.75 mmol) of Pd(OAc)$_2$ and 14.46 ml (14.46 mmol) of tri-tert-butyl-phosphine (1 M solution in toluene) are added to 660 ml of degassed toluene, and the mixture is stirred for 5 min. 240 mmol of the 1,2-dibromobenzene derivative, 505 mmol of the arylamine and 67.22 g (700 mmol) of sodium tert-butoxide are then added to the solution, which is then degassed and stirred for 10 h at 140° C. under a protective-gas atmosphere. After the solution has cooled, 600 ml of NH$_4$Cl solution and 150 ml of ethyl acetate are added, the phases are separated, washed with water, dried over MgSO$_4$ and evaporated. The solid is dissolved in toluene and filtered off through Celite. The crude product is washed by stirring with hot heptane.

Example 3

Synthesis of 4,5-dimethyl-N,N'-diphenyl-1,2-benzenediamine

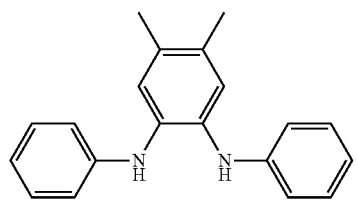 [SMILES: Cc1cc(Nc2ccccc2)c(Nc2ccccc2)cc1C]

The synthesis is carried out in accordance with the general procedure in accordance with Example 2 from 63.3 g (240 mmol) of 1,2-dibromo-4,5-dimethylbenzene and 46 ml (505 mmol) of aniline. The precipitated solid is recrystallised from toluene/acetonitrile (5:1), and the residue is washed with MeOH, giving 65 g (223 mmol) of a crystalline solid. The overall yield is 93%.

Example 4

Synthesis of N,N'-ditolyl-1,2-benzenediamine

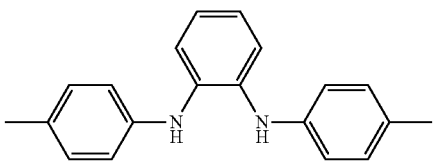

The synthesis is carried out in accordance with the general procedure in accordance with Example 2 from 56.6 g (240 mmol) of 1,2-dibromobenzene and 54 ml (505 mmol) of p-toluidine. The precipitated solid is recrystallised from toluene/acetonitrile (5:1), and the residue is washed with MeOH, giving 75 g (262 mmol) of a crystalline solid. The overall yield is 98%.

Example 5

Synthesis of N,N'-di-o-tolyl-1,2-benzeneamine

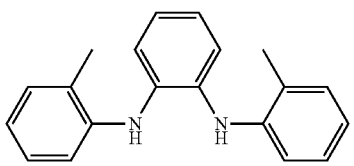 [SMILES: Cc1ccccc1Nc1ccccc1Nc1ccccc1C]

The synthesis is carried out in accordance with the general procedure in accordance with Example 2 from 56.6 g (240 mmol) of 1,2-dibromobenzene and 54 ml (505 mmol) of o-toluidine. The precipitated solid is recrystallised from toluene/acetonitrile (5:1), and the residue is washed with MeOH, giving 68 g (237 mmol) of a crystalline solid. The overall yield is 90%.

Example 6

Synthesis of 4,5-dimethyl-N,N'-di-p-tolyl-1,2-benzenediamine

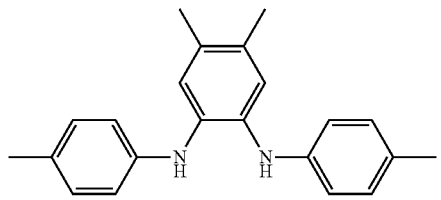

The synthesis is carried out in accordance with the general procedure in accordance with Example 2 from 63.3 g (240 mmol) of 1,2-dibromo-4,5-dimethylbenzene and 54 ml (505 mmol) of p-toluidine. The precipitated solid is recrystallised from toluene/acetonitrile (5:1), and the residue is washed with MeOH, giving 69 g (218 mmol) of a crystalline solid. The overall yield is 91%.

Example 7

Synthesis of N,N'-bis(biphenyl-4-yl)-1,2-benzenediamine

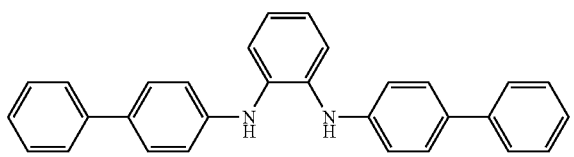 [SMILES: c1ccc(-c2ccc(Nc3ccccc3Nc3ccc(-c4ccccc4)cc3)cc2)cc1]

The synthesis is carried out in accordance with the general procedure in accordance with Example 2 from 56.6 g (240 mmol) of 1,2-dibromobenzene and 85.4 g (505 mmol) of 4-aminobiphenyl. The precipitated solid is recrystallised from toluene/acetonitrile (5:1), and the residue is washed with MeOH, giving 78 g (189 mmol) of a crystalline solid. The overall yield is 80%.

Example 8

Synthesis of 4,5-dimethyl-N,N'-bis(biphenyl-4-yl)-1,2-benzenediamine

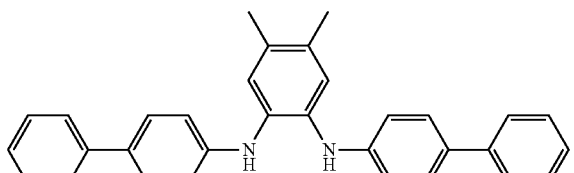

The synthesis is carried out in accordance with the general procedure in accordance with Example 2 from 63.3 g (240 mmol) of 1,2-dibromo-4,5-dimethylbenzene and 85.4 g (505 mmol) of 4-aminobiphenyl. The precipitated solid is recrystallised from toluene/acetonitrile (5:1), and the residue is washed with MeOH, giving 80.3 g (182 mmol) of a crystalline solid. The overall yield is 76%.

Example 9

Synthesis of N-biphenyl-4-yl-N'-phenyl-1,2-benzenediamine

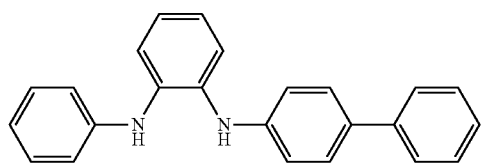 [SMILES: c1ccc(Nc2ccccc2Nc2ccc(-c3ccccc3)cc2)cc1]

0.35 g (1.58 mmol) of Pd(OAc)$_2$ and 4.8 ml (4.86 mmol) of tri-tent-butyl-phosphine (1 M solution in toluene) are added to 660 ml of degassed toluene, and the mixture is stirred for 5 min. 37.2 g (160 mmol) of 4-bromobiphenyl, 29.4 g (160 mmol) of N-phenyl-o-phenylenediamine and 22.4 g (233 mmol) of sodium tert-butoxide are then added to the solution, which is then degassed and stirred for 10 h at 140° C. under a protective-gas atmosphere. After the solution has cooled, 200 ml of NH$_4$Cl solution and 50 ml of ethyl acetate are added, the phases are separated, washed with water, dried over MgSO$_4$ and evaporated. The solid is dissolved in toluene and filtered off via Celite. The crude product is washed by stirring with hot heptane and washed with MeOH, giving 47 g (140 mmol) of a crystalline solid. The overall yield is 80%.

Example 10

General Synthesis of the Diazaphospholes 158 mmol of the N,N'-diaryl-1,2-benzenediamine are dissolved in 500 ml of pyridine and cooled to 0° C. 74 mmol of the 1,4-bis(phosphonyl chloride)benzene, dissolved in 1000 ml of toluene, are added dropwise to this solution at 0° C. with vigorous stirring, the mixture is stirred for 1 h and then heated under reflux for 24 h. The solvent is distilled off in vacuo, the solid is washed by boiling in ethyl acetate, filtered off with suction, washed once with 100 ml of ethyl acetate and subsequently recrystallised from dioxane.

Example 11

Synthesis of H3

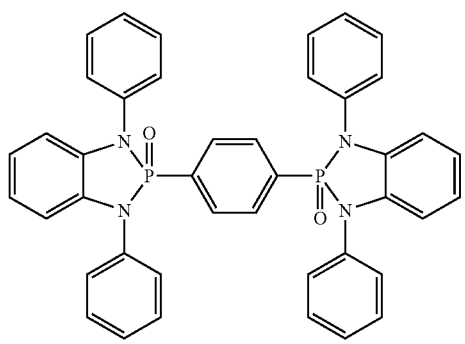 [SMILES: O=P1(c2ccc(P3(=O)N(c4ccccc4)c4ccccc4N3c3ccccc3)cc2)N(c2ccccc2)c2ccccc2N1c1ccccc1]

The synthesis is carried out in accordance with the general procedure in accordance with Example 10 from 42 g (158 mmol) of N,N'-diphenyl-1,2-benzenediamine and 23 g (74 mmol) of 1,4-bis(phosphonyl chloride)benzene. The solid obtained is recrystallised a number of times from dioxane. Yield: 34.4 g (50 mmol), 68%, purity 99.9% (HPLC).

Example 12

Synthesis of H4

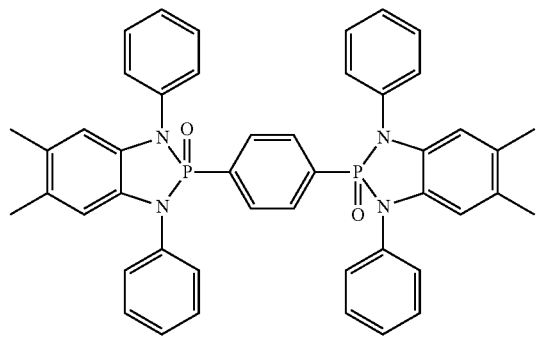

The synthesis is carried out in accordance with the general procedure in accordance with Example 10 from 45.5 g (158 mmol) of 4,5-dimethyl-N,N'-diphenyl-1,2-benzenediamine and 23 g (74 mmol) of 1,4-bis(phosphonyl chloride)benzene. The solid obtained is recrystallised a number of times from dioxane. Yield: 35.7 g (48 mmol), 65%, purity 99.9% (HPLC).

Example 13

Synthesis of H5

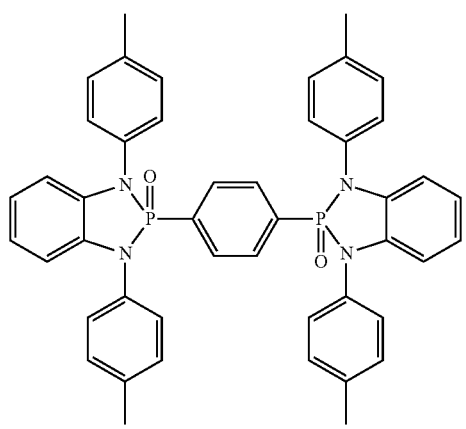 [SMILES: Cc1ccc(N2c3ccccc3N(c3ccc(C)cc3)P2(=O)c2ccc(P3(=O)N(c4ccc(C)cc4)c4ccccc4N3c3ccc(C)cc3)cc2)cc1]

The synthesis is carried out in accordance with the general procedure in accordance with Example 10 from 45.5 g (158 mmol) of N,N'-ditolyl-1,2-benzenediamine and 23 g (74 mmol) of 1,4-bis(phosphonyl chloride)benzene. The solid obtained is recrystallised a number of times from dioxane. Yield: 37.9 g (51 mmol), 69%, purity 99.9% (HPLC).

Example 14

Synthesis of H6

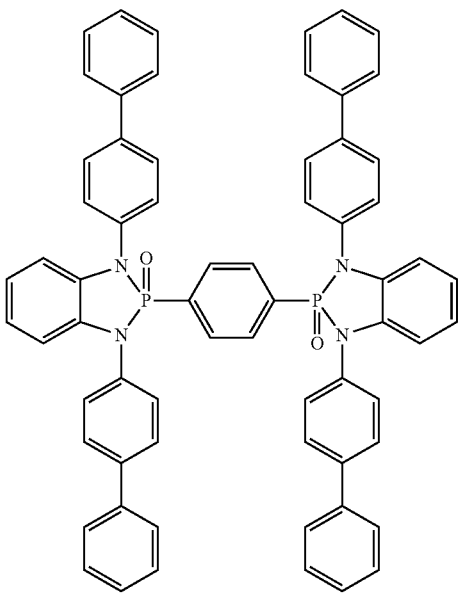 [SMILES: O=P1(c2ccc(P3(=O)N(c4ccc(-c5ccccc5)cc4)c4ccccc4N3c3ccc(-c4ccccc4)cc3)cc2)N(c2ccc(-c3ccccc3)cc2)c2ccccc2N1c1ccc(-c2ccccc2)cc1]

The synthesis is carried out in accordance with the general procedure in accordance with Example 10 from 65 g (158 mmol) of N,N'-bis(biphenyl-4-yl)-1,2-benzenediamine and 23 g (74 mmol) of 1,4-bis(phosphonyl chloride)benzene. The solid obtained is recrystallised a number of times from dioxane. Yield: 43.9 g (44.3 mmol), 60%, purity 99.9% (HPLC).

Example 15

Synthesis of H7

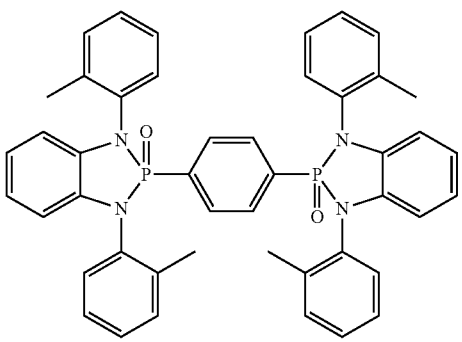 [SMILES: Cc1ccccc1N1c2ccccc2N(c2ccccc2C)P1(=O)c1ccc(P2(=O)N(c3ccccc3C)c3ccccc3N2c2ccccc2C)cc1]

The synthesis is carried out in accordance with the general procedure in accordance with Example 10 from 45.5 g (158 mmol) of N,N'-di-o-tolyl-1,2-benzenediamine and 23 g (74 mmol) of 1,4-bis(phosphonyl chloride)benzene. The solid obtained is recrystallised a number of times from dioxane. Yield: 34.6 g (46.5 mmol), 63%, purity 99.9% (HPLC).

Example 16

Synthesis of H8

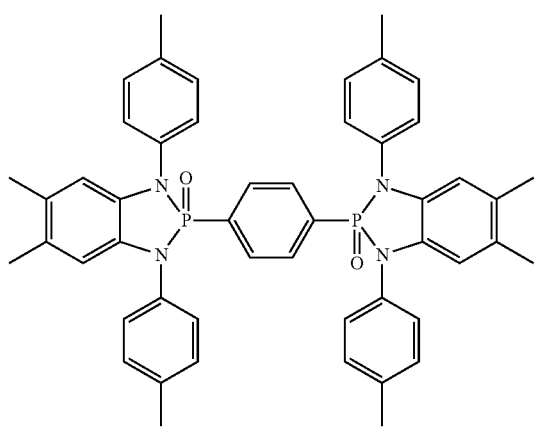

The synthesis is carried out in accordance with the general procedure in accordance with Example 10 from 50.6 g (158 mmol) of 4,5-dimethyl-N,N'-di-p-tolyl-1,2-benzenediamine and 23 g (74 mmol) of 1,4-bis(phosphonyl chloride)benzene. The solid obtained is recrystallised a number of times from dioxane. Yield: 35.4 g (44.3 mmol), 60%, purity 99.9% (HPLC).

Example 17

Synthesis of H9

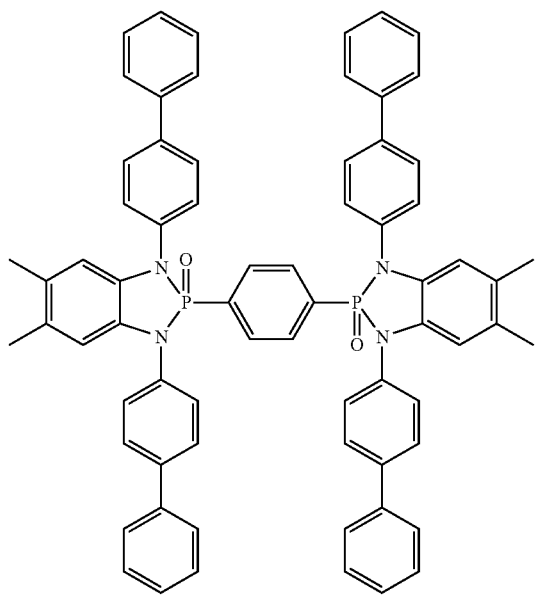

The synthesis is carried out in accordance with the general procedure in accordance with Example 10 from 69.6 g (158 mmol) of 4,5-dimethyl-N,N'-bis(biphenyl-4-yl)-1,2-benzenediamine and 23 g (74 mmol) of 1,4-bis(phosphonyl chloride)benzene. The solid obtained is recrystallised a number of times from dioxane. Yield: 48.8 g (46.6 mmol), 63%, purity 99.9% (HPLC).

Example 18

Synthesis of H10

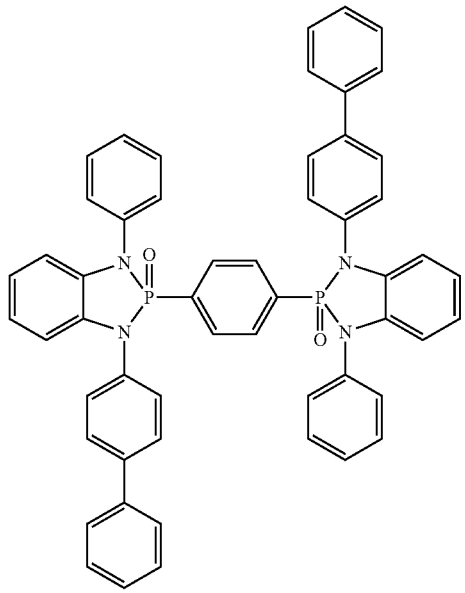 [SMILES: O=P1(c2ccc(P3(=O)N(c4ccccc4)c4ccccc4N3c3ccc(-c4ccccc4)cc3)cc2)N(c2ccccc2)c2ccccc2N1c1ccc(-c2ccccc2)cc1]

The synthesis is carried out in accordance with the general procedure in accordance with Example 9 from 53.1 g (158 mmol) of N-biphenyl-4-yl-N'-phenyl-1,2-benzenediamine and 23 g (74 mmol) of 1,4-bis(phosphonyl chloride)benzene. The solid obtained is recrystallised a number of times from dioxane. Yield: 50.2 g (42 mmol), 81%, purity 99.9% (HPLC).

The following compounds are obtained analogously:

| Ex. | Starting material | Product | Yield |
|---|---|---|---|
| 19 | 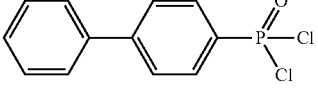 | 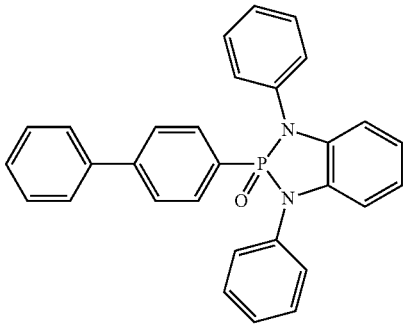 [SMILES: O=P1(c2ccc(-c3ccccc3)cc2)N(c2ccccc2)c2ccccc2N1c1ccccc1] | 67% |
| 20 | 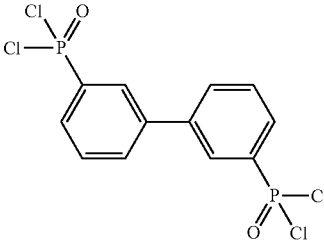 | 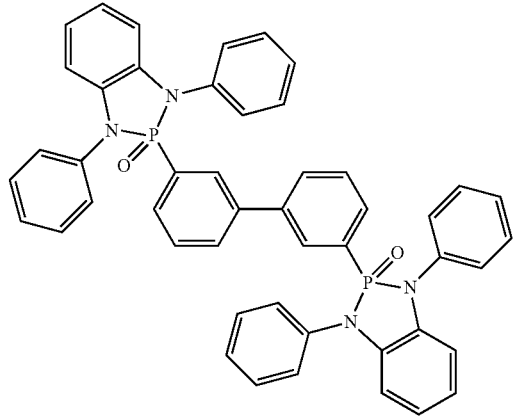 [SMILES: O=P1(c2cccc(-c3cccc(P4(=O)N(c5ccccc5)c5ccccc5N4c4ccccc4)c3)c2)N(c2ccccc2)c2ccccc2N1c1ccccc1] | 50% |
| 21 | 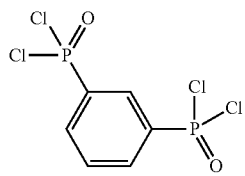 [SMILES: O=P(Cl)(Cl)c1cccc(P(=O)(Cl)Cl)c1] | 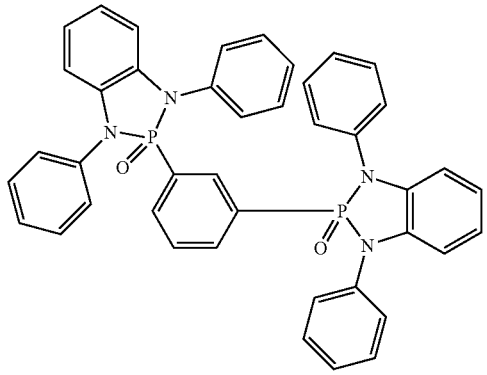 [SMILES: O=P1(c2cccc(P3(=O)N(c4ccccc4)c4ccccc4N3c3ccccc3)c2)N(c2ccccc2)c2ccccc2N1c1ccccc1] | 65% |
If the corresponding dichlorophosphines are employed instead of the phosphonyl chlorides, the following compounds are obtained:
| Ex. | Starting material | Product | Yield |
|---|---|---|---|
| 22 | 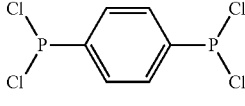 [SMILES: ClP(Cl)c1ccc(P(Cl)Cl)cc1] | 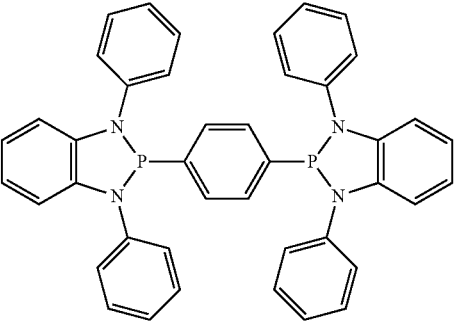 [SMILES: c1ccc(N2c3ccccc3N(c3ccccc3)P2c2ccc(P3N(c4ccccc4)c4ccccc4N3c3ccccc3)cc2)cc1] | 71% |

-continued
| Ex. | Starting material | Product | Yield |
|---|---|---|---|
| 23 | 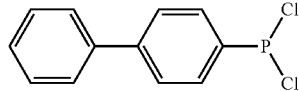 | 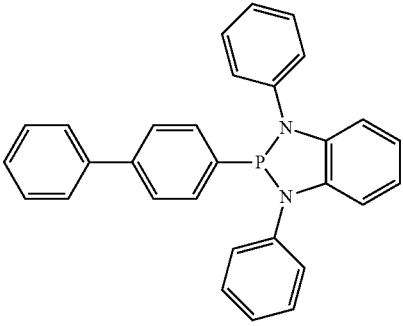 [SMILES: c1ccc(-c2ccc(P3N(c4ccccc4)c4ccccc4N3c3ccccc3)cc2)cc1] | 76% |
| 24 | 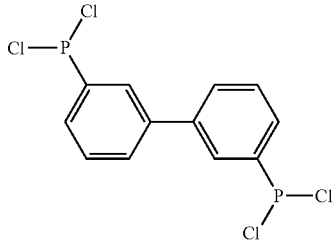 [SMILES: ClP(Cl)c1cccc(-c2cccc(P(Cl)Cl)c2)c1] | 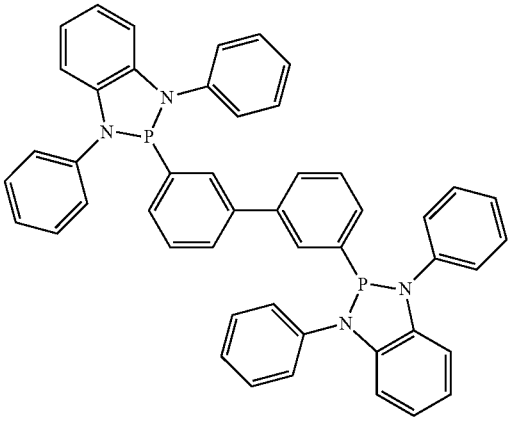 [SMILES: c1ccc(N2c3ccccc3N(c3ccccc3)P2c2cccc(-c3cccc(P4N(c5ccccc5)c5ccccc5N4c4ccccc4)c3)c2)cc1] | 44% |
| 25 | 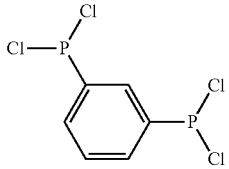 [SMILES: ClP(Cl)c1cccc(P(Cl)Cl)c1] | 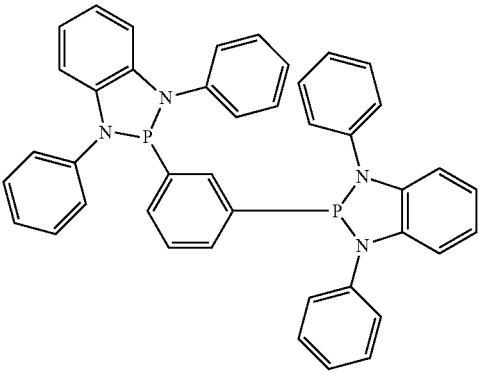 [SMILES: c1ccc(N2c3ccccc3N(c3ccccc3)P2c2cccc(P3N(c4ccccc4)c4ccccc4N3c3ccccc3)c2)cc1] | 46% |

Example 26

Synthesis of N,N'-dipyrid-4-yl-1,2-benzenediamine

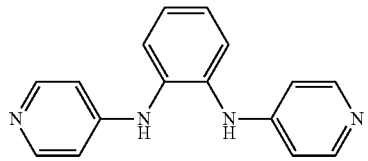 [SMILES: c1ccc(Nc2ccncc2)c(Nc2ccncc2)c1]

The synthesis is carried out in accordance with the general procedure of Example 2 from 56.6 g (240 mmol) of 1,2-dibromobenzene and 47.5 g (505 mmol) of 4-aminopyridine. The precipitated solid is recrystallised from toluene/acetonitrile (5:1), and the residue is washed with MeOH, giving 46.2 g (176 mmol) of a crystalline solid. The total yield is 73%.

Example 27

Synthesis of N-phenyl-N'-4,6-diphenyl-1,3,5-triazin-2-yl-1,2-benzenediamine

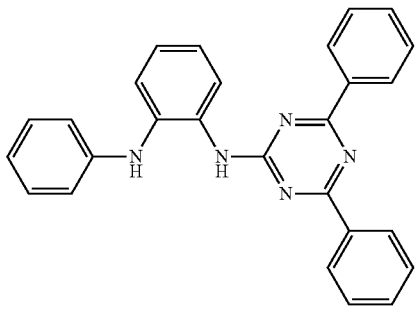 [SMILES: c1ccc(Nc2ccccc2Nc2nc(-c3ccccc3)nc(-c3ccccc3)n2)cc1]

51 ml (300 mmol) of ethyldiisopropylamine and subsequently, dropwise, a solution of 29.5 g (110 mmol) of 2-chloro-4,6-diphenyl-1,3,5-triazine in 100 ml of THF are added to a solution of 18.4 g (100 mmol) of N-phenyl-o-phenylenediamine in 200 ml of THF. After stirring at room temperature for 1 h, the reaction mixture is heated under reflux for 6 h. After cooling, the THF is removed in vacuo, the residue is dissolved in 50 ml of dichloromethane, and 300 ml of methanol are added dropwise. After the mixture has been stirred for 12 h, the solid is filtered off with suction, washed with MeOH and dried. The total yield is 27.8 g (67 mmol), 67%.

Example 28

Synthesis of H11

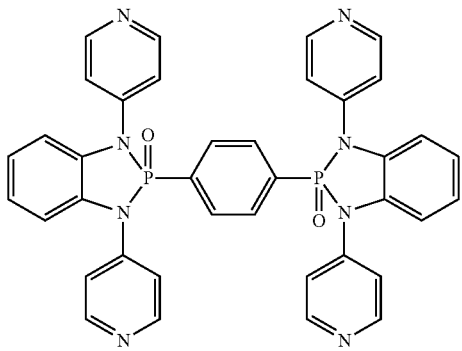 [SMILES: O=P1(c2ccc(P3(=O)N(c4ccncc4)c4ccccc4N3c3ccncc3)cc2)N(c2ccncc2)c2ccccc2N1c1ccncc1]

The synthesis is carried out in accordance with the general procedure of Example 10 from 41.4 g (158 mmol) of N,N'-dipyrid-4-yl-1,2-benzenediamine and 23 g (74 mmol) of 1,4-bis(phosphonyl chloride)benzene. The solid obtained is recrystallised a number of times from dioxane. Yield: 39.4 g (57 mmol), 77%, purity 99.9% (HPLC).

Example 29

Synthesis of H12

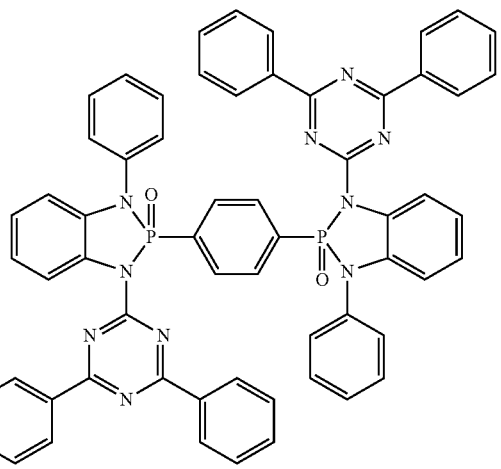

The synthesis is carried out in accordance with the general procedure of Example 10 from 65.6 g (158 mmol) of N-phenyl-N'-4,6-diphenyl-1,3,5-triazin-2-yl-1,2-benzenediamine and 23 g (74 mmol) of 1,4-bis(phosphonyl chloride)benzene. The solid obtained is recrystallised a number of times from chlorobenzene. Yield: 42.9 g (43 mmol), 58%, purity 99.9% (HPLC).

Example 30

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in Examples 31 to 50 below (see Tables 1 and 2). Glass plates coated with structured ITO (indium tin oxide) in a thickness of 150 nm are coated with 20 nm of PEDOT (poly-(3,4-ethylenedioxy-2,5-thiophene), spin-coated from water; purchased from H. C. Starck, Goslar, Germany) for improved processing. These coated glass plates form the substrates to which the OLEDs are applied. The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All materials are thermally vapour-deposited in a vacuum chamber. The emission layer here always consists of at least one matrix material (host material) and an emitting dopant (emitter), with which the matrix material or materials is (are) admixed by co-evaporation in a certain volume proportion. Information such as H1:CBP:TER1 (55%:35%:10%) here means that the material H1 is present in the layer in a volume proportion of 55%, CBP in a volume proportion of 35% and TER1 in a volume proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in per cent) as a function of the luminous density, calculated from current-voltage-luminance characteristic lines (IUL characteristic lines), and the lifetime are determined. The lifetime is defined as the time after which the luminous density has dropped from a certain initial luminous density $I_0$ to a certain proportion. LD80 means that the said lifetime is the time at which the luminous density has dropped to $0.8 \cdot I_0$ (to 80%), i.e. from, for example, 4000 cd/m² to 3200 cd/m².

The compounds according to the invention can be employed, inter alia, as matrix materials (host materials) for phosphorescent dopants. Compounds H3, H4, H5, H6 and H7 according to the invention are used here. Compounds H1, H2 and H8 are used as comparison in accordance with the prior art, OLEDs comprising the green-emitting dopant TEG1, the blue-emitting dopant TEB1 and the red-emitting dopant TER1 are shown. The results for the OLEDs are summarised in Table 2. Ex. 31-38 show OLEDs comprising materials in accordance with the prior art and serve as comparative examples. OLEDs 39-50 according to the invention exhibit the advantages on use of compounds of the formula (1).

The use of compounds according to the invention enables, compared with the prior art, improvements to be achieved in all relevant parameters, especially lifetime and power efficiency. In particular, the improvement in the power efficiency is of major importance since the operating time of mobile equipment is crucially dependent on the energy consumption. Even increases of 10% should be regarded as significant progress here.

Compared with the phosphine oxide-containing matrix material H2, the compounds according to the invention exhibit the greatest advance (comparison of Ex. 35-37 with Ex. 44-48). Although the use of matrix materials H3, H4, H5, H6 and H7 according to the invention gives comparable operating voltages as on use of H2 in accordance with the prior art, the current efficiency can, however, be significantly increased. The improvement is between about 25% (Ex. 45 and Ex. 36) and about 50% (Ex. 48 and Ex. 37), giving correspondingly improved power efficiencies. This is particularly evident on use of H1 as electron-transport material, where the improvement in the power efficiency compared with the prior art is about 50% (Ex. 48 and Ex. 37). It should be emphasised here that the improvement in the power efficiency is accompanied by a significant increase in the lifetime. Compared with the prior art, the use of compounds according to the invention increases the lifetime by a factor of 1.8 (Ex. 45 and Ex. 36) to 2.8 (Ex. 47 and Ex. 36).

Significant improvements can also be achieved compared with OLEDs comprising H1, which already exhibit relatively good performance data, through the use of compounds according to the invention. This applies to red-emitting (Ex. 31, 32 compared with Ex. 39, 40) and to green-emitting OLEDs (Ex. 33, 34 and Ex. 41-43). In the case of red-emitting OLEDs, the power efficiency can be increased by about more than 15%, but in particular the lifetime can be also be significantly increased. The improvement in the lifetime here is about more than 50%. In the case of green-emitting OLEDs, although the compounds according to the invention only result in a small increase in the power efficiency, or none at all, the use of H3, H4 and H5 as matrix materials gives, however, a very significant improvement in the lifetime. The increase is up to 55% (Ex. 41 and Ex. 33). In the case of blue-emitting OLEDs, the voltage drops by 1 V and the power efficiency increases by 33% on use of H3 as host material (Ex. 49 and Ex. 38).

A very clear advantage with respect to the operating voltage and thus in particular also the power efficiency can be obtained through the use of the triazine-substituted compound H9. This exhibits significantly improved operating voltage, power efficiency and also lifetime compared with the prior art (Ex. 50).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| 31 (comp.) | HTM1 20 nm | — | NPB 20 nm | H1:TER1 (85%:15%) 30 nm | — | Alq$_3$ 20 nm | LiF 1 nm |
| 32 (comp.) | HTM1 20 nm | — | NPB 20 nm | H1:CBP:TER1 (45%:45%:10%) 30 nm | H1 10 nm | Alq$_3$ 20 nm | LiF 1 nm |
| 33 (comp.) | HTM1 160 nm | — | EBM1 20 nm | H1:TEG1 (90%:10%) 30 nm | H1 10 nm | ETM1:LiQ (50%:50%) 40 nm | — |
| 34 (comp.) | HTM1 160 nm | — | EBM1 20 nm | H1:TEG1 (90%:10%) 30 nm | — | ETM1:LiQ (50%:50%) 40 nm | — |
| 35 (comp.) | HTM1 160 nm | — | EBM1 20 nm | H2:TEG1 (90%:10%) 30 nm | H1 10 nm | Alq$_3$ 20 nm | LiF 1 nm |
| 36 (comp.) | HTM1 140 nm | HIL1 5 nm | EBM1 130 nm | H2:TEG1 (85%:15%) 30 nm | — | H1:LiQ (50%:50%) 40 nm | — |
| 37 (comp.) | HTM1 140 nm | HIL1 5 nm | EBM1 130 nm | H2:TEG1 (85%:15%) | — | H1 40 nm | LiQ 3 nm |
| 38 (comp.) | HTM1 140 nm | — | NPB 5 nm/ EBM2 15 nm | H8:TEB1 (90%:10%) | — | H1 30 nm | LiQ 2 nm |

TABLE 1-continued

| | | | | Structure of the OLEDs | | | |
|---|---|---|---|---|---|---|---|
| Ex. | HTL Thickness | IL Thickness | EBL Thickness | EML Thickness | HBL Thickness | ETL Thickness | EIL Thickness |
| 39 | HTM1 20 nm | — | NPB 20 nm | H4:TER1 (85%:15%) 30 nm | — | Alq$_3$ 20 nm | LiF 1 nm |
| 40 | HTM1 20 nm | — | NPB 20 nm | H4:CBP:TER1 (45%:45%:10%) 30 nm | H1 10 nm | Alq$_3$ 20 nm | LiF 1 nm |
| 41 | HTM1 160 nm | — | EBM1 20 nm | H3:TEG1 (90%:10%) 30 nm | H1 10 nm | ETM1:LiQ (50%:50%) 40 nm | — |
| 42 | HTM1 160 nm | — | EBM1 20 nm | H5:TEG1 (90%:10%) 30 nm | H1 10 nm | ETM1:LiQ (50%:50%) 40 nm | — |
| 43 | HTM1 160 nm | — | EBM1 20 nm | H4:TEG1 (90%:10%) 30 nm | — | ETM1:LiQ (50%:50%) 40 nm | — |
| 44 | HTM1 160 nm | — | EBM1 20 nm | H4:TEG1 (90%:10%) 30 nm | H1 10 nm | Alq$_3$ 20 nm | LiF 1 nm |
| 45 | HTM1 140 nm | HIL1 5 nm | EBM1 130 nm | H3:TEG1 (85%:15%) 30 nm | — | H1:LiQ (50%:50%) 40 nm | — |
| 46 | HTM1 140 nm | HIL1 5 nm | EBM1 130 nm | H6:TEG1 (85%:15%) 30 nm | — | H1:LiQ (50%:50%) 40 nm | — |
| 47 | HTM1 140 nm | HIL1 5 nm | EBM1 130 nm | H5:TEG1 (85%:15%) | — | H1 40 nm | LiQ 3 nm |
| 48 | HTM1 140 nm | HIL1 5 nm | EBM1 130 nm | H7:TEG1 (85%:15%) | — | H1 40 nm | LiQ 3 nm |
| 49 | HTM1 140 nm | — | NPB 5 nm / EBM2 15 nm | H8:H3:TEB1 (80%:10%:10%) | — | H1 30 nm | LiQ 2 nm |
| 50 | HTM1 140 nm | HIL1 5 nm | EBM1 130 nm | H9:TEG1 (85%:15%) | — | H1 40 nm | LiQ 3 nm |

TABLE 2

| | | Results for the OLEDs | | | |
|---|---|---|---|---|---|
| Ex. | Voltage for 1000 cd/m2 | Efficiency at 1000 cd/m2 | Efficiency at 1000 cd/m$^2$ | CIE x/y at 1000 cd/m$^2$ | LD80 $I_0$ = 4000 cd/m$^2$ |
| 31 (comp.) | 5.0 V | 7.2 cd/A | 4.5 lm/W | 0.69/0.31 | 230 h |
| 32 (comp.) | 5.2 V | 8.1 cd/A | 4.9 lm/W | 0.68/0.32 | 250 h |
| 33 (comp.) | 4.7 V | 55 cd/A | 37 lm/W | 0.36/0.61 | 440 h |
| 34 (comp.) | 4.6 V | 54 cd/A | 37 lm/W | 0.37/0.60 | 400 h |
| 35 (comp.) | 4.2 V | 42 cd/A | 31 lm/W | 0.36/0.61 | 230 h |
| 36 (comp.) | 4.0 V | 43 cd/A | 33 lm/W | 0.38/0.59 | 300 h |
| 37 (comp.) | 3.8 V | 39 cd/A | 32 lm/W | 0.38/0.60 | 210 h |
| 38 (comp.) | 8.2 V | 17 cd/A | 6 lm/W | 0.16/0.27 | |
| 39 | 4.4 V | 7.4 cd/A | 5.3 lm/W | 0.69/0.32 | 350 h |
| 40 | 4.5 V | 8.0 cd/A | 5.6 lm/W | 0.68/0.32 | 390 h |
| 41 | 4.6 V | 54 cd/A | 37 lm/W | 0.35/0.61 | 680 h |
| 42 | 4.4 V | 52 cd/A | 37 lm/W | 0.36/0.61 | 590 h |
| 43 | 4.2 V | 57 cd/A | 43 lm/W | 0.36/0.60 | 560 h |
| 44 | 4.4 V | 54 cd/A | 39 lm/W | 0.36/0.60 | 620 h |
| 45 | 4.3 V | 53 cd/A | 38 lm/W | 0.36/0.60 | 550 h |
| 46 | 4.2 V | 58 cd/A | 43 lm/W | 0.35/0.61 | 630 h |
| 47 | 3.7 V | 55 cd/A | 47 lm/W | 0.36/0.60 | 590 h |
| 48 | 3.9 V | 59 cd/A | 48 lm/W | 0.35/0.61 | 530 h |
| 49 | 7.1 | 18 cd/A | 8 lm/W | 0.16/0.27 | |
| 50 | 3.3 V | 57 cd/A | 54 lm/W | 0.38/0.59 | 610 h |

TABLE 3
Structural formulae of the materials used
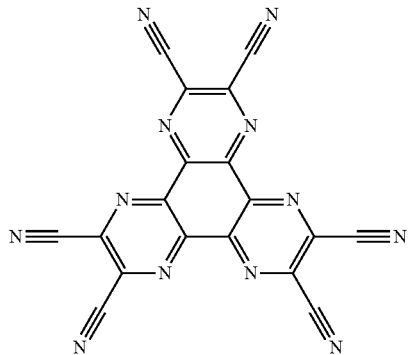 [SMILES: N#Cc1nc2c3nc(C#N)c(C#N)nc3c3nc(C#N)c(C#N)nc3c2nc1C#N]
HIL1
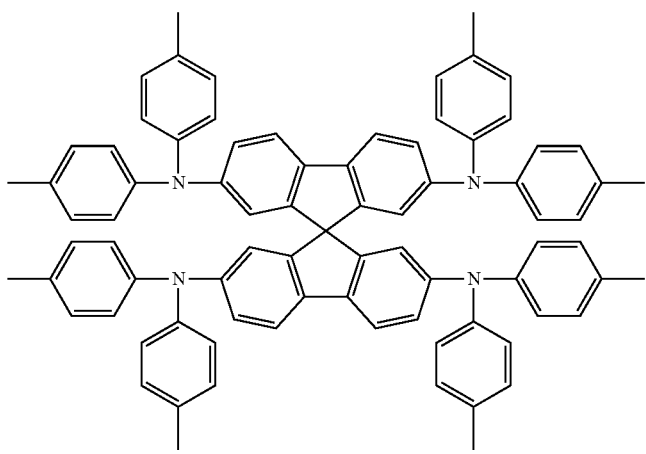
HTM1
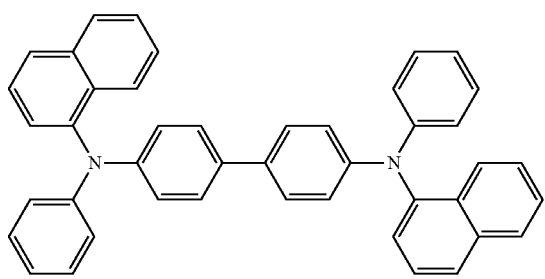 [SMILES: c1ccc(N(c2ccc(-c3ccc(N(c4ccccc4)c4cccc5ccccc45)cc3)cc2)c2cccc3ccccc23)cc1]
NPB TABLE 3-continued
Structural formulae of the materials used
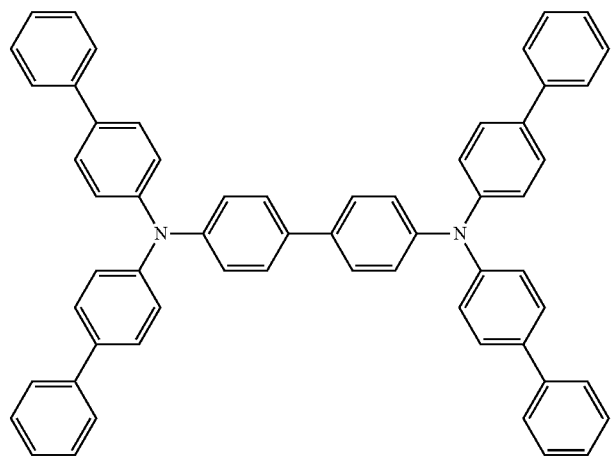 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
EBM1
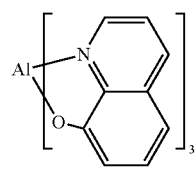
Alq₃
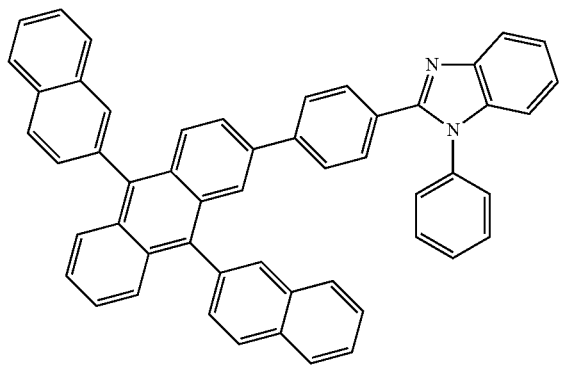 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1
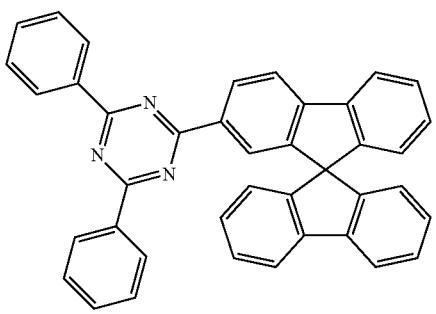 [SMILES: c1ccc(-c2nc(-c3ccccc3)nc(-c3ccc4c(c3)C3(c5ccccc5-c5ccccc53)c3ccccc3-4)n2)cc1]
H1

TABLE 3-continued
Structural formulae of the materials used
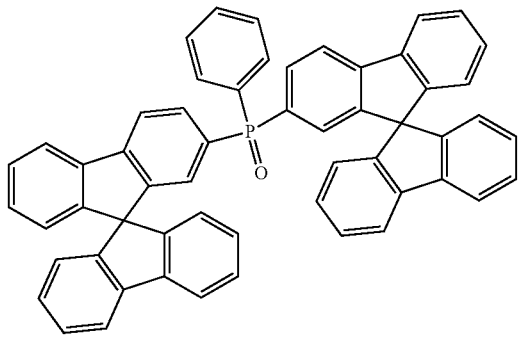 [SMILES: O=P(c1ccccc1)(c1ccc2c(c1)C1(c3ccccc3-c3ccccc31)c1ccccc1-2)c1ccc2c(c1)C1(c3ccccc3-c3ccccc31)c1ccccc1-2]
H2
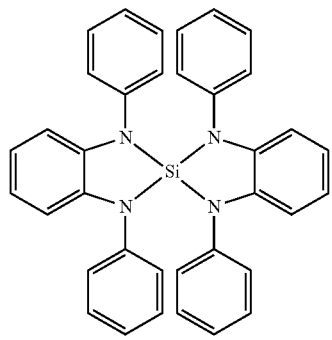 [SMILES: c1ccc(N2c3ccccc3N(c3ccccc3)[Si]23N(c2ccccc2)c2ccccc2N3c2ccccc2)cc1]
EBM3
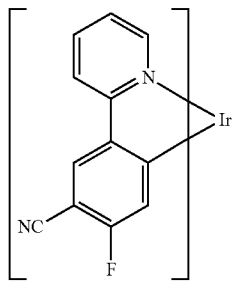
TEB1
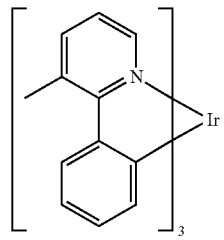
TEG1

TABLE 3-continued
Structural formulae of the materials used
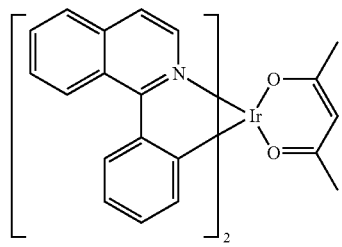
TER1
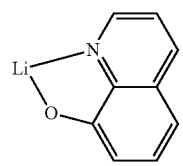
LiQ
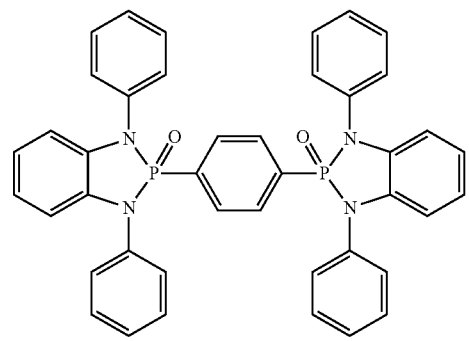 [SMILES: O=P1(c2ccc(P3(=O)N(c4ccccc4)c4ccccc4N3c3ccccc3)cc2)N(c2ccccc2)c2ccccc2N1c1ccccc1]
H3
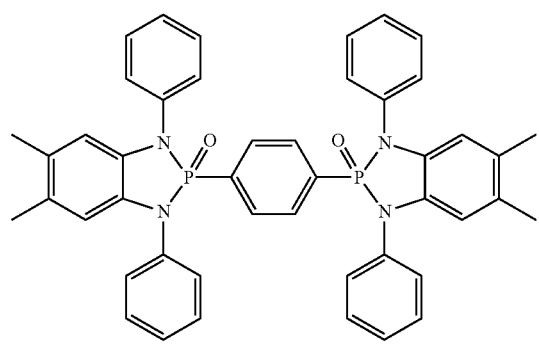
H4

TABLE 3-continued
Structural formulae of the materials used
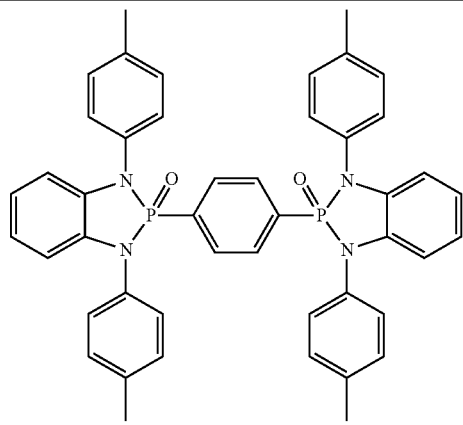
H5
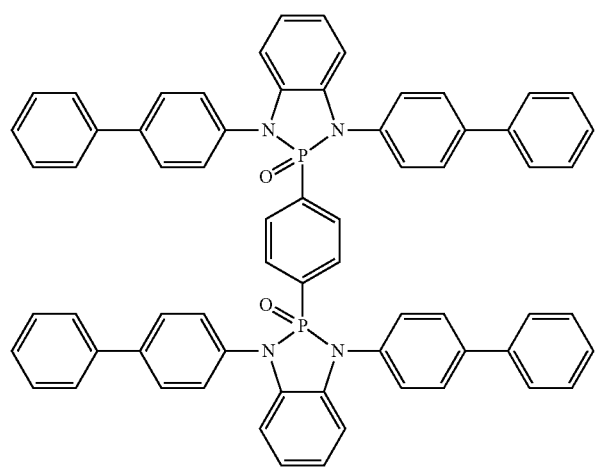 [SMILES: O=P1(c2ccc(P3(=O)N(c4ccc(-c5ccccc5)cc4)c4ccccc4N3c3ccc(-c4ccccc4)cc3)cc2)N(c2ccc(-c3ccccc3)cc2)c2ccccc2N1c1ccc(-c2ccccc2)cc1]
H6
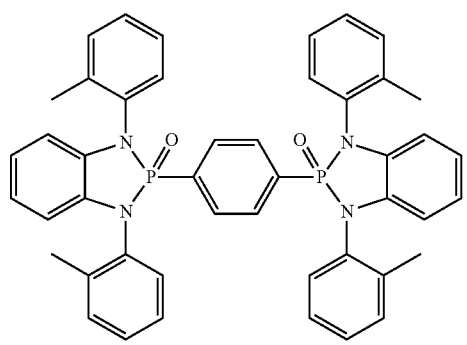 [SMILES: Cc1ccccc1N1c2ccccc2N(c2ccccc2C)P1(=O)c1ccc(P2(=O)N(c3ccccc3C)c3ccccc3N2c2ccccc2C)cc1]
H7
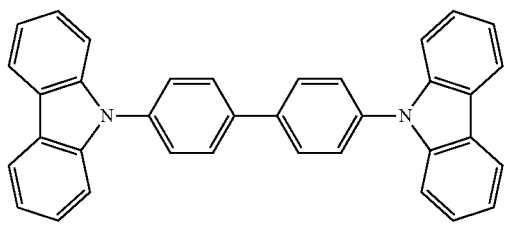 [SMILES: c1ccc2c(c1)c1ccccc1n2-c1ccc(-c2ccc(-n3c4ccccc4c4ccccc43)cc2)cc1]
CBP TABLE 3-continued Structural formulae of the materials used

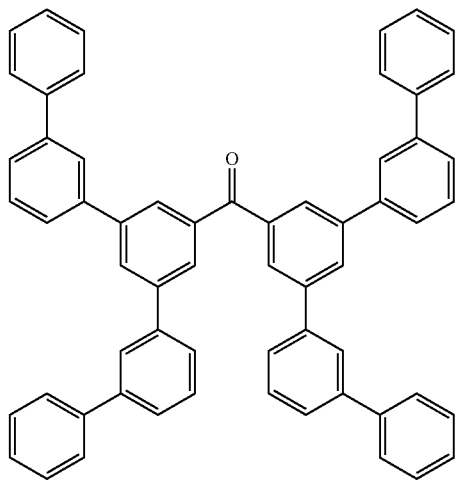 [SMILES: O=C(c1cc(-c2cccc(-c3ccccc3)c2)cc(-c2cccc(-c3ccccc3)c2)c1)c1cc(-c2cccc(-c3ccccc3)c2)cc(-c2cccc(-c3ccccc3)c2)c1]

H8

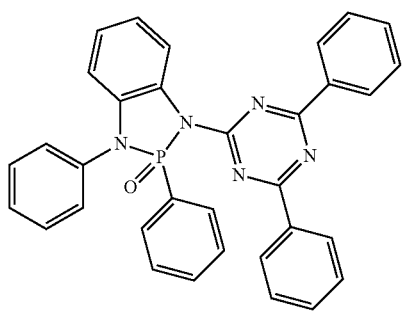 [SMILES: O=P1(c2ccccc2)N(c2ccccc2)c2ccccc2N1c1nc(-c2ccccc2)nc(-c2ccccc2)n1]

H9

Example 51

Synthesis of 6-[[2-(phenylamino)phenyl]amino]-2,4-diphenyl-1,3,5-triazine

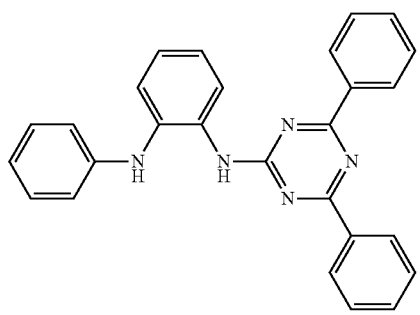 [SMILES: c1ccc(Nc2ccccc2Nc2nc(-c3ccccc3)nc(-c3ccccc3)n2)cc1]

44.3 g (240 mmol) of N-phenyl-o-phenylenediamine are initially introduced in THF and cooled to 0° C., and 136.4 ml (818 mmol) of N-ethyldiisopropylamine are added dropwise. The mixture is subsequently stirred at room temperature for a further 1 h. A solution of 64.4 g (240 mmol) of 2-chloro-4,6-diphenyl-1,3,5-triazine, dissolved in 1600 ml of THF, is then added dropwise, and the mixture is stirred at 60° C. for 96 h. After cooling, the solution is stirred with 400 ml of heptane, 80 ml of dichloromethane and 100 ml of ethanol. The solid is washed with toluene and washed by stirring with hot heptane, giving 87.7 g (211 mmol) of a crystalline solid. The overall yield is 88%.

Examples 52-54

Synthesis of the Diamines Using Heteroaromatic Compounds

The diamines shown below can be prepared from the corresponding dibromoaromatic compounds by reaction with the corresponding o-phenylenediamine analogously to Example 51.

| Ex. | Aromatic 1 | Aromatic 2 | o-Phenylenediamine | Yield |
|---|---|---|---|---|
| 52 | (p-toluidine) | (2-chloro-4,6-diphenyl-1,3,5-triazine) | (product) | 85.0% |
| 53 | (aniline) | (2-chloro-4,6-diphenylpyrimidine) | (product) | 87.0% |
| 54 | (2-chloro-4,6-diphenyl-1,3,5-triazine) | (2-chloro-4,6-diphenyl-1,3,5-triazine) | (product) | 56.0% |

Example 55

Synthesis of Diazaphospholes Using Heteroaromatic Compounds

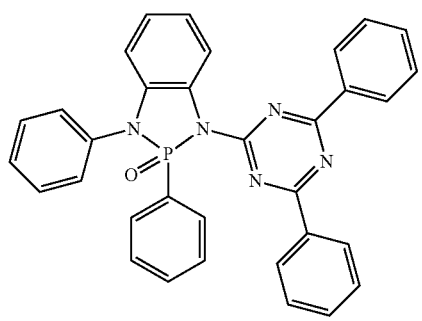 [SMILES: O=P1(c2ccccc2)N(c2ccccc2)c2ccccc2N1c1nc(-c2ccccc2)nc(-c2ccccc2)n1]

21.5 g (51.9 mmol) of 6-[[2-(phenylamino)phenyl]amino]-2,4-diphenyl-1,3,5-triazine are dissolved in 165 ml of pyridine and cooled to 0° C. 7 ml (51.9 mmol) of phenylphosphonous dichloride, dissolved in 199 ml of toluene, are added dropwise to this solution at 0° C. with vigorous stirring, and the mixture is stirred for 1 h and then heated under reflux for 24 h. The solvent is distilled off in vacuo, and the solid is washed by boiling in ethyl acetate, filtered off with suction, washed once with 100 ml of ethyl acetate and subsequently recrystallised from dioxane. Yield: 12 g (33 mmol), 69%, purity 99.9% (HPLC).

Examples 56-60

Synthesis of the Diazaphospholes

The diazaphospholes shown below can be prepared from the corresponding diaminoaromatic compounds by reaction with the corresponding phosphonous chloride analogously to Example 55.

| Ex. | Phosphonous chloride | Phenylenediamine | Diazaphosphole | Yield |
|---|---|---|---|---|
| 56 | | | | 71.0% |
| 57 | | | | 70% |
| 58 | | | | 73.0% |
| 59 | | | | 45.0% |

| Ex. | Phosphonous chloride | Phenylenediamine | Diazaphosphole | Yield |
|---|---|---|---|---|
| 60 | | | | 65.0% |

The invention claimed is:

1. An electronic device comprising at least one compound of the formula (1) or formula (39)

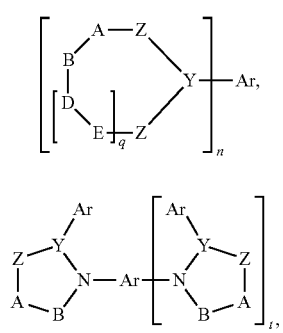

where the following applies to the symbols and indices used:

A-B and D-E are each, identically or differently on each occurrence, a unit of the following formula (2), (3), (4), (5) or (6):

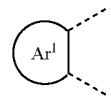
formula (2)

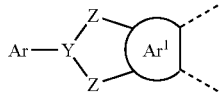
formula (3)

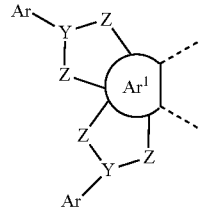

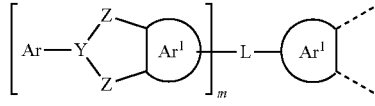

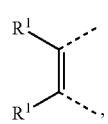

where the dashed bond in each case represents the link to Z and B or D;
and
Z is, identically or differently on each occurrence, N—R², O or S;
or
A-Z and B-Z are each, identically or differently on each occurrence, a unit of the following formula (7) and q=0,

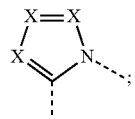
formula (7)

the dashed bond represents the linking of the unit to the compound of the formula (1), where the nitrogen is linked to the group Y;

Y is on each occurrence, identically or differently, P(=O), P(=S), P, As(=O), As(=S), As, Sb(=O), Sb(=S), Sb, Bi(=O), Bi(=S) or Bi;

Ar is on each occurrence, identically or differently, an aromatic or heteroaromatic ring system having 5 to 60 aromatic ring atoms, which may be substituted by one or more radicals $R^1$;

$Ar^1$ is on each occurrence, identically or differently, an aryl or heteroaryl group having 5 to 18 aromatic ring atoms, which may be substituted by one or more radicals $R^1$;

X is on each occurrence, identically or differently, $CR^1$ or N;

L is a single bond or a divalent, trivalent or tetravalent group;

$R^1$ is selected on each occurrence, identically or differently, from the group consisting of H, D, F, Cl, Br, I, CN, $NO_2$, $N(R^3)_2$, C(=O)$R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, P(=O)($R^3$), SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of a straight-chain alkyl group having 1 to 40 C atoms or a branched or cyclic alkyl group having 3 to 40 C atoms, each of which may be substituted by one or more radicals $R^3$, where one or more non-adjacent $CH_2$ groups may be replaced by $R^3C=CR^3$, C≡C or C=O and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

n, t is 1 to 10;

m is 1 if L is a single bond or a divalent group, or is 2 if L is a trivalent group, or is 3 if L is a tetravalent group;

q is on each occurrence, identically or differently, 0 or 1.

2. The electronic device according to claim 1, wherein $Ar^1$ stands, identically or differently on each occurrence, for an aryl or heteroaryl group having 5 to 14 aromatic ring atoms.

3. The electronic device according to claim 1, wherein the compound of the formula (1) is selected from compounds of the formulae (8) to (18):

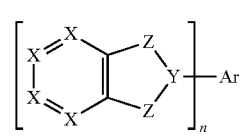

formula (8)

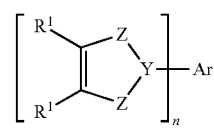

formula (9)

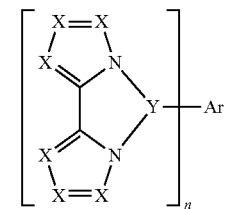

formula (10)

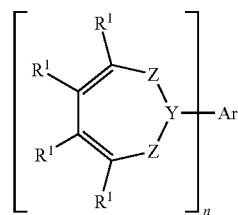

formula (11)

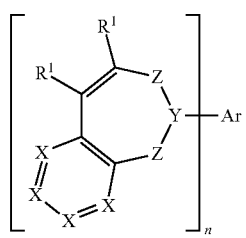

formula (12)

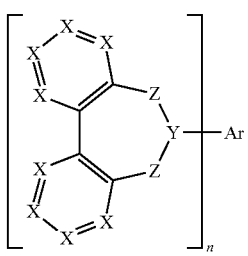

formula (13)

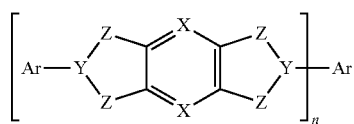

formula (14)

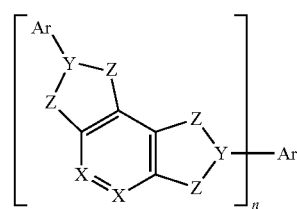

formula (15)

formula (16)

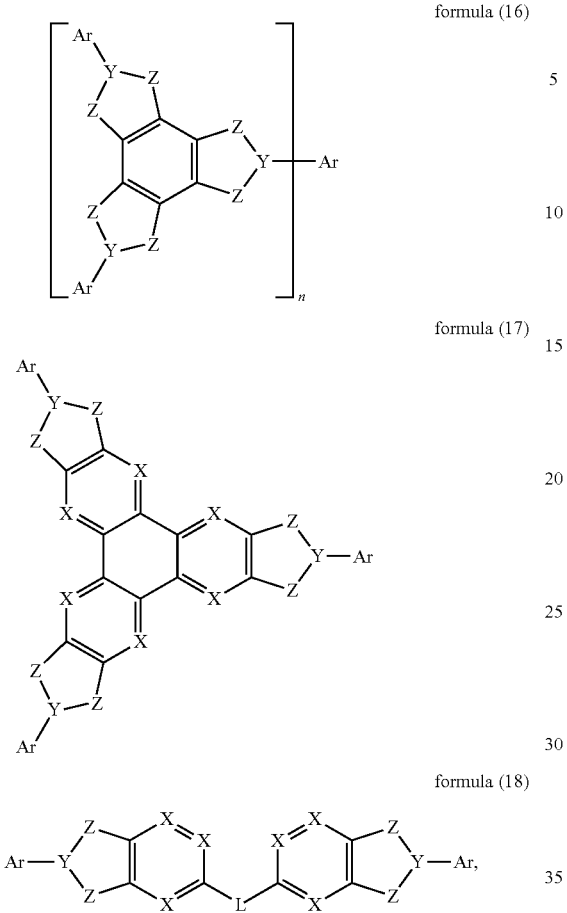

formula (17)

formula (18)

where the symbols and indices used have the meanings indicated in claim 1.

4. The electronic device according to claim 1, wherein the symbol Y stands for P(=O) and the symbol Z stands on each occurrence, identically or differently, for N—$R^2$.

5. The electronic device according to claim 1, wherein the group Ar stands for an aromatic or heteroaromatic ring system having 5 to 30 aromatic ring atoms, selected from the group consisting of the units of the following formulae (19) to (36), where the dashed bond in each case indicates a link to the group Y in formula (1) or to N in formula (39):

formula (19)

formula (20)

formula (21)

formula (22)

formula (23)

formula (24)

formula (25)

formula (26)

formula (27)

formula (28)

formula (29)

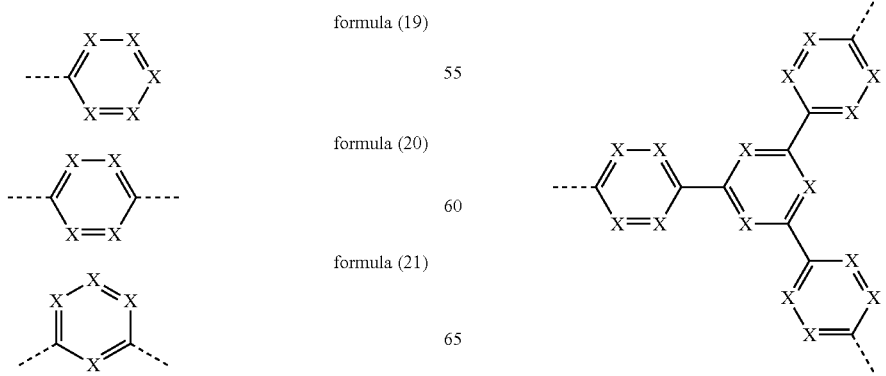

-continued

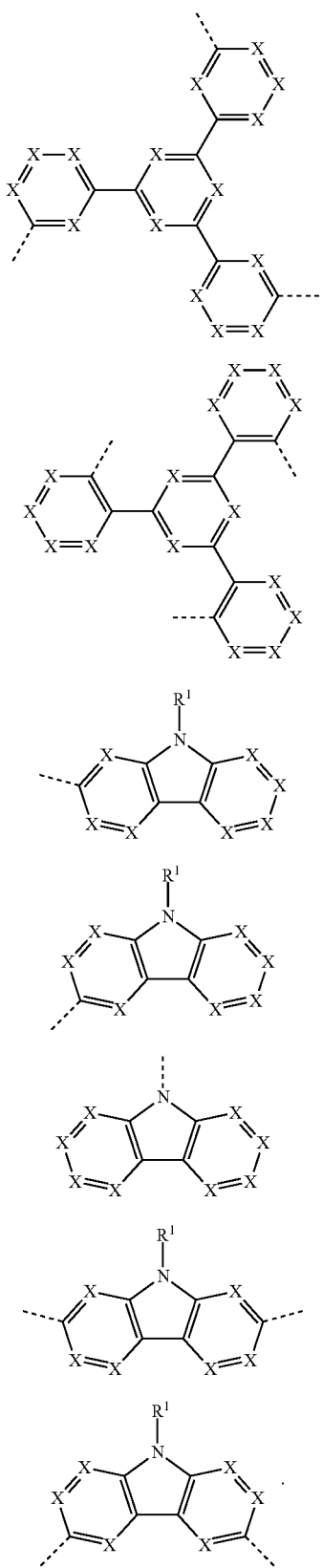

formula (30)

formula (31)

formula (32)

formula (33)

formula (34)

formula (35)

formula (36)

6. The electronic device according to claim 1, wherein $R^2$ is selected, identically or differently on each occurrence, from the group consisting of an aromatic or heteroaromatic ring system having 5 to 24 aromatic ring atoms, which may in each case be substituted by one or more radicals $R^3$.

7. The electronic device according to claim 1, wherein the following applies to the symbols and indices:
- $Ar^1$ is, identically or differently on each occurrence, an aryl or heteroaryl group having 5 to 14 aromatic ring atoms;
- Y is on each occurrence, identically or differently, P(=O) or P(=S);
- Z is, identically or differently on each occurrence, N—$R^2$ if it does not form a ring of the formula (7) with A or B;
- X stands for $CR^1$ or N, where a maximum of two symbols X stand for N;
- Ar is, identically or differently, an aromatic or heteroaromatic ring system having 5 to 30 aromatic ring atoms;
- q is 0;
- n is 1, 2, 3 or 4;
- $R^1$ is selected, identically or differently on each occurrence, from the group consisting of H, I), F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C$=$CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;
- $R^2$ is selected on each occurrence, identically or differently, from the group consisting of a straight-chain alkyl group having 1 to 10 C atoms or a branched or cyclic alkyl group having 3 to 10 C atoms, each of which may be substituted by one or more radicals $R^3$, where one or more H atoms may be replaced by F or D, an aromatic or heteroaromatic ring system having 5 to 30 aromatic ring atoms, Which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$;
- the other symbols and indices have the meanings indicated in claim 1.

8. The electronic device according to claim 1, wherein the following applies to the symbols and indices used:
- $Ar^1$ is selected, identically or differently on each occurrence, from the group consisting of benzene, pyridine, pyrimidine, pyridazine, pyrazine, triazine, furan, thiophene, pyrrole, naphthalene, quinoline, isoquinoline, quinoxaline, indole, benzofuran, benzothiophene and carbazole;
- Y is P(=O);
- Z is, identically or differently on each occurrence, N—$R^2$ if it does not form a ring of the formula (7) with A or B;
- X is, identically or differently on each occurrence, $CR^1$;
- Ar is an aromatic or heteroaromatic ring system having 5 to 24 aromatic ring atoms, which is built up from in each case one or more of the groups benzene, pyridine, pyrimidine, pyridazine, pyrazine, pyrrole, thiophene, furan, naphthalene, triphenylene, quinoline, isoquinoline, quinoxaline, indole, benzothiophene or benzofuran;

q is 0;

n is 1 or 2;

$R^1$ is selected, identically or differently on each occurrence, from the group consisting of H, D, F, CN, a straight-chain alkyl group having 1 to 10 C atoms, or a branched or cyclic alkyl group having 3 to 10 C atoms, or an alkenyl group having 2 to 10 C atoms, each of which may be substituted by one or more radicals $R^3$, where one or more H atoms may be replaced by D, an aromatic or heteroaromatic ring system having 5 to 12 aromatic ring atoms, which may in each case be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of an aromatic or heteroaromatic ring system having 5 to 24 aromatic ring atoms, which may in each case be substituted by one or more radicals $R^3$;

the other symbols and indices used have the meanings indicated in claim 1.

9. The electronic device according to claim 1, wherein the device is selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices.

10. The electronic device according to claim 3, wherein the compound of the formula (1) or formulae (8) to (18) is employed as matrix material for fluorescent or phosphorescent emitters and/or as hole-blocking material in a hole-blocking layer and/or as electron-transport material in an electron-transport layer or an electron-injection layer and/or as electron-blocking material or exciton-blocking material in an electron-blocking or exciton-blocking layer and/or as hole-transport material in a hole-transport layer or hole-injection layer.

11. The electronic device according to claim 10, wherein the phosphorescent emitter employed is a compound which contains copper, molybdenum, tungsten, rhenium, ruthenium, osmium, rhodium, iridium, palladium, platinum, silver, gold or europium.

12. A compound of the formula (1')

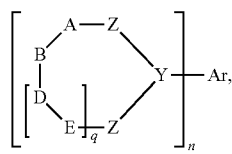

formula (1')

where the following applies to the symbols and indices used:

A-B and D-E are each, identically or differently on each occurrence, a unit of the following formula (2), (3), (4), (5) or (6):

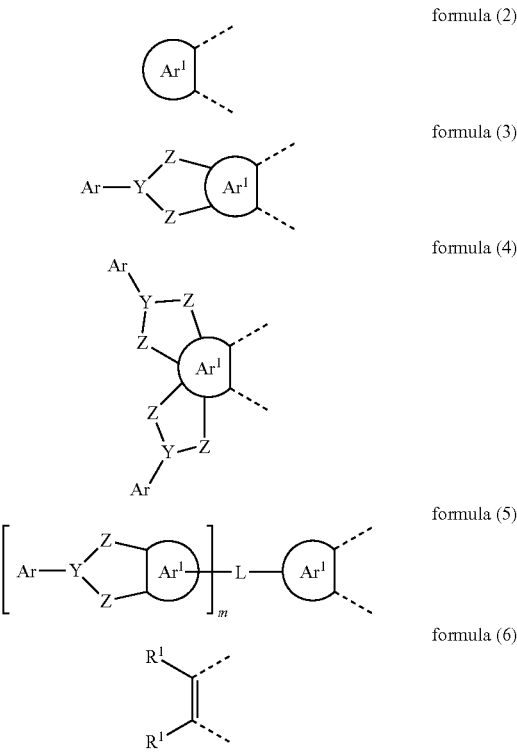

where the dashed bond in each case represents the bond to Z and B or D;

and

Z is, identically or differently on each occurrence, N—$R^2$, O or S, with the proviso that both groups Z bonded to the same group Y do not stand for O;

or

A-Z and B-Z are each, identically or differently on each occurrence, a unit of the following formula (7) and q=0,

formula (7)

the dashed bond in formula (7) in each case represents the linking of this unit in the compound of the formula (1), where the nitrogen is linked to the group Y;

Y is on each occurrence, identically or differently, P(=O), As(=O), As(=S), Sb(=O), Sb(=S), Bi(=O) or Bi(=S);

Ar is on each occurrence, identically or differently, an aromatic or heteroaromatic ring system having 5 to 60 aromatic ring atoms, which may be substituted by one or more radicals $R^1$;

$Ar^1$ is on each occurrence, identically or differently, an aryl or heteroaryl group having 5 to 16 aromatic ring atoms, which may be substituted by one or more radicals $R^1$;

X is on each occurrence, identically or differently, $CR^1$ or N;

L is a single bond or a divalent, trivalent or tetravalent group;

$R^1$ is selected on each occurrence, identically or differently, from the group consisting of H, D, F, Cl, Br, I, CN, NO$_2$, N(R$^3$)$_2$, C(=O)R$^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more non-adjacent CH$_2$ groups may be replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, O, S or CONR$^3$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^3$, an aryloxy or heteroaryloxy group having 5 to 60 aromatic ring atoms, which may be substituted by one or more radicals R$^3$, or a combination of these systems, where two or more adjacent substituents R$^1$ may optionally form a monocyclic or polycyclic, aliphatic, aromatic or heteroaromatic ring system, which may be substituted by one or more radicals R$^3$;

R$^2$ is selected on each occurrence, identically or differently, from the group consisting of a straight-chain alkyl group having 1 to 40 C atoms or a branched or cyclic alkyl group having 3 to 40 C atoms, each of which may be substituted by one or more radicals R$^3$, where one or more non-adjacent CH$_2$ groups may be replaced by R$^3$C=CR$^3$, C≡C or C=O and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^3$, or a combination of these systems; R$^1$ and R$^2$ which are adjacent to one another in the 1,2-position may optionally form a monocyclic or polycyclic, aliphatic, aromatic or heteroaromatic ring system, which may be substituted by one or more radicals R$^3$;

R$^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^3$ may form a mono- or polycyclic, aliphatic, aromatic or heteroaromatic ring system with one another;

n is 1 to 10;

m is 1 if L is a single bond or a divalent group, or is 2 if L is a trivalent group, or is 3 if L is a tetravalent group;

q is on each occurrence, identically or differently, 0 or 1;

the following compounds are excluded from the invention:

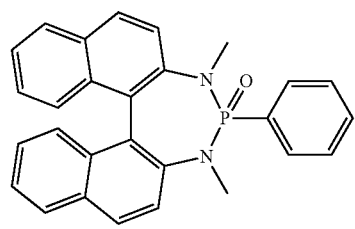

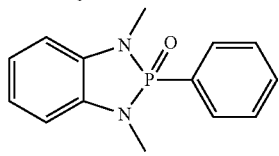

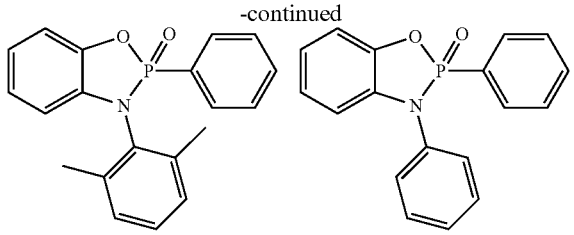

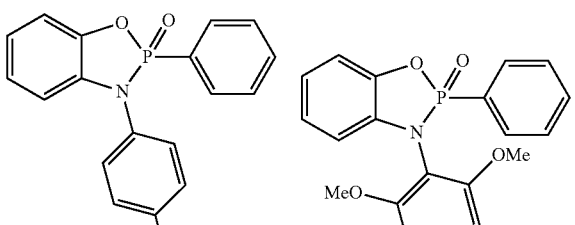

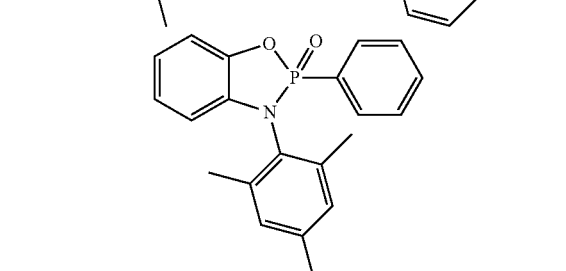

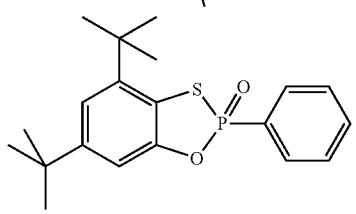

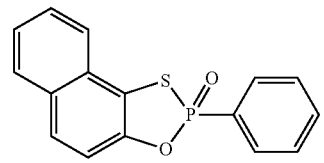

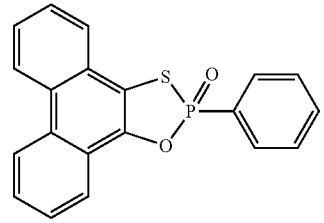

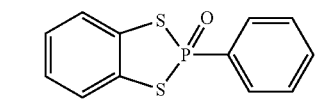

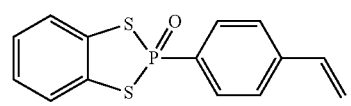

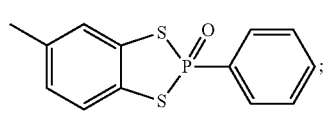

or a compound of the formula (39),

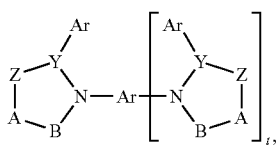

formula (39)

wherein t is 1 to 10.

13. An electronic device which comprises the compound according to claim 12.

14. A process for the preparation of the compound according to claim 12 which comprises reacting an ortho-diamino-substituted aromatic compound, in which the amino groups are unsubstituted or monosubstituted, with an aromatic phosphonyl chloride derivative or an aromatic oligophosphonyl chloride derivative.

15. An oligomer, polymer or dendrimer containing one or more compounds according to claim 12, where one or more bonds are present from the compound to the polymer, oligomer or dendrimer, or an oligomer or polymer of the formula (37) or formula (38):

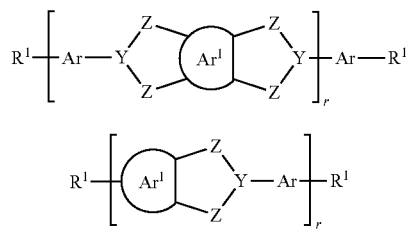

formula (37)

formula (38)

where symbols used have the meanings indicated in claim 12, and r stands for an integer between 2 and 1,000,000.

16. The electronic device according to claim 1, wherein $Ar^1$ stands, identically or differently on each occurrence, for benzene, pyridine, pyrimidine, pyridazine, pyrazine, triazine, furan, thiophene, pyrrole, naphthalene, phenanthrene, quinoline, isoquinoline, quinoxaline, indole, benzofuran, benzothiophene or carbazole.

17. The electronic device according to claim 1, wherein $R^2$ is selected, identically or differently on each occurrence, phenyl, naphthyl, biphenyl or terphenyl, each of which may be substituted by one or more radicals $R^3$.

18. The electronic device according to claim 1, wherein the following applies to the symbols and indices:

$Ar^1$ is, identically or differently on each occurrence, an aryl or heteroaryl group having 6 aromatic ring atoms;

Y is on each occurrence, identically or differently, P(=O) or P(=S);

Z is, identically or differently on each occurrence, N—$R^2$ if it does not form a ring of the formula (7) with A or B;

X stands for $CR^1$ or N, where a maximum of one symbol X stands for N;

Ar is, identically or differently, an aromatic or heteroaromatic ring system having 5 to 24 aromatic ring atoms; and, none of the aryl or heteroaryl groups of the aromatic or heteroaromatic ring system contains more than 10 aromatic ring atoms;

q is 0;

n is 1, 2 or 3;

$R^1$ is selected, identically or differently on each occurrence, from the group consisting of H, D, F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C=CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of a straight-chain alkyl group having 1 to 10 C atoms or a branched or cyclic alkyl group having 3 to 10 C atoms, each of which may be substituted by one or more radicals $R^3$, where one or more atoms may be replaced by F or D, an aromatic or heteroaromatic ring system having 5 to 30 aromatic ring atoms, which may in each case be substituted by one or more radicals $R^3$, or a combination of these systems; $R^1$ and $R^2$ which are adjacent to one another in the 1,2-position may optionally form a monocyclic or polycyclic, aliphatic, aromatic or heteroaromatic ring system, which may be substituted by one or more radicals $R^3$;

the other symbols and indices have the meanings indicated in claim 1.

19. The electronic device according to claim 1, wherein the following applies to the symbols and indices used:

$Ar^1$ is selected, identically or differently on each occurrence, from the group consisting of benzene, pyridine, pyrimidine, pyridazine, pyrazine, triazine, furan, thiophene, pyrrole, naphthalene, quinoline, isoquinoline, quinoxaline, indole, benzofuran, benzothiophene and carbazole;

Y is P(=O);

Z is, identically or differently on each occurrence, N—$R^2$ if it does not form a ring of the formula (7) with A or B;

X is, identically or differently on each occurrence, $CR^1$;

Ar is an aromatic or heteroaromatic ring system having 5 to 24 aromatic ring atoms, which is built up from in each case one or more of the groups benzene, pyridine, pyrimidine, pyridazine, pyrazine or triazine;

q is 0;

n is 1 or 2;

$R^1$ is selected, identically or differently on each occurrence, from the group consisting of H, D, F, CN, a straight-chain alkyl group having 1 to 4 C atoms, or a branched or cyclic alkyl group having 3 to 5 C atoms, or an alkenyl group having 2 to 4 C atoms, each of which may be substituted by one or more radicals $R^3$, where one or more H atoms may be replaced by I), an aromatic or heteroaromatic ring system having 5 to 12 aromatic ring atoms, which may in each case be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

R² is selected on each occurrence, identically or differently, from the group consisting of an aromatic or heteroaromatic ring system having 5 to 24 aromatic ring atoms, which may in each case be substituted by one or more radicals R³;

the other symbols and indices used have the meanings indicated in claim 1.

20. The electronic device according to claim 10, wherein the phosphorescent emitter employed is a compound which contains iridium or platinum.

21. The electronic device according to claim 1, wherein
R¹ is selected on each occurrence, identically or differently, from the group consisting of H, D, F, Cl, Br, I, CN, $NO_2$, $N(R^3)_2$, $C(=O)R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R³, where one or more non-adjacent $CH_2$ groups may be replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals R³, an aryloxy or heteroaryloxy group having 5 to 60 aromatic ring atoms, Which may be substituted by one or more radicals R³, or a combination of these systems;

R² is selected on each occurrence, identically or differently, from the group consisting of a straight-chain alkyl group having 1 to 40 C atoms or a branched or cyclic alkyl group having 3 to 40 C atoms, each of which may be substituted by one or more radicals R³, where one or more non-adjacent $CH_2$ groups may be replaced by $R^3C=CR^3$, $C≡C$ or $C=O$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals R³, or a combination of these systems; and R³ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN.

22. The compound according to claim 12, wherein
R¹ is selected on each occurrence, identically or differently, from the group consisting of H, D, F, Cl, Br, I, CN, $NO_2$, $N(R^3)_2$, $C(=O)R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R³, where one or more non-adjacent $CH_2$ groups may be replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals R³, an aryloxy or heteroaryloxy group having 5 to 60 aromatic ring atoms, which may be substituted by one or more radicals R³, or a combination of these systems;

R² is selected on each occurrence, identically or differently, from the group consisting of a straight-chain alkyl group having 1 to 40 C atoms or a branched or cyclic alkyl group having 3 to 40 C atoms, each of which may be substituted by one or more radicals R³, where one or more non-adjacent $CH_2$ groups may be replaced by $R^3C=CR^3$, $C≡C$ or $C=O$ and where one or more atoms may be replaced by D, F, Cl, Br, I, CN or $NO_2$, an aromatic or heteroaromatic ring system having 5 to 60 aromatic ring atoms, which may in each case be substituted by one or more radicals R³, or a combination of these systems; and R³ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN.

* * * * *